United States Patent
Elsohly et al.

(10) Patent No.: US 10,322,103 B2
(45) Date of Patent: *Jun. 18, 2019

(54) COMPOSITIONS FOR PREVENTION/PROPHYLACTIC TREATMENT OF POISON IVY DERMATITIS

(71) Applicant: The University of Mississippi, University, MS (US)

(72) Inventors: Mahmoud Elsohly, Oxford, MS (US); Waseem Gul, Oxford, MS (US); Mohammad Khalid Ashfaq, Oxford, MS (US)

(73) Assignee: UNIVERSITY OF MISSISSIPPI, University, MS (US)

(*) Notice: Subject to any disclaimer, the term of this patent is extended or adjusted under 35 U.S.C. 154(b) by 0 days.

This patent is subject to a terminal disclaimer.

(21) Appl. No.: 15/563,597

(22) PCT Filed: Jan. 12, 2016

(86) PCT No.: PCT/US2016/013090
§ 371 (c)(1),
(2) Date: Oct. 1, 2017

(87) PCT Pub. No.: WO2016/160090
PCT Pub. Date: Oct. 6, 2016

(65) Prior Publication Data
US 2018/0078520 A1    Mar. 22, 2018

Related U.S. Application Data

(60) Continuation of application No. 14/675,773, filed on Apr. 1, 2015, now Pat. No. 9,408,822, which is a division of application No. 13/860,861, filed on Apr. 11, 2013, now Pat. No. 9,029,417, which is a division of application No. 12/936,204, filed as application No. PCT/US2009/039472 on Apr. 3, 2009, now Pat. No. 8,486,998.

(60) Provisional application No. 61/042,118, filed on Apr. 3, 2008.

(51) Int. Cl.
| | |
|---|---|
| *A61K 31/216* | (2006.01) |
| *A61K 31/222* | (2006.01) |
| *A61K 31/225* | (2006.01) |
| *C07C 229/08* | (2006.01) |
| *C07C 229/36* | (2006.01) |
| *C07C 229/42* | (2006.01) |
| *C07C 237/04* | (2006.01) |
| *C07C 237/12* | (2006.01) |
| *C07D 209/12* | (2006.01) |

(52) U.S. Cl.
CPC .......... *A61K 31/225* (2013.01); *A61K 31/216* (2013.01); *A61K 31/222* (2013.01); *C07C 229/08* (2013.01); *C07C 229/36* (2013.01); *C07C 229/42* (2013.01); *C07C 237/04* (2013.01); *C07C 237/12* (2013.01); *C07D 209/12* (2013.01)

(58) Field of Classification Search
CPC .. A61K 31/216; A61K 31/222; A61K 31/225; C07C 229/08; C07C 229/36; C07C 229/42; C07C 237/04; C07C 237/12; C07D 209/12; A61P 17/00
See application file for complete search history.

(56) References Cited

U.S. PATENT DOCUMENTS

| | | | | |
|---|---|---|---|---|
| 3,930,005 A | * | 12/1975 | Wojnar | C07D 473/00 514/263.37 |
| 4,428,965 A | | 1/1984 | Elsohly et al. | |
| 2008/0107742 A1 | | 5/2008 | Hare | |
| 2013/0303582 A1 | * | 11/2013 | Elsohly | A61K 31/222 514/414 |

FOREIGN PATENT DOCUMENTS

WO    WO 2013/166218 A1    11/2013

OTHER PUBLICATIONS

Elsohly et al. (Journal of Pharmaceutical Sciences, (1983) vol. 72, No. 7, p. 792-795).*
On-line Medical Dictionary (Jul. 7, 2005).*
International Search Report and the Written Opinion of PCT/US2016/013090 dated May 23, 2016.

* cited by examiner

*Primary Examiner* — Valerie Rodriguez-Garcia
(74) *Attorney, Agent, or Firm* — Hershkovitz & Associates, PLLC; Abe Hershkovitz; Eugene C. Rzucidlo

(57) ABSTRACT

The present invention, in one or more embodiments, comprises derivatives of 3-n-pentadecylcatechol (poison ivy urushiol saturated congener) and/or 3-n-heptadecyl catechol (poison oak urushiol saturated congener) as compositions for the prevention and/or prophylactic treatment of contact dermatitis caused by poison ivy and poison oak. The present invention is also directed towards processes for making such compounds. Disclosed are compounds which are effective for tolerizing and desensitizing a subject against allergens contained in plants of the Anacardiaceae and Ginkgoaceae families comprising urushiol esters of general formula (IA) [Formula should be entered here] tolerizing and desensitizing mammals, including humans, to allergens contained in plants of the Anacardiaceae and Ginkgoaceae families is attained by administering a formulation containing at least one urushiol ester compound.

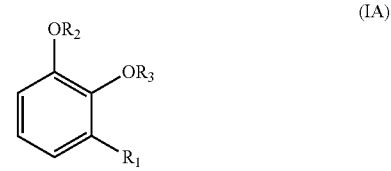

(IA)

19 Claims, 40 Drawing Sheets

TEST # 1. The total test scores of all groups (I - V) recorded at 24, 48 and 72 hrs post urushiol skin challenge.

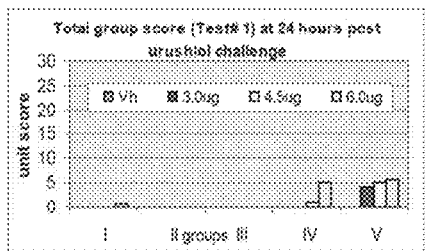

Figure 1A.

| Table 1A. Total group scores (Test #1) at 24 hrs post urushiol challenge |||||| 
|---|---|---|---|---|---|
| Dose | Group I | Group II | Group III | Group IV | Group V |
| vehicle | 0 | 0 | 0 | 0 | 0 |
| 3.0ug | 0 | 0 | 0 | 0 | 4 |
| 4.5ug | 0 | 0 | 0 | 1 | 5 |
| 6.0ug | 0.5 | 0 | 0 | 5 | 5.5 |

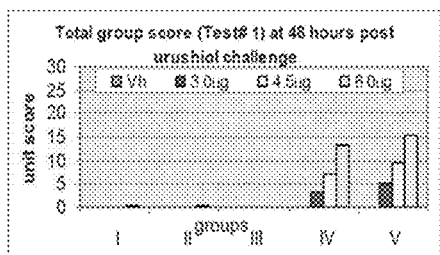

Figure 1B.

| Table 1B. Total group scores (Test #1) at 48 hrs post urushiol challenge |||||| 
|---|---|---|---|---|---|
| Dose | Group I | Group II | Group III | Group IV | Group V |
| vehicle | 0 | 0 | 0 | 0 | 0 |
| 3.0ug | 0 | 0 | 0 | 3.5 | 5 |
| 4.5ug | 0 | 0 | 0 | 7 | 9.5 |
| 6.0ug | 0.5 | 0.25 | 0 | 13.3 | 15.5 |

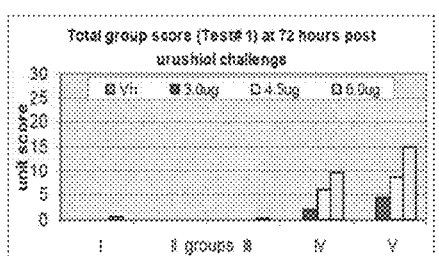

Figure 1C.

| Table 1C. Total group scores (Test #1) at 72 hrs post urushiol challenge |||||| 
|---|---|---|---|---|---|
| Dose | Group I | Group II | Group III | Group IV | Group V |
| vehicle | 0 | 0 | 0 | 0 | 0 |
| 3.0ug | 0 | 0 | 0 | 2.0 | 4.5 |
| 4.5ug | 0 | 0 | 0 | 6.0 | 8.5 |
| 6.0ug | 0.5 | 0.5 | 0.25 | 9.5 | 15 |

TEST # 2. The total test scores of all groups (I - V) recorded at 24, 48 and 72 hrs post urushiol skin challenge.

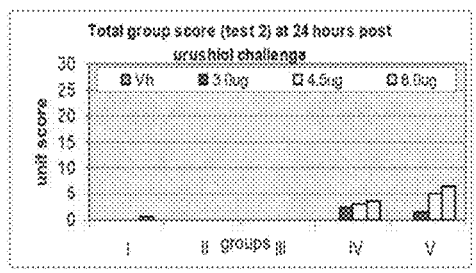

Figure 2A.

| Table 2A. Total group scores (Test #2) at 24 hours post urushiol challenge | | | | | |
|---|---|---|---|---|---|
| Dose | Group I | Group II | Group III | Group IV | Group V |
| vehicle | 0 | 0 | 0 | 0 | 0 |
| 3.0ug | 0 | 0 | 0 | 2.5 | 1.5 |
| 4.5ug | 0 | 0 | 0 | 3.0 | 5.0 |
| 6.0ug | 0.5 | 0 | 0 | 3.5 | 6.5 |

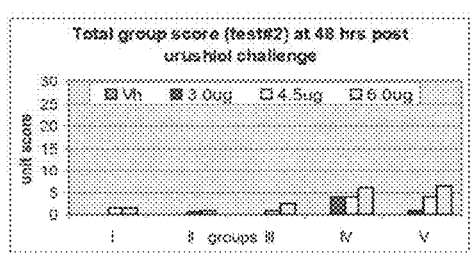

Figure 2B.

| Table 2B. Total group scores (Test #2) at 48 hours post urushiol challenge | | | | | |
|---|---|---|---|---|---|
| Dose | Group I | Group II | Group III | Group IV | Group V |
| vehicle | 0 | 0 | 0 | 0 | 0.0 |
| 3.0ug | 0 | 0 | 0 | 4.0 | 1.0 |
| 4.5ug | 1.5 | 0.5 | 1 | 4.0 | 4.0 |
| 6.0ug | 1.5 | 1.0 | 2.5 | 6.0 | 6.5 |

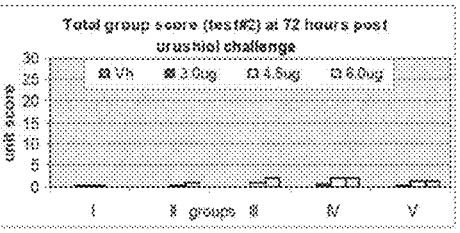

Figure 2C.

| Table 2C. Total group scores (Test #2) at 72 hours post urushiol challenge | | | | | |
|---|---|---|---|---|---|
| Dose | Group I | Group II | Group III | Group IV | Group V |
| vehicle | 0 | 0 | 0 | 0 | 0 |
| 3.0ug | 0.5 | 0 | 0 | 0.75 | 0.5 |
| 4.5ug | 0.5 | 0.5 | 1.0 | 2.0 | 1.5 |
| 6.0ug | 0 | 1.0 | 2.0 | 2.0 | 1.5 |

Results of Test #3. Skin lesions scores of all groups (I - V) recorded at 24, 48 and 72 hours post urushiol skin challenge.

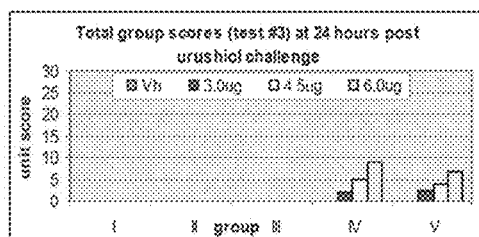

Figure 3A.

| Table 3A. Total group scores of Test #3 at 24 hrs post urushiol challenge | | | | | |
|---|---|---|---|---|---|
| Dose | Group I | Group II | Group III | Group IV | Group V |
| vehicle | 0 | 0 | 0 | 0 | 0 |
| 3.0ug | 0 | 0 | 0 | 2.0 | 2.5 |
| 4.5ug | 0 | 0 | 0 | 6.0 | 4.0 |
| 6.0ug | 0 | 0 | 0 | 9.0 | 7.0 |

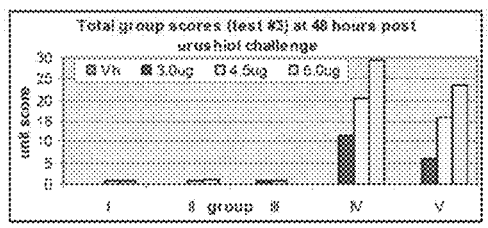

Figure 3B.

| Table 3B. Total group scores of Test #3 at 48 hrs post urushiol challenge | | | | | |
|---|---|---|---|---|---|
| Dose | Group I | Group II | Group III | Group IV | Group V |
| vehicle | 0 | 0 | 0 | 0 | 0 |
| 3.0ug | 0 | 0 | 0.5 | 11.5 | 6.0 |
| 4.5ug | 0.5 | 0.5 | 0.5 | 20.5 | 16.0 |
| 6.0ug | 0.5 | 1.0 | 0 | 29.5 | 23.5 |

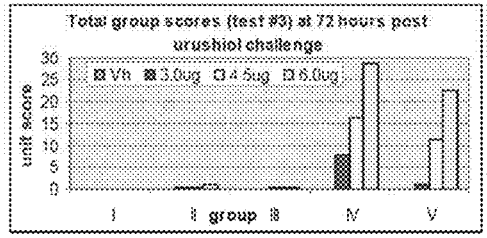

Figure 3C.

| Table 3C. Total group scores of Test #3 at 72 hrs post urushiol challenge | | | | | |
|---|---|---|---|---|---|
| Dose | Group I | Group II | Group III | Group IV | Group V |
| vehicle | 0 | 0 | 0 | 0 | 0 |
| 3.0ug | 0 | 0.5 | 0 | 8.0 | 1.0 |
| 4.5ug | 0 | 0.5 | 0.5 | 16.5 | 11.5 |
| 6.0ug | 0 | 1.0 | 0.5 | 26.5 | 22.5 |

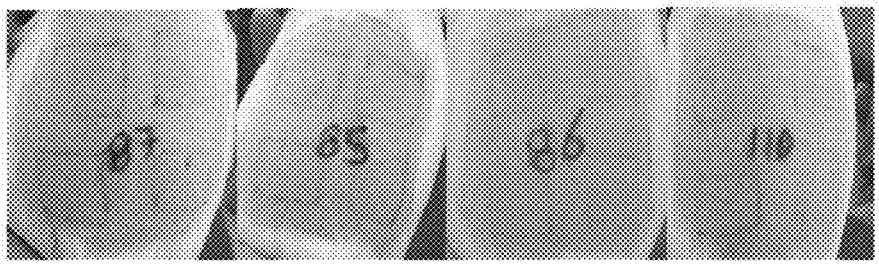
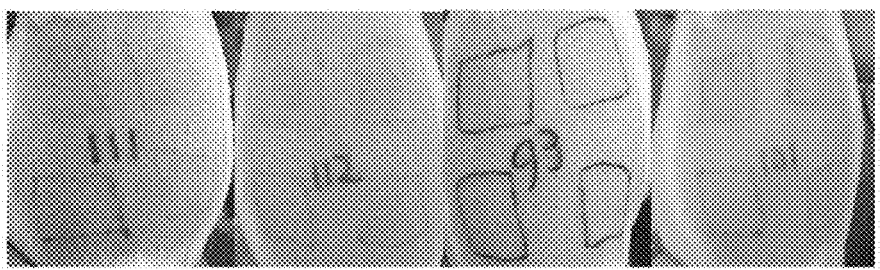
Figure 4A. Test #3, (Group I)
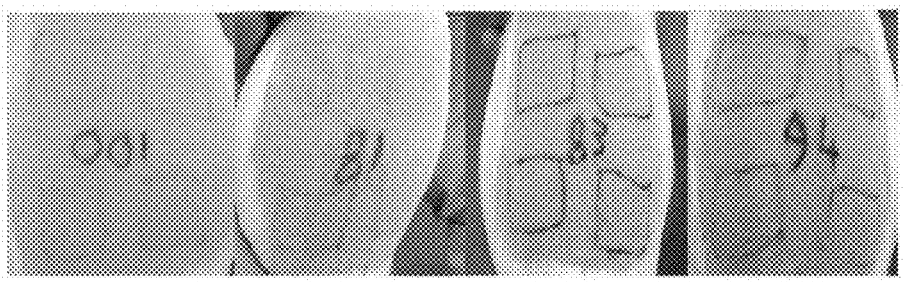
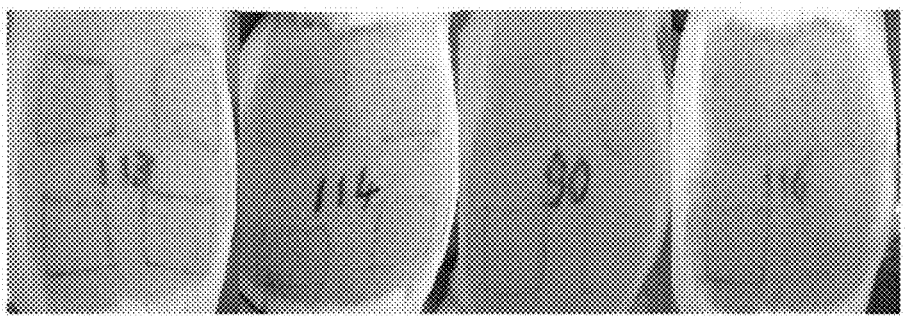
Figure 4B. Test #3,(Group II)

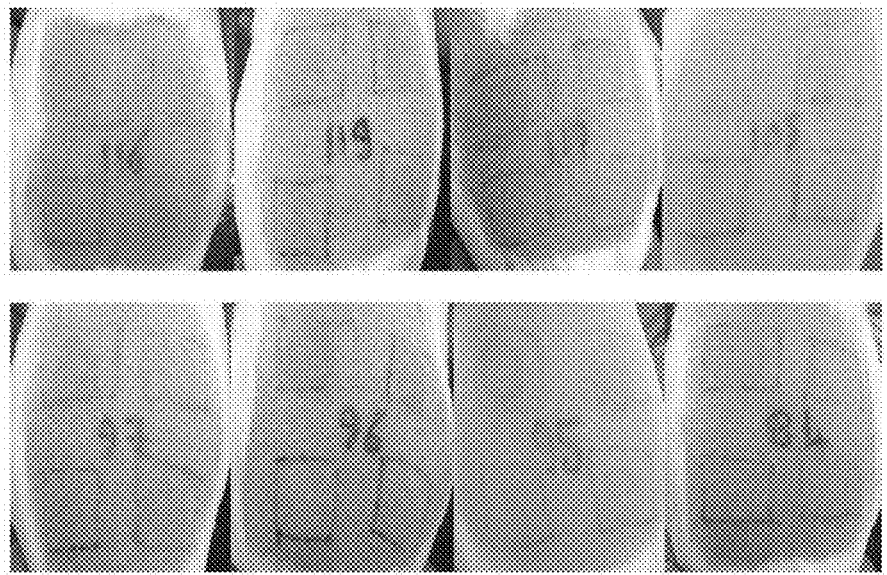
Figure 4C. Test #3. (Group III)
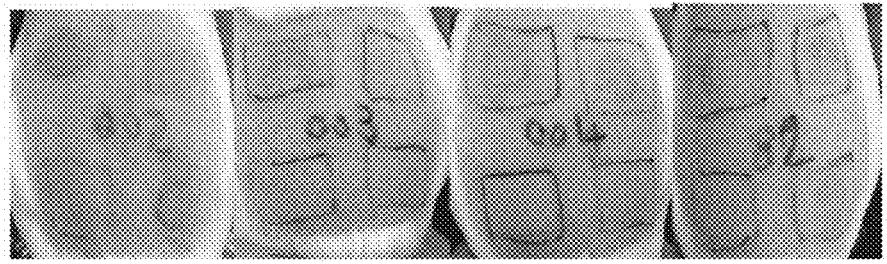
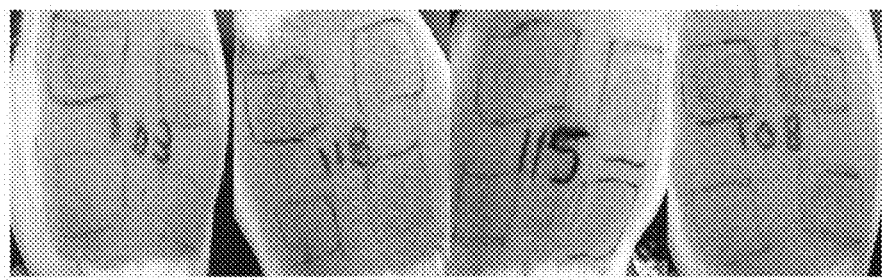
Figure 4D. Test #3. (Group IV)

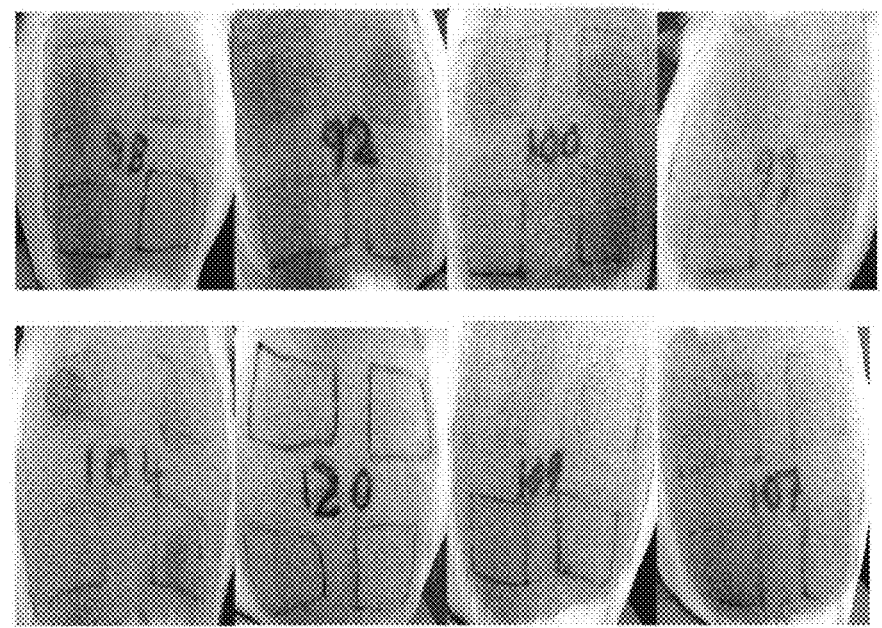
Figure 4E. Test #3, (Group V)

| Table 4A. Total group scores at 24 hrs post urushiol challenge | | |
|---|---|---|
| Dose | Group IV | Group V |
| vehicle | 0 | 0 |
| 3.0ug | 0 | 0 |
| 4.5ug | 0 | 1 |
| 6.0ug | 0 | 2.5 |

| Table 4B. Total group scores at 48 hrs post urushiol challenge | | |
|---|---|---|
| Dose | Group IV | Group V |
| vehicle | 0 | 0 |
| 3.0ug | 0 | 1 |
| 4.5ug | 0.5 | 4 |
| 6.0ug | 0.5 | 6.5 |

| Table 4C. Total group scores at 72 hrs post urushiol challenge | | |
|---|---|---|
| Dose | Group IV | Group V |
| vehicle | 0 | 0 |
| 3.0ug | 0 | 0.5 |
| 4.5ug | 0 | 6.5 |
| 6.0ug | 1.5 | 19.5 |

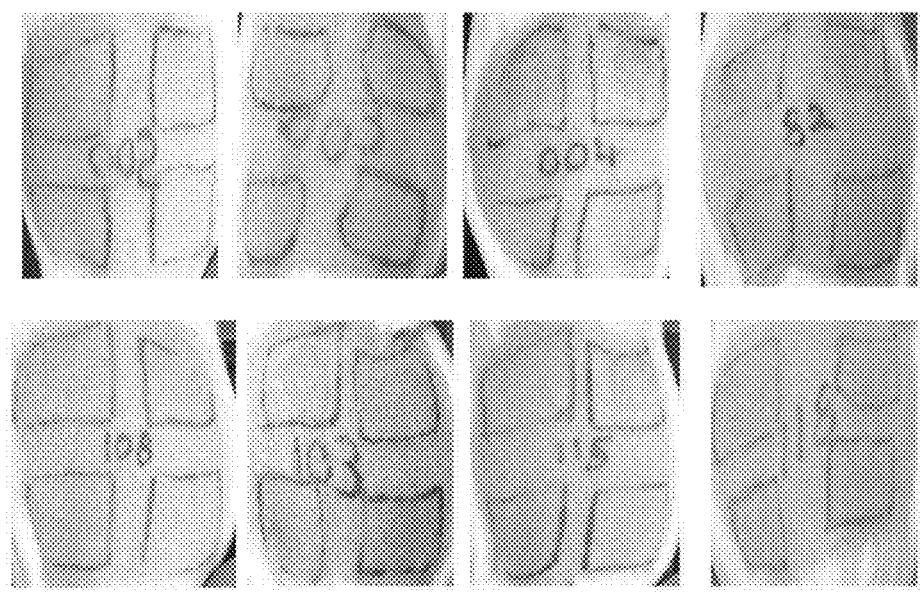
Figure 6. Group IV, Treated with ELI-21-57-3 and then challenged with urushiol (Skin reaction at 72 hrs)

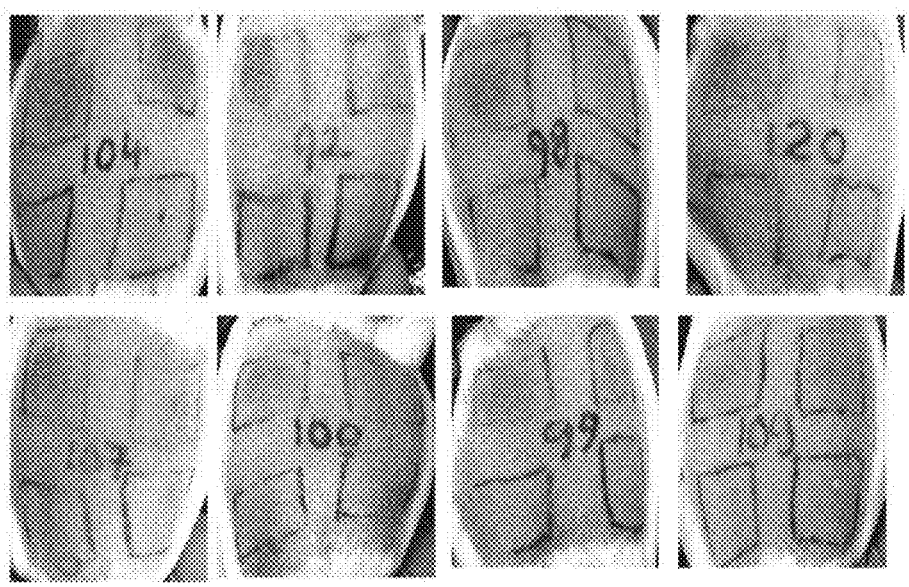
Figure 7. Vehicle treated Group V, challenged with urushiol. (skin reaction at 72 hrs)

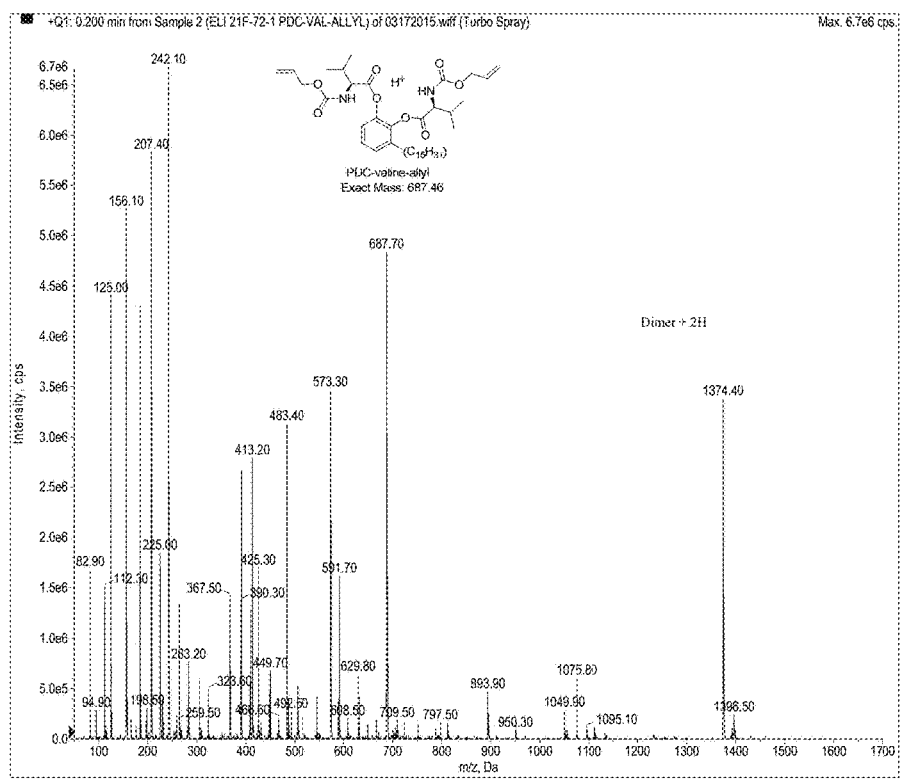
Figure 10. Mass chromatogram of PDC-valininate-allyl

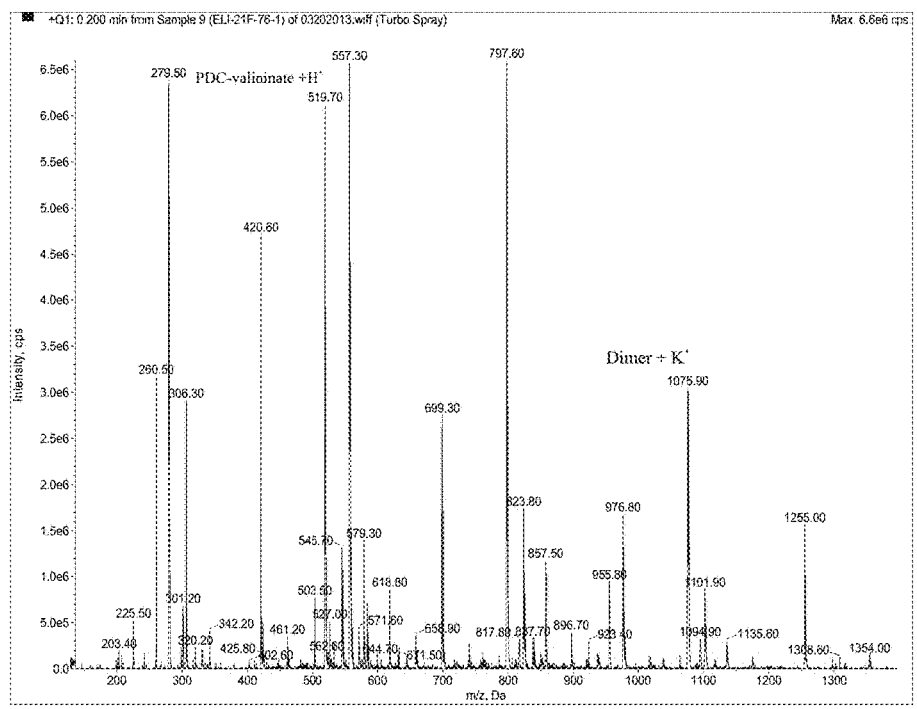
Figure 11. Mass chromatogram of PDC-valininate

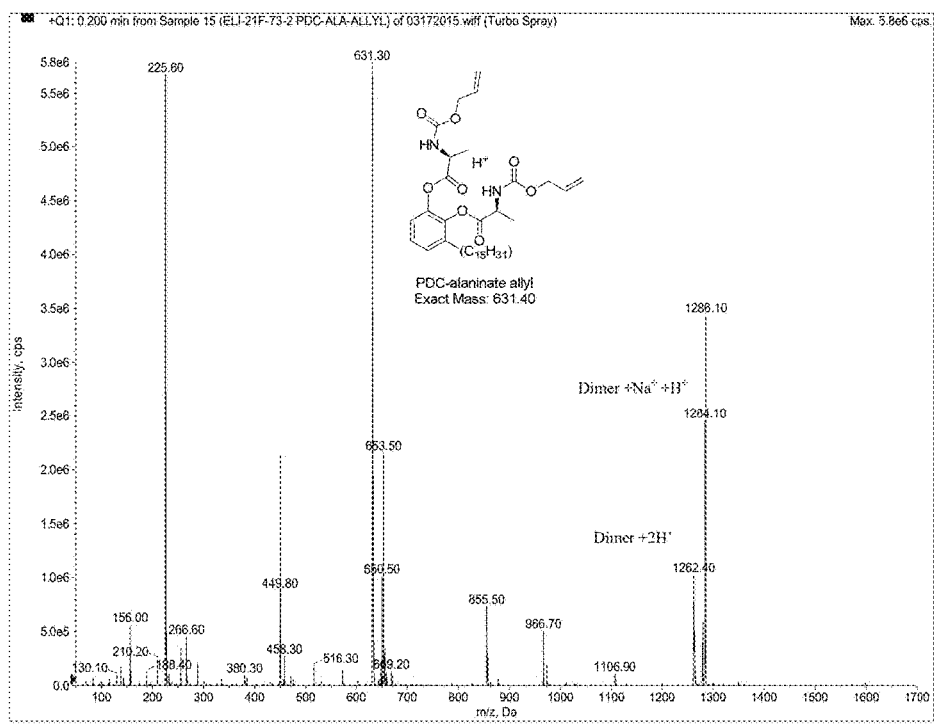
Figure 12. Mass chromatogram of PDC-alaninate-allyl

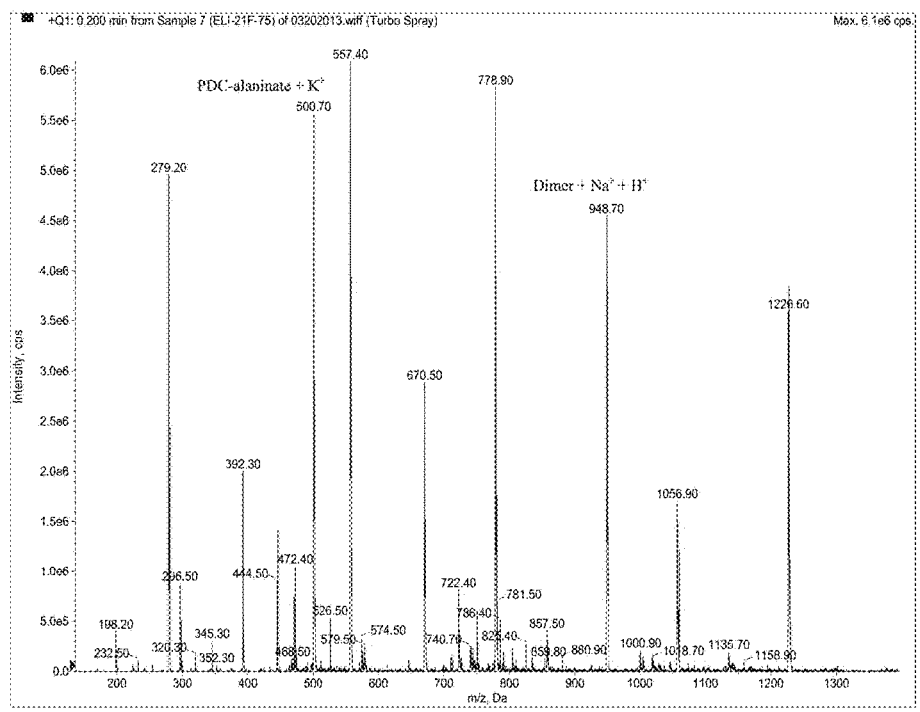
Figure 13. Mass chromatogram of PDC-alaninate

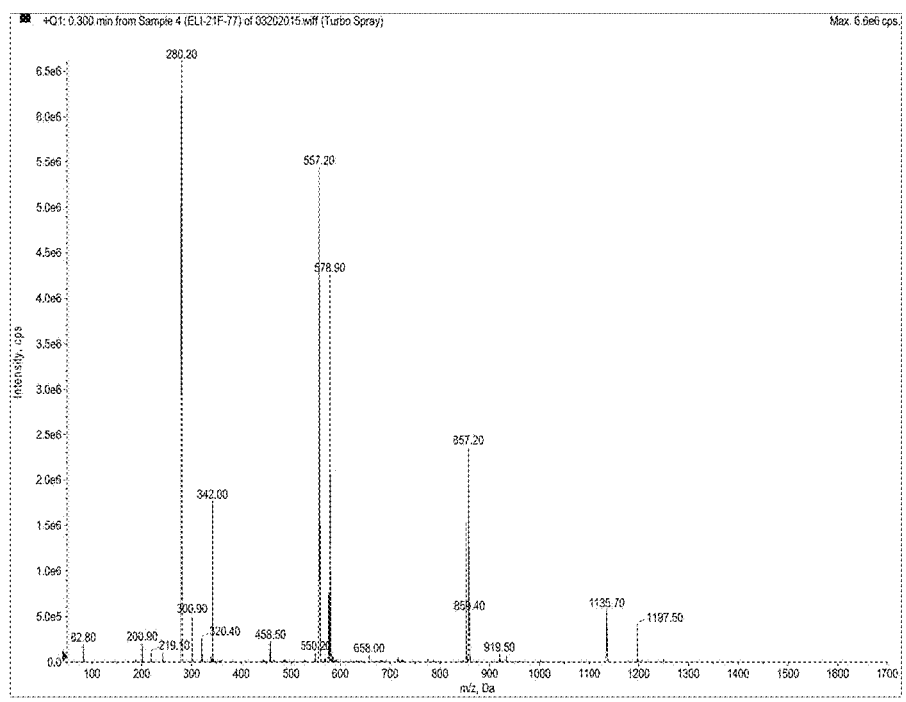
Figure 14. Mass chromatogram of PDC-glutaminate

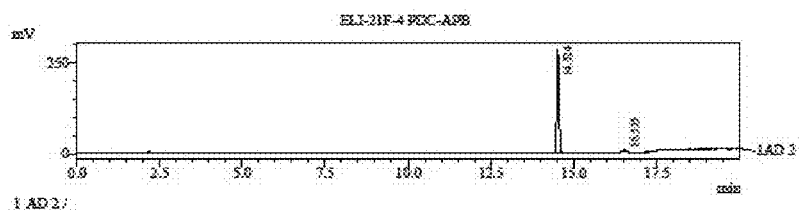
Figure 15. HPLC chromatogram of PDC-APB

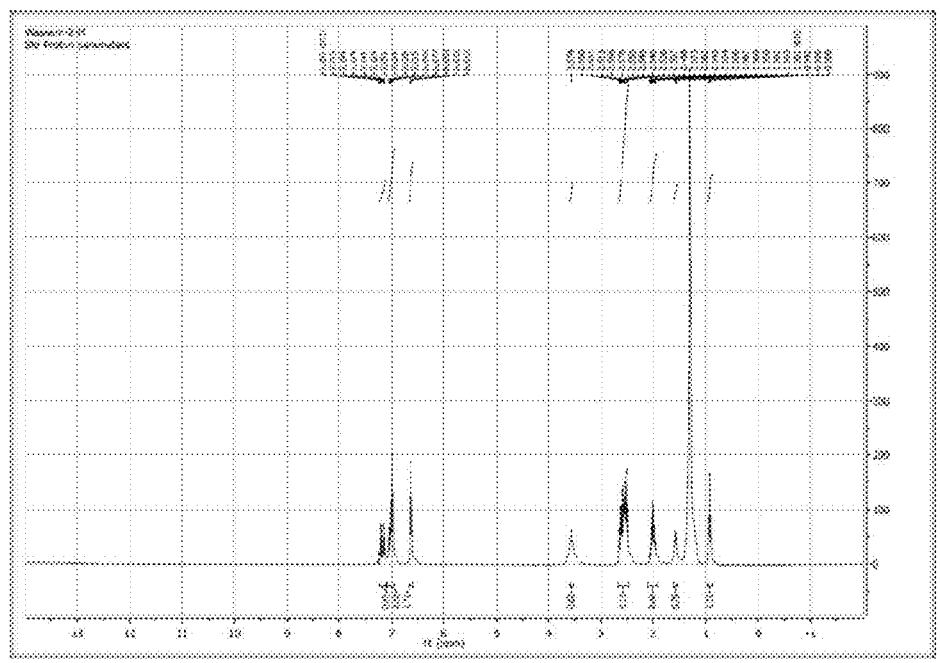
Figure 16. $^1$H-NMR of the PDC-APB in CDCl$_3$ as solvent

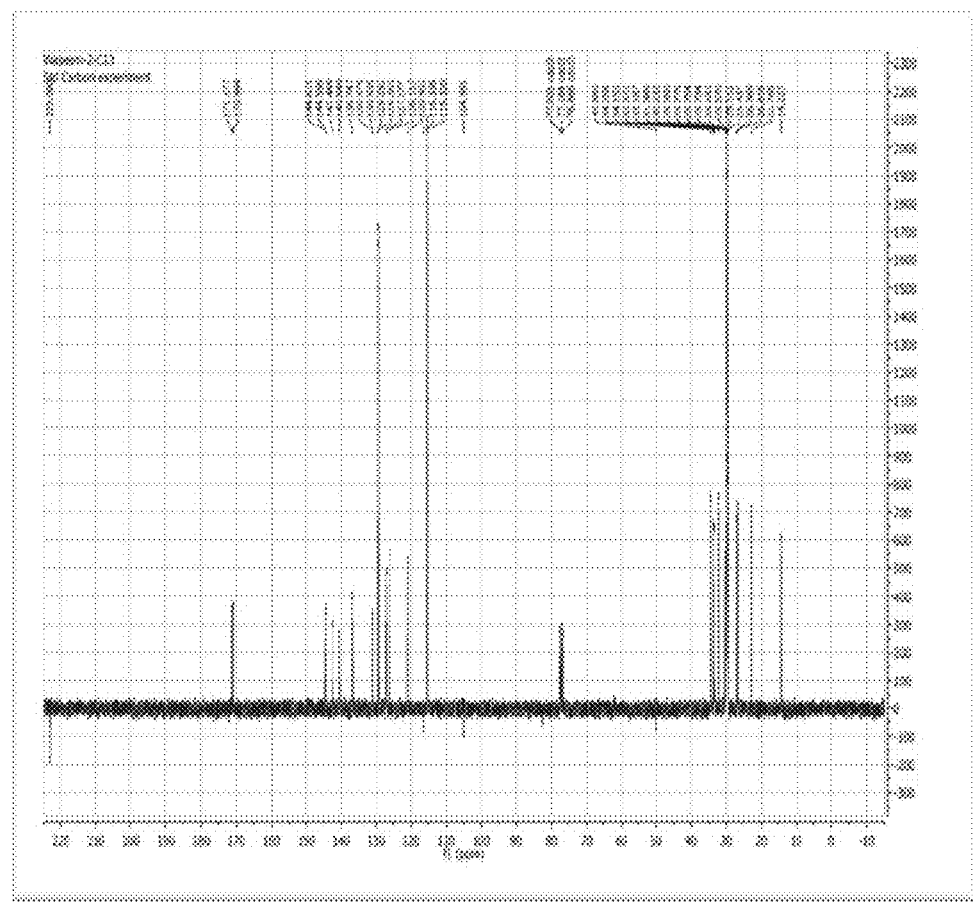
Figure 17. Carbon NMR of the PDC-APB in CDCl$_3$ as solvent

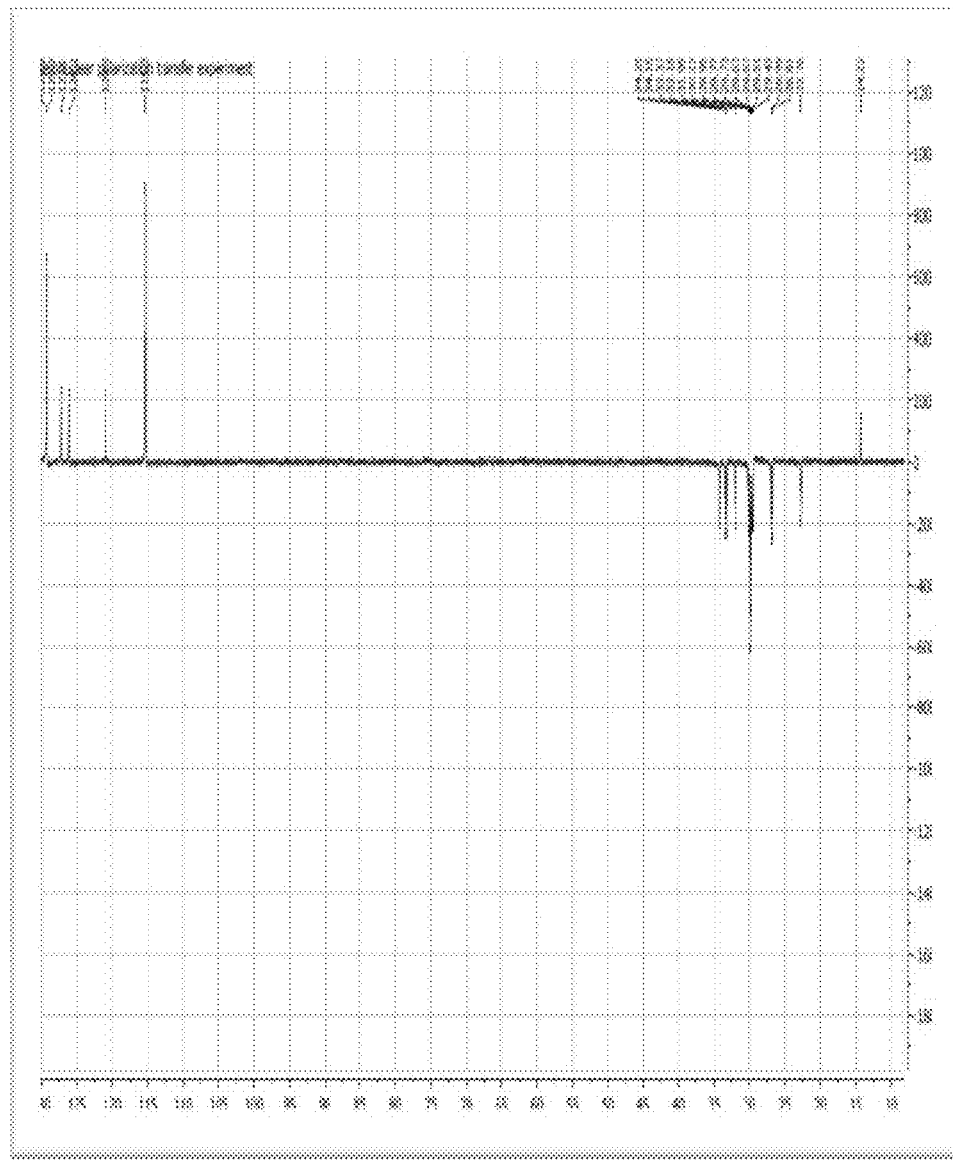
Figure 18. DEPT135 NMR of the PDC-APB in CDCl₃ as solvent

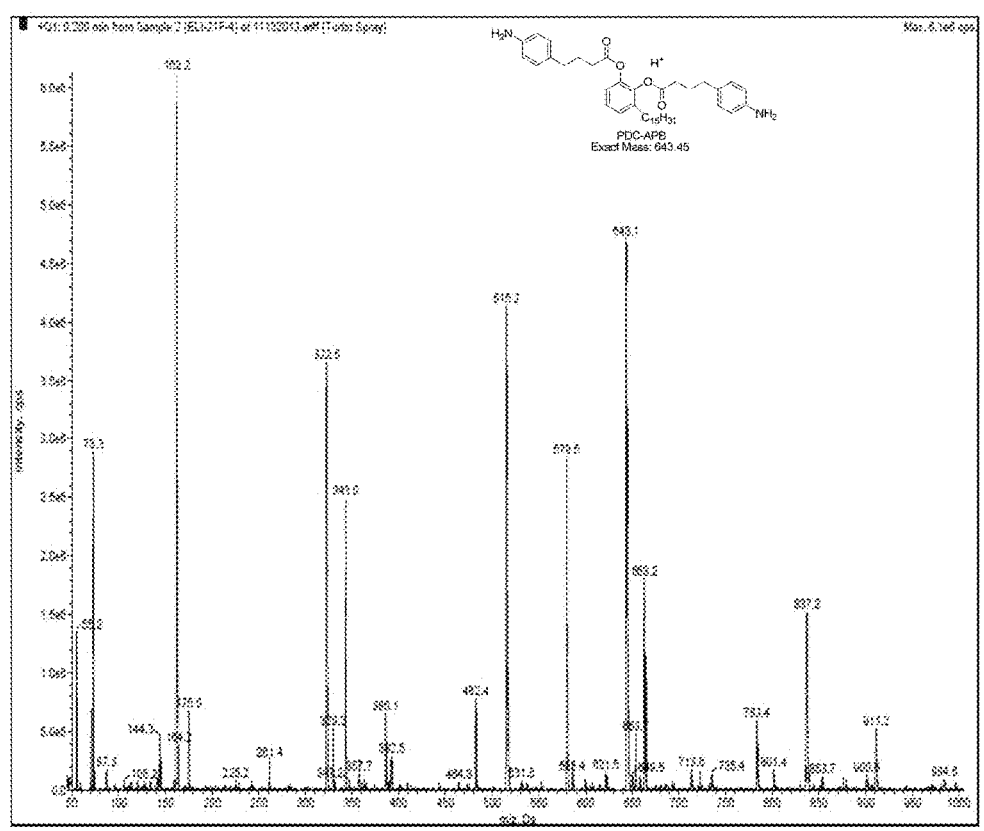
Figure 19. Mass spectrum of the PDC-APB

| | Peak Areas | | | | | |
|---|---|---|---|---|---|---|
| Day | PDC-APB | PDC-APB-APB 1 | PDC-APB-APB 2 | Mono 1 | Mono 2 | PDC |
| 0 | 14319924 | 2122 | 6574 | 5012 | 7904 | |
| 1 | | | | | | |
| 2 | 13148588 | 29330 | 33651 | 16611 | 16633 | 8106 |
| 3 | 11610793 | 36060 | 35968 | 23521 | 16551 | 9460 |
| 4 | 10623240 | 43030 | 48061 | 35038 | 20976 | 13055 |
| 5 | 16013943 | 88038 | 89561 | 58141 | 39724 | 23691 |
| 6 | 15679903 | 108561 | 106093 | 58865 | 46383 | 30487 |

| | Relative Abundance (Based on PDC-APB) | | | | | |
|---|---|---|---|---|---|---|
| Day | PDC-APB | PDC-APB-APB 1 | PDC-APB-APB 2 | Mono 1 | Mono 2 | PDC |
| 0 | 99.849% | 0.015% | 0.046% | 0.035% | 0.055% | 0.000% |
| 1 | | | | | | |
| 2 | 99.207% | 0.223% | 0.256% | 0.126% | 0.127% | 0.062% |
| 3 | 98.953% | 0.311% | 0.310% | 0.203% | 0.143% | 0.081% |
| 4 | 98.492% | 0.405% | 0.452% | 0.330% | 0.197% | 0.123% |
| 5 | 98.132% | 0.550% | 0.559% | 0.363% | 0.248% | 0.148% |
| 6 | 97.765% | 0.692% | 0.677% | 0.375% | 0.296% | 0.194% |

Peak Areas

| Day | PDC-APB | PDC-APB-APB 1 | PDC-APB-APB 2 | Mono 1 | Mono 2 | PDC |
|---|---|---|---|---|---|---|
| 0 | 13322262 | | | 8557 | 4077 | |
| 1 | 13693295 | 14273 | 7573 | 12214 | 9636 | |
| 2 | 11270828 | 19206 | 16685 | 13394 | 13221 | |
| 3 | 10690002 | 30271 | 27314 | 20148 | 14729 | 3289 |
| 4 | 13085110 | 45335 | 43493 | 25723 | 19554 | 6564 |
| 5 | 13924037 | 63167 | 49735 | 34180 | 31109 | 11859 |

Relative Abundance
(Based on PDC-APB)

| Day | PDC-APB | PDC-APB-APB 1 | PDC-APB-APB 2 | Mono 1 | Mono 2 | PDC |
|---|---|---|---|---|---|---|
| 0 | 99.905% | 0.000% | 0.000% | 0.064% | 0.031% | 0.000% |
| 1 | 99.681% | 0.104% | 0.055% | 0.089% | 0.070% | 0.000% |
| 2 | 99.445% | 0.170% | 0.148% | 0.119% | 0.117% | 0.000% |
| 3 | 99.104% | 0.283% | 0.256% | 0.188% | 0.138% | 0.031% |
| 4 | 98.925% | 0.346% | 0.332% | 0.197% | 0.149% | 0.050% |
| 5 | 98.635% | 0.454% | 0.357% | 0.245% | 0.223% | 0.085% |

| Day | PDC-APB | PDC-APB-APB 1 | PDC-APB-APB 2 | Mono 1 | Mono 2 | PDC |
|---|---|---|---|---|---|---|
| 0 | 13509886 | | | 9374 | 2226 | |
| 1 | 13322035 | 15799 | 12412 | 10440 | 8979 | |
| 2 | 7982234 | 16912 | 14063 | 12280 | 7721 | |
| 3 | 8871217 | 21922 | 21168 | 20093 | 12163 | 3630 |
| 4 | 13438924 | 48150 | 52433 | 31281 | 25457 | 10947 |
| 5 | 13697268 | 68706 | 62972 | 37586 | 26737 | 20031 |

Relative Abundance (Based on PDC-APB)

| Day | PDC-APB | PDC-APB-APB 1 | PDC-APB-APB 2 | Mono 1 | Mono 2 | PDC |
|---|---|---|---|---|---|---|
| 0 | 99.914% | 0.000% | 0.000% | 0.069% | 0.016% | 0.000% |
| 1 | 99.642% | 0.119% | 0.093% | 0.078% | 0.067% | 0.000% |
| 2 | 99.361% | 0.212% | 0.176% | 0.154% | 0.097% | 0.000% |
| 3 | 99.110% | 0.247% | 0.239% | 0.226% | 0.137% | 0.041% |
| 4 | 98.748% | 0.358% | 0.390% | 0.233% | 0.189% | 0.081% |
| 5 | 98.423% | 0.502% | 0.460% | 0.274% | 0.195% | 0.146% |

Peak Areas

| Day | PDC-APB | PDC-APB-APB 1 | PDC-APB-APB 2 | Mono 1 | Mono 2 | PDC |
|---|---|---|---|---|---|---|
| 0 | 13460652 | | | 7654 | 4973 | |
| 1 | 12922880 | 12499 | 4585 | 8974 | 9390 | |
| 2 | 12544498 | 13497 | 12826 | 13831 | 13490 | |
| 3 | 5817440 | 9616 | 9658 | 7117 | 8044 | 5016 |
| 4 | 13120394 | 29797 | 27370 | 22097 | 21331 | 13454 |
| 5 | 13466468 | 37903 | 41152 | 24417 | 23292 | 16392 |
| 8 | 10967655 | 52277 | 47929 | 32519 | 23834 | 27518 |
| 9 | 11943933 | 57675 | 59501 | 38471 | 29614 | 31614 |
| 10 | 9086399 | 57728 | 52270 | 31552 | 22870 | 26202 |
| 11 | 9615002 | 61644 | 68169 | 34560 | 28441 | 27994 |
| 12 | 10149834 | 71746 | 77689 | 39417 | 30148 | 36630 |
| 13 | 10271400 | 77975 | 85335 | 43725 | 34235 | 37734 |
| 14 | 10722337 | 95284 | 96708 | 49301 | 38320 | 56079 |
| 17 | 10149123 | 109410 | 125252 | 57354 | 39425 | 82546 |
| 23 | 8277595 | 144531 | 170399 | 76927 | 46905 | 106130 |
| 30 | 13573263 | 434330 | 479970 | 171918 | 141531 | 353887 |

Relative Abundance
(Based on PDC-APB)

| Day | PDC-APB | PDC-APB-APB 1 | PDC-APB-APB 2 | Mono 1 | Mono 2 | PDC |
|---|---|---|---|---|---|---|
| 0 | 99.906% | 0.000% | 0.000% | 0.057% | 0.037% | 0.000% |
| 1 | 99.726% | 0.097% | 0.035% | 0.069% | 0.073% | 0.000% |
| 2 | 99.572% | 0.108% | 0.102% | 0.110% | 0.108% | 0.000% |
| 3 | 99.322% | 0.165% | 0.166% | 0.122% | 0.138% | 0.086% |
| 4 | 99.131% | 0.227% | 0.209% | 0.168% | 0.163% | 0.103% |
| 5 | 98.937% | 0.281% | 0.306% | 0.181% | 0.173% | 0.122% |
| 8 | 98.322% | 0.477% | 0.437% | 0.296% | 0.217% | 0.251% |
| 9 | 98.184% | 0.483% | 0.498% | 0.322% | 0.248% | 0.265% |
| 10 | 97.902% | 0.635% | 0.575% | 0.347% | 0.252% | 0.288% |
| 11 | 97.704% | 0.641% | 0.709% | 0.359% | 0.296% | 0.291% |
| 12 | 97.481% | 0.707% | 0.765% | 0.388% | 0.297% | 0.361% |
| 13 | 97.284% | 0.759% | 0.831% | 0.426% | 0.333% | 0.367% |
| 14 | 96.869% | 0.889% | 0.902% | 0.460% | 0.357% | 0.523% |
| 17 | 95.921% | 1.078% | 1.234% | 0.565% | 0.388% | 0.813% |
| 23 | 93.417% | 1.746% | 2.059% | 0.929% | 0.567% | 1.282% |
| 30 | 88.347% | 3.200% | 3.536% | 1.267% | 1.043% | 2.607% |

5% Ethanol + 10% Benzyl Alcohol in SS Oil (ELI-21F-47-9)

Figure 23A.

Peak Areas

| Day | PDC-APB | PDC-APB-APB 1 | PDC-APB-APB 2 | Mono 1 | Mono 2 | PDC |
|---|---|---|---|---|---|---|
| 0 | 12149540 | | | 8025 | 7789 | |
| 1 | 15304884 | 7273 | 10778 | 12852 | 13660 | |
| 2 | 15458303 | 19085 | 15058 | 18749 | 16413 | 4818 |
| 3 | 4802437 | 8065 | 7752 | 7583 | 6433 | 1621 |
| 4 | 14559096 | 35886 | 32845 | 23154 | 21920 | 9501 |
| 5 | 14543597 | 36377 | 39080 | 27750 | 30346 | 10573 |
| 8 | 11875991 | 52700 | 53294 | 31112 | 27505 | 17570 |
| 9 | 13974036 | 66905 | 75429 | 44439 | 35735 | 30929 |
| 10 | 8585236 | 42617 | 54570 | 30907 | 23369 | 21018 |
| 11 | 12197897 | 74769 | 84775 | 49624 | 34581 | 37481 |
| 12 | 12597653 | 79111 | 88065 | 52002 | 38840 | 43743 |
| 13 | 11519839 | 84872 | 85354 | 53050 | 35682 | 42742 |
| 14 | 12334189 | 98100 | 106672 | 59695 | 42492 | 61965 |
| 17 | 12117570 | 117242 | 137204 | 68177 | 44208 | 61058 |
| 23 | 8015497 | 130812 | 149230 | 72693 | 45685 | 83352 |
| 30 | 13391293 | 411876 | 452978 | 208434 | 140508 | 313976 |

Relative Abundance
(Based on PDC-APB)

| Day | PDC-APB | PDC-APB-APB 1 | PDC-APB-APB 2 | Mono 1 | Mono 2 | PDC |
|---|---|---|---|---|---|---|
| 0 | 99.870% | 0.000% | 0.000% | 0.066% | 0.064% | 0.000% |
| 1 | 99.709% | 0.048% | 0.070% | 0.084% | 0.089% | 0.000% |
| 2 | 99.520% | 0.123% | 0.097% | 0.121% | 0.106% | 0.031% |
| 3 | 99.345% | 0.168% | 0.161% | 0.158% | 0.134% | 0.034% |
| 4 | 99.153% | 0.246% | 0.226% | 0.159% | 0.151% | 0.065% |
| 5 | 99.009% | 0.250% | 0.269% | 0.191% | 0.209% | 0.073% |
| 8 | 98.466% | 0.444% | 0.449% | 0.262% | 0.232% | 0.148% |
| 9 | 98.186% | 0.479% | 0.540% | 0.318% | 0.256% | 0.221% |
| 10 | 97.991% | 0.496% | 0.636% | 0.360% | 0.272% | 0.245% |
| 11 | 97.694% | 0.613% | 0.695% | 0.407% | 0.283% | 0.307% |
| 12 | 97.605% | 0.628% | 0.699% | 0.413% | 0.308% | 0.347% |
| 13 | 97.381% | 0.737% | 0.741% | 0.461% | 0.310% | 0.371% |
| 14 | 97.009% | 0.795% | 0.865% | 0.484% | 0.345% | 0.502% |
| 17 | 96.469% | 0.968% | 1.132% | 0.563% | 0.365% | 0.504% |
| 23 | 93.989% | 1.632% | 1.862% | 0.907% | 0.570% | 1.040% |
| 30 | 88.591% | 3.076% | 3.383% | 1.556% | 1.049% | 2.345% |

10% Ethanol + 10% Benzyl Alcohol in SS Oil (ELI-21F-47-10)

Fig. 24A

Peak Areas

| Day | PDC-APB | PDC-APB-APB 1 | PDC-APB-APB 2 | Mono 1 | Mono 2 | PDC |
|---|---|---|---|---|---|---|
| 0 | 13313589 | | | 6991 | 15320 | |
| 1 | 12556421 | 178267 | 188134 | 126091 | 62854 | 8266 |
| 2 | 8003268 | 240765 | 259600 | 145642 | 83701 | 13366 |

Relative Abundance
(Based on PDC-APB)

| Day | PDC-APB | PDC-APB-APB 1 | PDC-APB-APB 2 | Mono 1 | Mono 2 | PDC |
|---|---|---|---|---|---|---|
| 0 | 99.832% | 0.000% | 0.000% | 0.053% | 0.115% | 0.000% |
| 1 | 95.511% | 1.420% | 1.498% | 1.004% | 0.501% | 0.066% |
| 2 | 90.715% | 3.008% | 3.244% | 1.820% | 1.046% | 0.167% |

| Day | PDC-APB | PDC-APB-APB 1 | Mono 2 | PDC |
|---|---|---|---|---|
| 0 | 13688526 | | 13904 | |
| 1 | 13193471 | 132425 | 46880 | |
| 2 | 5089728 | 103141 | 38145 | 3339 |

Relative Abundance
(Based on PDC-APB)

| Day | PDC-APB | PDC-APB-APB 1 | PDC-APB-APB 2 | Mono 1 | Mono 2 | PDC |
|---|---|---|---|---|---|---|
| 0 | 99.846% | 0.000% | 0.000% | 0.052% | 0.102% | 0.000% |
| 1 | 96.960% | 1.004% | 1.096% | 0.585% | 0.355% | 0.000% |
| 2 | 93.612% | 2.026% | 2.258% | 1.288% | 0.749% | 0.066% |

| Day | PDC-APB | PDC-APB-APB 1 | PDC-APB-APB 2 | Mono 1 | Mono 2 | PDC |
|---|---|---|---|---|---|---|
| 0 | 13429563 | | | 11794 | | |
| 1 | 13949693 | | | 13877 | | |
| 2 | 13537876 | | | 15532 | 12142 | |
| 3 | 14019892 | | | 24536 | 13078 | |
| 4 | 13473060 | 5668 | 8485 | 32828 | 15697 | 3252 |
| 5 | 12115807 | 12654 | 9338 | 44249 | 20914 | 4619 |
| 6 | 11926241 | 14487 | 10731 | 80469 | 31914 | 4483 |
| 7 | 13426566 | 18166 | 22908 | 144225 | 49938 | 13760 |
| 10 | 13577050 | 32401 | 32633 | 177582 | 58736 | 35594 |
| 16 | 12739689 | 53059 | 50247 | 150482 | 51278 | 52542 |
| 23 | 13453832 | 84290 | 86041 | 149319 | 53374 | 65569 |
| 30 | 12104953 | 102821 | 105889 | 117665 | 56466 | 71756 |
| 43 | 10520382 | 138998 | 140801 | 133194 | 82848 | 105200 |

Relative Abundance
(Based on PDC-APB)

| Day | PDC-APB | PDC-APB-APB 1 | PDC-APB-APB 2 | Mono 1 | Mono 2 | PDC |
|---|---|---|---|---|---|---|
| 0 | 99.912% | 0.000% | 0.000% | 0.088% | 0.000% | 0.000% |
| 1 | 99.901% | 0.000% | 0.000% | 0.099% | 0.000% | 0.000% |
| 2 | 99.796% | 0.000% | 0.000% | 0.115% | 0.090% | 0.000% |
| 3 | 99.732% | 0.000% | 0.000% | 0.175% | 0.093% | 0.000% |
| 4 | 99.511% | 0.042% | 0.063% | 0.244% | 0.117% | 0.024% |
| 5 | 99.243% | 0.104% | 0.077% | 0.365% | 0.173% | 0.038% |
| 6 | 98.809% | 0.121% | 0.090% | 0.675% | 0.268% | 0.038% |
| 7 | 98.145% | 0.135% | 0.171% | 1.074% | 0.372% | 0.102% |
| 10 | 97.518% | 0.239% | 0.240% | 1.308% | 0.433% | 0.262% |
| 16 | 97.193% | 0.416% | 0.394% | 1.181% | 0.403% | 0.412% |
| 23 | 96.740% | 0.627% | 0.640% | 1.110% | 0.397% | 0.487% |
| 30 | 96.245% | 0.849% | 0.875% | 0.972% | 0.466% | 0.593% |
| 43 | 94.287% | 1.321% | 1.338% | 1.266% | 0.787% | 1.000% |

Figure 27A. 8% Ethanol + 2% Benzyl Alcohol in SS Oil (ELI-21F-52-2)

| Day | PDC-APB | PDC-APB-APB 1 | PDC-APB-APB 2 | Mono 1 | Mono 2 | PDC |
|---|---|---|---|---|---|---|
| 0 | 11982906 | | | 3372 | | |
| 1 | 10140316 | 9416 | 5248 | 8433 | 11692 | |
| 2 | 13062609 | 20077 | 20035 | 16487 | 18581 | |
| 3 | 10949557 | 22562 | 23331 | 18110 | 17911 | |
| 4 | 11654942 | 33097 | 31540 | 24470 | 20636 | 5643 |
| 5 | 12066639 | 45198 | 40655 | 34480 | 29763 | 7988 |
| 6 | 10252340 | 43470 | 49068 | 31902 | 28178 | 11635 |
| 7 | 10080383 | 50381 | 58811 | 34613 | 29649 | 11763 |
| 10 | 7865664 | 56066 | 65815 | 31245 | 26839 | 9794 |
| 16 | 10228592 | 135587 | 140373 | 67101 | 45231 | 29581 |
| 23 | 9333447 | 197790 | 220756 | 89305 | 54608 | 62236 |
| 30 | 5140257 | 155796 | 172135 | 64143 | 37147 | 57468 |
| 43 | 4727567 | 305956 | 318101 | 116285 | 79630 | 181225 |

Relative Abundance
(Based on PDC-APB)

| Day | PDC-APB | PDC-APB-APB 1 | PDC-APB-APB 2 | Mono 1 | Mono 2 | PDC |
|---|---|---|---|---|---|---|
| 0 | 99.972% | 0.000% | 0.000% | 0.028% | 0.000% | 0.000% |
| 1 | 99.657% | 0.093% | 0.052% | 0.083% | 0.115% | 0.000% |
| 2 | 99.424% | 0.154% | 0.153% | 0.126% | 0.142% | 0.000% |
| 3 | 99.252% | 0.206% | 0.213% | 0.165% | 0.164% | 0.000% |
| 4 | 99.010% | 0.284% | 0.271% | 0.210% | 0.177% | 0.048% |
| 5 | 98.690% | 0.375% | 0.337% | 0.286% | 0.247% | 0.066% |
| 6 | 98.398% | 0.424% | 0.479% | 0.311% | 0.275% | 0.113% |
| 7 | 98.163% | 0.500% | 0.583% | 0.343% | 0.294% | 0.117% |
| 10 | 97.588% | 0.713% | 0.837% | 0.397% | 0.341% | 0.125% |
| 16 | 95.915% | 1.326% | 1.372% | 0.656% | 0.442% | 0.289% |
| 23 | 93.307% | 2.119% | 2.365% | 0.957% | 0.585% | 0.667% |
| 30 | 90.532% | 3.031% | 3.349% | 1.248% | 0.723% | 1.118% |
| 43 | 78.822% | 6.472% | 6.729% | 2.460% | 1.684% | 3.833% |

Figure 28A. 10% Ethanol + 2% Benzyl Alcohol in SS Oil (ELI-21F-53-2)

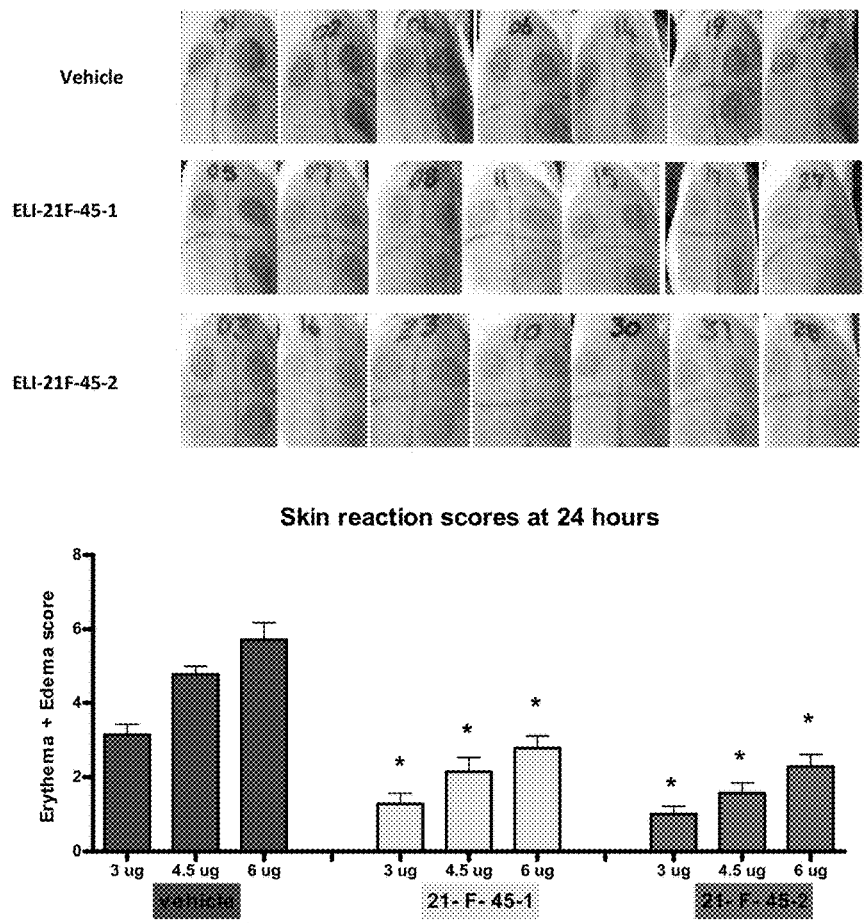
Figure 29A. Skin reaction and score at 24 hours post challenge #1
*p<0.05 as compared to vehicle

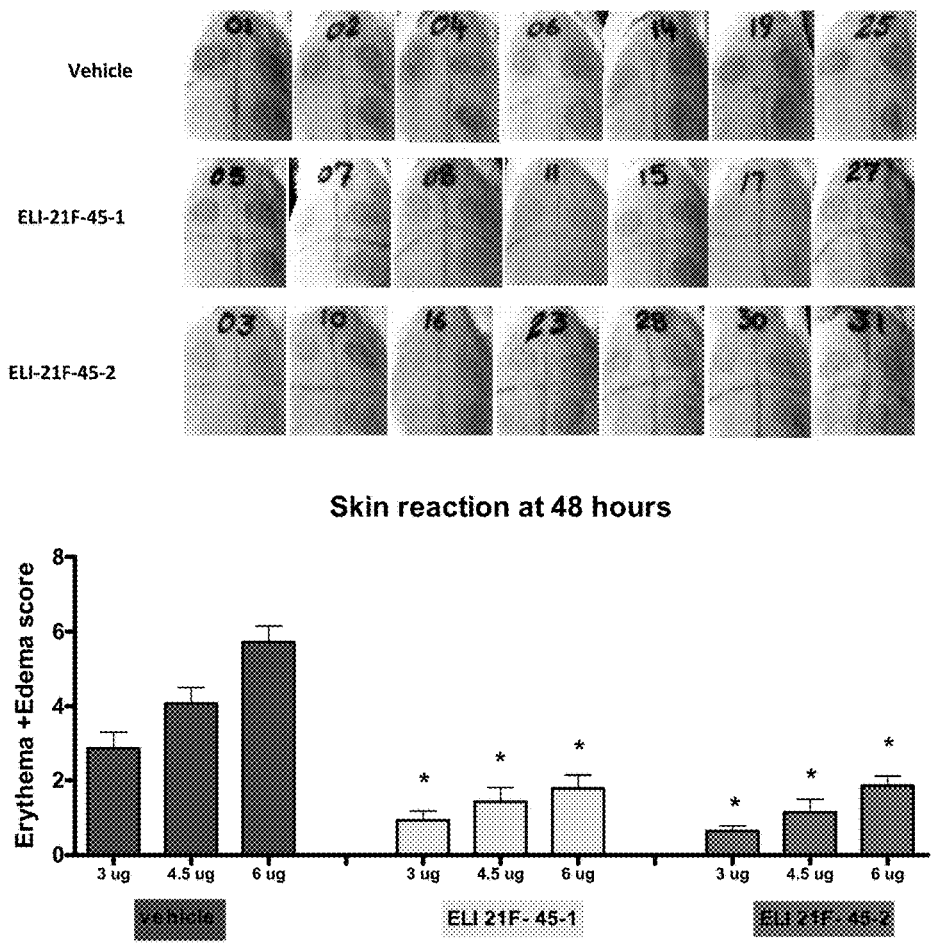
Figure 29B. Skin reaction and score at 48 hours post challenge #1
*p<0.05 as compared to vehicle

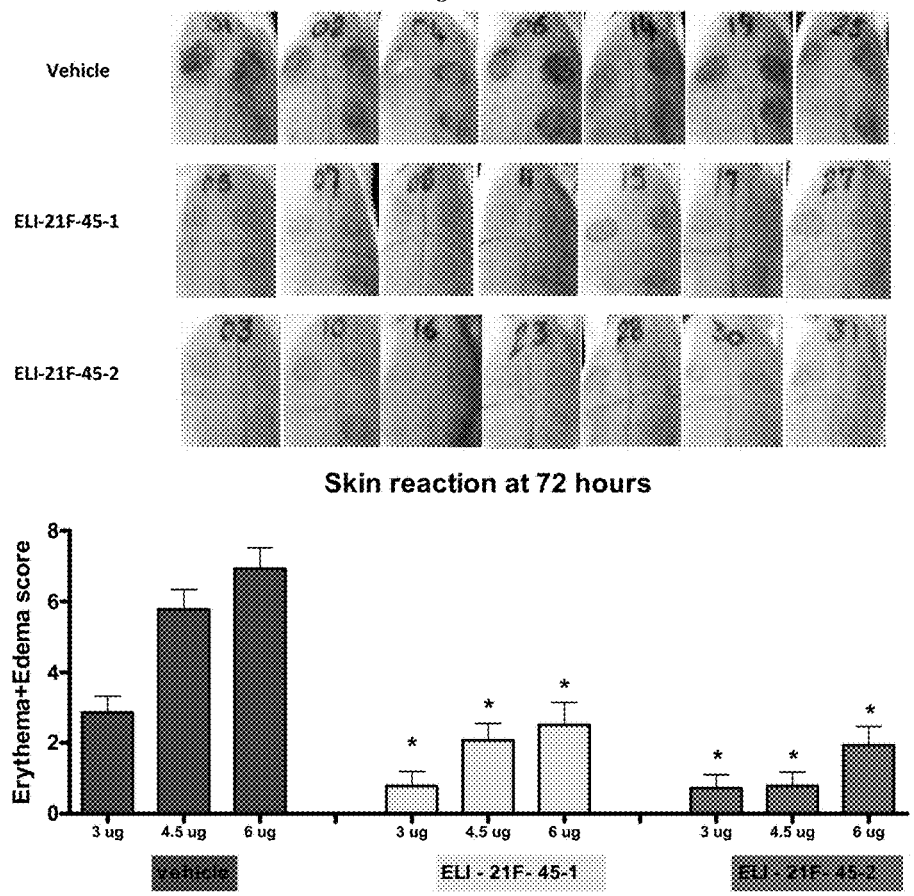
Figure 29C. Skin reaction and score at 72 hours post challenge #1
*p<0.05 as compared to vehicle

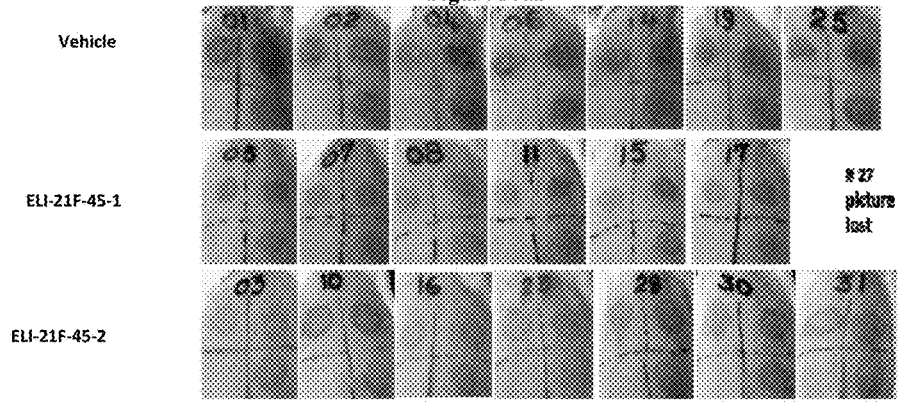
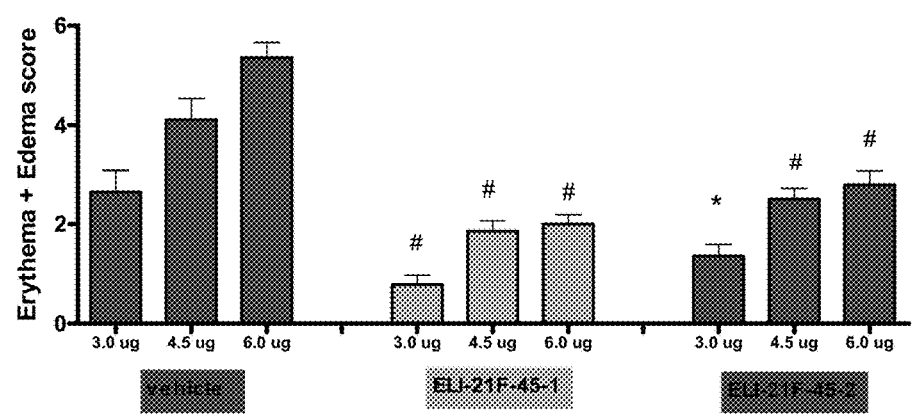
Figure 30A. Skin reaction and score at 24 hours post challenge #2
*p<0.05; #p<0.01 as compared to vehicle

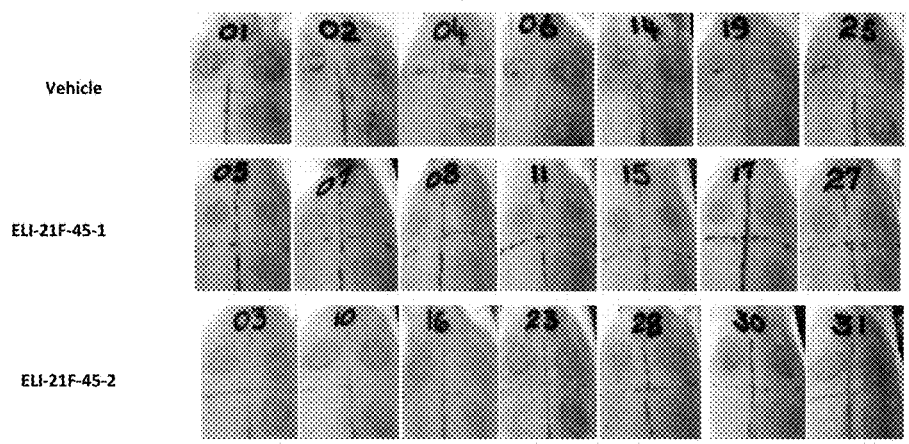
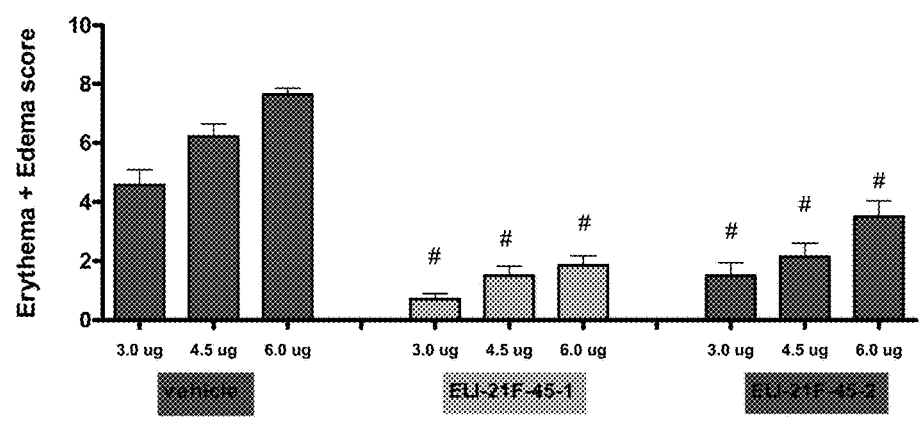
Figure 30B. Skin reaction and score at 48 hours post challenge #2
p<0.05 as compared to vehicle

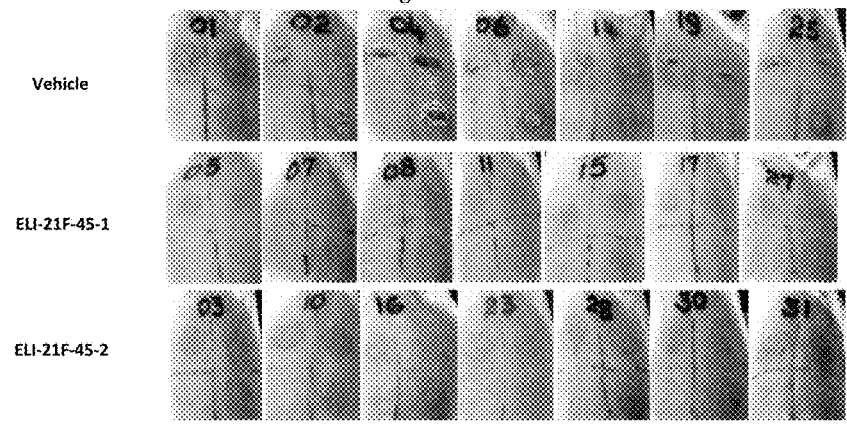
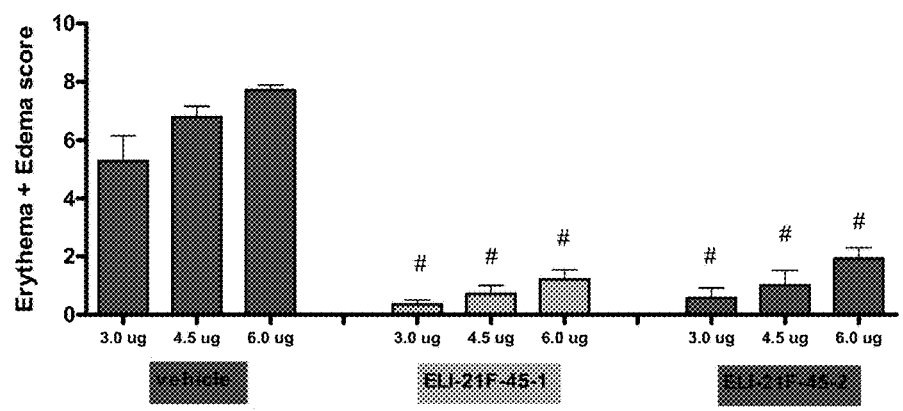
Figure 30C. Skin reaction and score at 72 hours post challenge #2
p<0.01 as compared to vehicle

COMPOSITIONS FOR PREVENTION/PROPHYLACTIC TREATMENT OF POISON IVY DERMATITIS

CROSS-REFERENCE TO RELATED APPLICATIONS

This is a Continuation-In-Part of U.S. application Ser. No. 14/675,773 filed Apr. 1, 2015, which is a Division of U.S. application Ser. No. 13/860,861 filed Dec. 14, 2010 and issued May 12, 2015 as U.S. Pat. No. 9,029,417, which is a Division of U.S. application Ser. No. 12/936,204 filed Dec. 14, 2012 and issued Jul. 16, 2013 as U.S. Pat. No. 8,486,998, which is a § 371 US National Stage of PCT/US09/39472 filed Apr. 3, 2009, which claims priority of U.S. Provisional Application No. 61/042,118 filed Apr. 3, 2008, now expired, the disclosures of all of which are incorporated herein in their entireties by reference.

FIELD OF THE INVENTION

The present invention relates generally to compositions and formulations for the prevention and/or prophylactic treatment of poison ivy dermatitis, methods of using such compositions, and methods of making such compositions.

BACKGROUND OF THE INVENTION

Poison ivy (*Toxicodendron radicans*), poison oak (*T. diversilobum*), and poison sumac (*T. vernix*) affects 10-50 million Americans every year (1) and is the primary cause of occupational dermatitis in the United States (2). The prevalence of poison ivy and poison oak sensitivity in the general adult population ranges from 50% to 70% (3, 4). Peak frequency for sensitization occurs between ages 8-14 (5). Genetic susceptibility to urushiol sensitivity suggested that 80% of children who are born to two urushiol sensitive parents will become sensitive (6). Outdoor activities as well as outdoor occupations that relate to firefighting, forestry and agriculture are at high risk, costing significant medical expenses and worker's disability. Each fire season, approximately one third of forestry workers in California, Oregon and Washington are disabled by poison oak dermatitis (7). This disorder is very well known to most emergency and primary care physicians and dermatologists (8).

Other genera of the plant family Anacardiaceae with dermatogenic constituents include *Anacardium* (cashew nuts), *Semicarpus* (India ink tree), *Metopium* (poison wood), and *Mangifera* (mango). The allergenic components in most of these plants are 3-n-alk-(en)-yl catechols with C-15 or C-17 side chains and different degrees of unsaturation (0-3 olefinic bonds) (9-12). Urushiol is typical of such allergenic components present in poison ivy, poison oak, and the Asian lacquer tree (13). It has a catechol ring substituted with a C15 or C17 hydrocarbon chain at the 3 or 4 position, either saturated or having one, two or three unsaturated bonds (14). Both the catecholic ring and the aliphatic chain are proven to play important roles in allergenicity of urushiols (15-17). Contact of these catechols with the skin of susceptible individuals results in sensitization to all urushiols of the plant family Anacardiaceae (18). Once sensitivity is developed, it is difficult, if not impossible, to eliminate.

Allergic contact dermatitis (ACD) results from direct skin contact with a substance that the body recognizes as foreign. The resulting skin inflammation is a dendritic cell dependent delayed-hypersensitivity immunologic reaction. It occurs more commonly on thin-skin surfaces such as eyelids and genital skin. This type of response is elicited by cutaneous exposure to a variety of compounds that may act as haptens. These haptens become immunogenic after binding to discrete amino acid residues of proteins or peptides. The clinical manifestation is preceded by a sensitization phase, which is clinically silent. Rodent models of contact hypersensitivity have contributed towards understanding of mechanisms of ACD. It is known that during sensitization, dendritic cells (DCs) that have taken up an allergen/hapten (in this case urushiol) migrate to draining lymph nodes (LNs) where they mature, express co-stimulatory molecules, and present antigens to naive T cells (19-20). The mature DCs as well as the naive T cells are attracted to the LNs by chemokines that are expressed in the LNs (19, 21).

When a sensitized person is exposed to the hapten/urushiol, specific T cells (CD8+ and CD4+) migrate under the influence of chemokines to the site of exposure on the skin where the cells undergo extensive proliferation (19). The activated T cells subsequently produce and release high levels of cytokines, thereby causing an inflammatory process leading to inflammation and/or edema. It has been suggested that CD8+ cytotoxic lymphocytes are the main effector cells responsible for the manifestation of ACD. These cells are recruited early after challenge. CD4+ T cell subsets are the down regulatory cells and are visible in the skin lesions after 72 hrs in the recovery phase of ACD (22). The percutaneous absorption of urushiol is similar to that of other lipophilic substances. These molecules preferentially enter the skin through the intercellular lipids of the stratum corneum. Any substance that blocks the contact of urushiol with the stratum corneum and prevents its entry, also known as barrier products, would likely offer some protection. Many commercial products have been developed and tested for their effectiveness in preventing urushiol dermatitis, and these experiments have been published (1, 23-28). Presently, only a few substances offer some realistic benefits (1, 23, 24).

One product (an organoclay, quanterium-18 bentonite) was tested by Epstein (23) in a pilot study and was found to be more effective than bentonite, kaolin or silicone in preventing experimental urushiol dermatitis. In 1992, Grevelink et al., (24) published the best contemporary review concerning the effectiveness of barrier products. They also compared the efficacy of seven commercial products in preventing experimental urushiol dermatitis in twenty volunteers using a 9-point global severity score. Stokogard (Stockhausen, Greenboro, N.C.), Hollister Moisture Barrier (Hollister, Inc., Libertyville, Ill.), and Hydropel (C&M Pharmacol, Inc., Hazel Park, Mich.) offered a substantial degree of protection. These products provided 59%, 53%, and 48% protection, respectively. Ivy Shield (Interpro, Inc., Haverhill, Mass.), Shield Skin (Mantor Corp., Minneapolis, Minn.), Dermofilm (Innovetec, Brussels, Belgium), and Uniderm (Smith and Nephew, Inc., Largo, Fla.) provided much lower (if any) levels of protection at 22%, 13%, 3%, and 9%, respectively (24). Topical Skin Protectant (TSP), another skin barrier product, is composed of polytetrafluoroethylene (PTFE) resins mixed in perfluorinated polyether oil (29). Vidmar and Iwane reported that TSP completely prevented dermatitis altogether in 34 of the 192 paired test sites and attenuated it to only trace levels in 22 paired sites (29).

Treatment for dermatitis is primarily symptomatic. For patients with severe cases, a tapering dose of oral corticosteroids such as prednisone may be used. Prednisone is a corticosteroid hormone (glucocorticoid) which decreases the immune system's response to various diseases to reduce symptoms such as swelling and allergic-type reactions. However, available "dosepacks" of corticosteroids are of little use since they deliver small doses of corticosteroid for too short a period of time and often result in a rebound reaction (30).

The remaining treatments for Poison Ivy related ACD are centered around palliative care. Benadryl topical cream (Pfizer) dries the oozing and weeping of poison ivy, poison oak, and poison sumac and temporarily relieves the pain and itching.

There have been multiple desensitization regimens (elimination of sensitivity of sensitized individuals) utilized since the 1950s containing extracts of poison ivy/oak yet none are reliably effective (31, 32). The techniques consisted of ingestion or parenteral injection of various formulations of urushiol. Although some reports have described success (31, 32), the levels of desensitization were variable and not durable. In addition, the regimens produced mucous membrane, cutaneous, and systemic side effects. Accordingly, this approach has been largely abandoned.

Hyposensitization (reduction of the degree of sensitivity of sensitized individuals; tolerized) by administration of plant extracts is difficult to obtain. It requires large doses and months or years to be produced, and sensitivity is rapidly regained upon cessation of treatment (18, 31). The benefits and safety of the use of *Rhus* extracts (containing the active allergenic ingredient urushiols) for this purpose have been topics of dispute since they were first administered in 1917. Several reviews pertaining to the clinical use of *Rhus* extracts and allergens have been written (23, 33, 34).

The reason for the lack of activity of administered urushiols in the free form might be due to the high reactivity of the catechol moiety of the urushiols with plasma proteins. Putatively, once absorbed, the urushiols bind irreversibly with the proteins and become "deactivated". We have rationalized that it might be necessary for the urushiols to bind to cell membranes to be effective in the production of tolerance or the prophylactic treatment of poison ivy dermatitis. Taking this into account, we previously prepared a conjugate of poison ivy urushiol bound to cell membranes by spiking the urushiol solution into a suspension of blood cell membranes from lyzed and washed blood cells and then reinjected the suspension into donor animals (18). We have shown (18) that tolerance was produced by the administration of 3-n-pentadecylcatechol (the saturated congener of poison ivy urushiol) coupled to red blood cell membranes in guinea pigs. The treated group was tolerant to 3-n-pentadecylcatechol for the 20 weeks of the study.

Having succeeded in that approach, we theorized that administration of a urushiol ester might be more effective in that some of the ester could hydrolyze at the surface of the blood cells, thereby resulting in free urushiol which could bind to the membrane. Administration of a urushiol ester can be through for example subcutaneous injection ("s.c."), intramuscular injection ("IM"), intravenous injection ("IV"), intranasal administration, transmucosal administration and rectal administration. Tolerance to poison ivy urushiol in the guinea pig model was accomplished by IV injection of the diacetate esters of poison ivy and oak urushiols in naïve guinea pigs and complete desensitization or hyposensitization was accomplished in sensitized animals by the same treatment (35). The efficacy of oral administration of poison ivy and poison oak urushiols was compared with the use of the respective esterified derivatives for desensitizing sensitive guinea pigs (36). The esterified derivatives produced a greater degree of hyposensitization than was produced by the free urushiols and the hyposensitization was of longer duration. We have concluded that for the urushiol esters to be most effective, parental administration is necessary. We, therefore, conducted a study to evaluate the potential for a single-dose regimen to be effective for hyposensitization to poison ivy urushiol dermatitis (37). Hyposensitization was accomplished in a single intramuscular dose of 20 mg.

The mechanism of action for the prophylactic treatment of poison ivy/oak dermatitis using urushiols is not known but may involve the up-regulation of CD4+ T cell proliferation with concomitant downregulation of CD8+ T cells.

SUMMARY OF INVENTION

The present invention, in one or more embodiments, comprises derivatives of poison ivy urushiol or 3-n-pentadecylcatechol (poison ivy urushiol saturated congener) and/or poison oak urushiol or 3-n-heptadecylcatechol (poison oak urushiol saturated congener) as potential compositions for the prevention and/or prophylactic treatment of contact dermatitis caused by poison ivy and poison oak and other ACD causing plants of the family Anacardiaceae and Ginkgoaceae. Further, the present invention is directed towards processes for making such compounds. In particular, there are disclosed compounds which are effective for tolerizing and desensitizing against contact dermatitis caused by allergens contained in plants of the Anacardiaceae and Ginkgoaceae families comprising urushiol esters of the general formula (I)

(I)

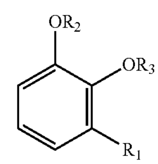

wherein $R_1$ is an alkyl radical having 11 to 19 carbon atoms, or an unsaturated congener thereof; or mixtures thereof; and $R_2$ and $R_3$ are each independently the residue radicals derived from an amino acid or combination of amino acids (i.e. di, tri, or poly peptide residue), a carbamate forming compound or a sulfate or phosphate ester or an ester of a dicarboxylic acid. Suitable substituent groups include compounds in which $R_1$ is pentadecyl, heptadecyl, nonadecyl, mono-olefinic pentadecyl, mono-olefinic heptadecyl, diolefinic pentadecyl, diolefinic heptadecyl, triolefinic pentadecyl and triolefinic heptadecyl.

The present invention is also directed towards a method of tolerizing and desensitizing mammals, including humans, to allergens contained in plants of the Anacardiaceae and Ginkgoaceae families which consists essentially of administering to said mammal a composition comprising a compound or mixture of compounds as disclosed in the present invention. In the context of this application, desensitization is meant to encompass elimination of sensitivity in a sensitized subject as well as a reduction in the degree of sensitivity of a sensitized subject (hyposensitization or tolerization). Also disclosed are methods of preparing the compositions of this invention.

Summary of Free Base and Free Base Formulation

The present invention relates to urushiol esters which are effective for desensitizing a subject against contact dermatitis caused by allergens contained in plants of the Anacardiaceae and Ginkgoaceae families. These esters have the following formula (IA)

(IA)

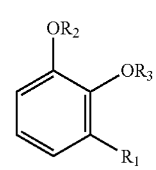

wherein $R_1$ is an alkyl radical having 11 to 19 carbon atoms, or an unsaturated analog or congener thereof; or mixtures thereof; and $R_2$ and $R_3$ are each independently a radical derived from an amino acid or a combination of amino acids or from a dicarboxylic acid or dicarboxylic acid derivative. Excluded from the present invention is that, when $R_1$ is heptadecyl or pentadecyl, $R_2$ and $R_3$ cannot be alanine. Illustrative but not exclusive examples of $R_1$ are pentadecyl, nonadecyl, or heptadecyl radicals.

Illustrative examples of the present urushiol esters include esters wherein $R_2$ and $R_3$ are both-4-(4-aminophenyl)-butyrate

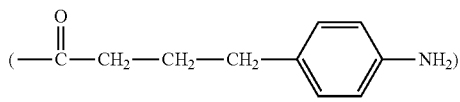

or esters of dipeptide valine-valine

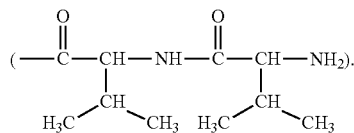

Additionally, the present urushiol esters can be esters wherein the urushiol ester is 3-n-pentadecylcatechol-di-4-(4-aminophenyl)-butyrate, 3-n-heptadecylcatechol-di-4-(4-aminophenyl)-butyrate, 3-n-pentadecylcatechol-di-valinyl-valinate or 3-n-heptadecylcatechol-di-valinylvalinate.

The present invention further encompasses pharmaceutical formulations comprising at least one urushiol ester effective for desensitizing a subject against contact dermatitis caused by allergens contained in plants of the Anacardiaceae and Ginkgoaceae families of the formula (IA)

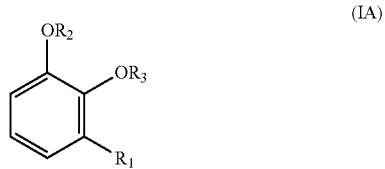

in sesame seed oil and about 2 to 12% benzyl alcohol and about 0 to 10% ethyl alcohol.

The present pharmaceutical formulations are especially adapted to be administered parenterally.

The present pharmaceutical formulations can comprise urushiol esters wherein the esters are esters of amino acids or combinations of amino acids or esters of a dicarboxylic acid or dicarboxylic acid derivative.

Illustrative esters of the present formulations include, for example, 3-n-pentadecylcatechol-di-4-(4-aminophenyl)-butyrate, 3-n-heptadecylcatechol-di-4-(4-aminophenyl)-butyrate, 3-n-pentadecylcatechol-di-valinylvalinate or 3-n-heptadecylcatechol-di-valinylvalinate. Esters wherein $R_1$ is nonadecyl are also encompassed by the formulations of this invention.

A preferred range for the pharmaceutical formulation are urushiol esters in sesame seed oil and about 2 to 12% benzyl alcohol and about 5 to 10% ethyl alcohol. A further preferred range is a formulation is urushiol esters in sesame oil and 2% (2 to 10) benzyl alcohol and about 10% ethyl alcohol.

BRIEF DESCRIPTION OF THE DRAWINGS

The above and other objects, features and advantages of the present invention will become more apparent from the following detailed description when taken in conjunction with the accompanying drawings, in which:

FIGS. 1A, 1B and 1C are results of Test #1, post urushiol challenge, for all test groups I-V at 24 hours, 48 hours and 72 hours, respectively;

FIGS. 2A, 2B and 2C are results of Test #2, post urushiol challenge, for all test groups I-V at 24 hours, 48 hours and 72 hours, respectively;

FIGS. 3A, 3B and 3C are results of Test #3, post urushiol challenge, for all test groups I-V at 24 hours, 48 hours and 72 hours, respectively;

FIGS. 4A-4E are pictures taken of skin lesions, post urushiol challenge, from Test #3 at 72 hours for all test groups I-V, respectively;

FIG. 6 is a set of pictures showing skin lesions at 72 hours, post urushiol challenge, for test group IV;

FIG. 7 is a set of pictures showing skin lesions at 72 hours, post urushiol challenge, for test group V;

FIG. 10: Mass chromatogram of PDC-valininate-allyl;

FIG. 11: Mass chromatogram of PDC-valininate;

FIG. 12: Mass chromatogram of PDC-alaninate-allyl;

FIG. 13: Mass chromatogram of PDC-alaninate;

FIG. 14: Mass chromatogram of PDC-glutaminate;

FIG. 15: HPLC chromatogram of PDC-APB;

FIG. 16: $^1$H-NMR of the PDC-APB in $CDCl_3$ as solvent;

FIG. 17: Carbon NMR of the PDC-APB in $CDCl_3$ as solvent;

FIG. 18: DEPT135 NMR of the PDC-APB in $CDCl_3$ as solvent;

FIG. 19: Mass spectrum of the PDC-APB;

FIG. 23A: Purity analysis HPLC 5% Ethanol, 10% benzyl alcohol in sesame seed (SS) oil, peak area and relative abundance;

FIG. 24A: Purity analysis HPLC 10% Ethanol, 10% benzyl alcohol in sesame seed (SS) oil, peak area and relative abundance;

FIG. 27A: Purity analysis HPLC 8% Ethanol, 2% benzyl alcohol in sesame seed (SS) oil, peak area and relative abundance;

FIG. 28A: Purity analysis HPLC 10% Ethanol, 2% benzyl alcohol in sesame seed (SS) oil, peak area and relative abundance;

FIG. 29A: Skin reaction and score at 24 hours post challenge #1, *$p<0.05$ as compared to vehicle;

FIG. 29B: Skin reaction and score at 48 hours post challenge #1, *$p<0.05$ as compared to vehicle;

FIG. 29C: Skin reaction and score at 72 hours post challenge #1, *$p<0.05$ as compared to vehicle;

FIG. 30A: Skin reaction and score at 24 hours post challenge #2, *$p<0.05$ #$p<0.01$ as compared to vehicle;

FIG. 30B: Skin reaction and score at 48 hours post challenge #2, #$p<0.05$ as compared to vehicle; and FIG. 30C: Skin reaction and score at 72 hours post challenge #2, #$p<0.01$ as compared to vehicle.

DETAILED DESCRIPTION OF THE INVENTION

Figure 5A:
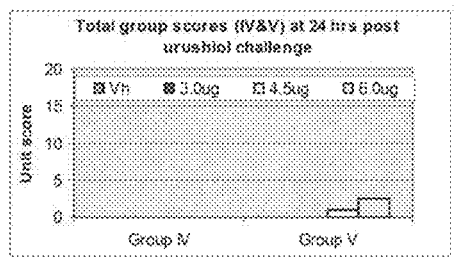
FIGS. 5A, 5B and 5C are results of Test #3, post urushiol challenge, at 24 hours, 48 hours and 72 hours, respectively, for test groups IV and V.
Figure 5B:
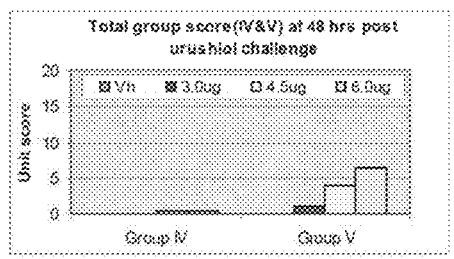
Figure 5C:
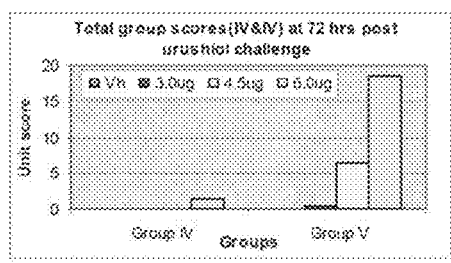

A strategy was developed comprising ester derivatives of urushiol. Said derivatives are able to quickly reach the blood stream following administration and hydrolyze at the surface of the blood cells resulting in the generation of active, free urushiol, which can then bind to cell membranes. The urushiol-cell membrane conjugate is believed to be the active entity causing desensitization.

By amino acid esters are meant esters of urushiols and urushiol cogeners in which the phenolic groups are esterified with a compound having a carboxy group capable of forming such esters as well as an amino group.

By an urushiol "amino acid ester" is meant, for example urushiol mono- or di-aminoacid ester. The amino group or groups may, of course, have originated from any amino acid, poly (amino acid) or peptide.

Useful compounds to make the present amino acid esters include both natural and synthetic amino acids as well as di-, tri- or polypeptides.

Useful amino acids include, for example, Alanine, Arginine, Asparagine, Aspartic Acid, Cysteine, Glutamine, Glutamic Acid, Glycine, Histidine, Isoleucine, Leucine, Lysine, Methionine, Phenylalanine, Proline, Serine, Threonine, Tryptophan, Tyrosine, Valine, Homoserine, Homoserine lactone, and Norleucine.

By carbamate derivatives of urushiol is meant urushiol derivatives in which the phenolic hydroxy groups are converted to carbamate linkage and the residue of the carbamate forming material includes a carboxyl group.

By a "dicarboxylic acid" here is meant an organic acid that has two carboxyl groups (—COOH). Suitable dicarboxylic acids in this invention are, for example, malonic acid, malic acid, glutaric acid and its derivatives, and succinic acid. Dicarboxylic acid derivatives include anhydrides and reactive derivatives of dicarboxylic acids such as, for example, dicarboxylic acid halides.

Compounds are disclosed which are effective for desensitizing a subject against contact dermatitis caused by allergens contained in plants of the Anacardiaceae and Ginkgoaceae families comprising urushiol esters of the following formula (I)

(I)

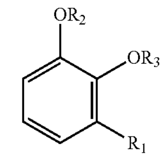

wherein $R_1$ is an alkyl radical having 11 to 19 carbon atoms, or an unsaturated congener thereof; or mixtures thereof; and $R_2$ and $R_3$ are each independently the residue radicals derived from an amino acid or a combination of amino acids, a carbamate-forming compound, an ester of a dicarboxylic acid or a dicarboxylic acid derivative or a sulfate or phosphate ester.

$R_1$ of formula (I) can be pentadecyl, heptadecyl, or nonadecyl.

The compounds of formula I can be esters of amino acids or combinations of amino acids, esters formed via dicarboxylic acids or dicarboxylic acid derivatives, phosphate or sulfate esters, or carbamate esters.

Illustrative but not limiting compounds include heptadecyl catechol phenyl alaninate ester, 3-hepta-1, 2-phenylene bis (4-aminophenyl) butanoate, heptadecyl catechol indolepropionate ester, heptadecyl catechol-β-alaninate ester, pentadecyl catechol valininate ester, pentadecyl catechol-di-valininate ester, pentadecyl catechol glutaminate ester, pentadecyl catechol asparaginate ester, pentadecyl catechol glutaminate-β-alanine dipeptide ester.

The invention also encompasses pharmaceutical compositions containing at least one compound according to formula (I) and suitable pharmaceutical carrier therefor. The present pharmaceutical compositions are pharmaceutical formulations in which the at least one active material is in sesame seed oil containing benzyl alcohol and optionally ethyl alcohol.

These pharmaceutical compositions are adapted to be administered parenterally, transdermally or intranasally.

The invention further encompasses a method of desensitizing a subject to allergens contained in plants of the Anacardiaceae and Ginkgoaceae families which comprises administering to said subject a composition comprising a compound or mixture of compounds according to formula (I).

The method of treatment can be by parenteral, transdermal or transnasal administration to a subject.

The present method of desensitizing a subject to allergens contained in plants of the Anacardiaceae and Ginkgoaceae families comprises administering to said subject, of a pharmaceutical formulation containing a compound or mixture of compounds according to formula (I).

The following experimental describes methods of preparing the derivatives of the present invention. A person of skill in the art will recognize that these preparatory methods are broadly applicable to the preparation of various ester derivatives of urushiol. Accordingly, the proceeding methods are exemplary. Further, a person of skill in the art will also recognize that methods of tolerization and/or densensitization are also broadly applicable.

Experimental

The present derivatives may be and were evaluated based on synthetic yields, polarity, and purity as criteria for suitability. Further, derivatives may be and were tested for efficacy in producing tolerance to sensitization to poison ivy/poison oak urushiols in the guinea pig animal model or desensitization of already sensitized animals.

It is well-recognized in the art that successful treatment by use of a medicament or other agent in an animal model, such as the guinea pig animal model of the current invention, is strongly correlative to effects in other animal models including humans.

Synthesis of Derivatives of Urushiols:

Four different types of derivatives of urushiols can be prepared, namely amino acid esters, dicarboxylic acid esters, carbamates with free terminal carboxylic groups, and sulfate and phosphate esters. Other groups which satisfactorily provide polarity to the urushiols and appropriate bioactivity, including hydrolyzation ability in-vivo are also contemplated.

Accordingly, the preceeding products are also exemplary. These products can be purified using different chromatographic techniques such as column chromatography, thin layer chromatography, and high performance liquid chromatography. Spectral analysis using, for example, Mass Spectrometry (MS), $^1$H-NMR, Infrared/Ultraviolet Spectral Analysis (e.g. FTIR), and $^{13}$C-NMR along with melting point and elemental analysis, can carry out structural confirmation.

Synthesis of Amino Acid Esters of Urushiols:

Pentadecyl catechol (PDC, 1) and heptadecyl catechol (HDC, 2) (the saturated congeners of poison ivy and poison oak urushiols, respectively) can be used to prepare esters with different amino acids such as, those depicted in structures 3-12. Other amino acids and amino acid radicals (di, tri or polypeptides) are also contemplated.

The starting materials (1 and 2) can be prepared by hydrogenation of purified poison ivy and poison oak urushiols, respectively. Alternatively, compounds 1 and 2 are prepared synthetically as exemplified in procedures 1, 2, and 3 as described in examples 1-3. Unsaturated congeners are also contemplated starting materials, e.g., unsaturated congeners of compound (1) or (2) may be derivatized to form unsaturated-catechol derivatives.

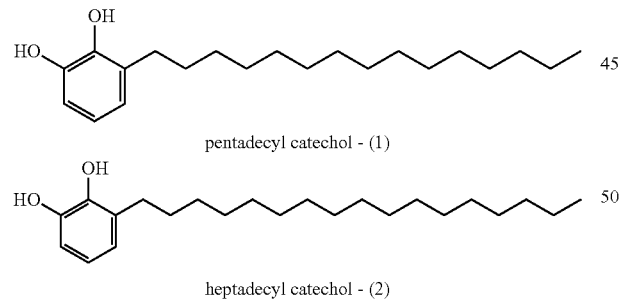

(1) or (2) can be dissolved in dichloromethane (DCM), and an amino acid (2.2 eq), such as one mentioned above, can be added to the solution. Catalytic amounts of dimethylaminopyridine (4-DMAP, e.g., 0.1 eq), along with dicyclohexylcarbodiimide (DCC, 2.2 eq) can then be added and the reaction mixture allowed to stir until thin-layer chromatography (TLC) confirms the complete conversion of the starting material to the product.

Suitable staining agents and other detection means, including ultraviolet analysis of the TLC plate, may be used and persons of skill in the art would readily be able to determine such agents and/or techniques. Exemplary techniques include: ferric chloride as a monitoring agent, wherein free catechols give an immediate, distinct dark blue color.

Pretreatment of the TLC plate is also within the skill of one of the art and includes use of 1N NaOH, as a plate-spray, to induce alkaline hydrolysis of esters, prior to staining with ferric chloride. Again, suitable workup techniques are within the skill of the art, and include reaction filtration, separation or washing as by use of a separatory funnel and suitable solvents, drying of organic solvents such as with magnesium sulfate or sodium sulfate, and concentration such as by rotary evaporation.

Products protected by N-tert-butoxycarbonyl (t-Boc) are, preferably, to be purified primarily by column chromatography on silica gel with monitoring of fractions by any suitable technique including TLC.

Deprotection of T-BOC:

Anhydrous tetrahydrofuran (THF) is bubbled with HCl gas to saturation. Excess HCl gas is flushed with nitrogen. The t-Boc derivatives can then be dissolved in anhydrous THF. This is followed by the dropwise addition of acidic THF. After addition of all acidic THF, the mixture is to be allowed to stir at room temperature until complete deprotection is confirmed by TLC or any other suitable technique. The solvent is then evaporated. Acetone is then added to the residue and the mixture is to be stored in the freezer overnight. In the morning, the solid product thus obtained is filtered. This crystallization procedure may be repeated for complete recovery of the product (Scheme 1). Some amino acid esters of 1 and 2 may have high solubility in acetone and therefore may not crystallize. In these cases, the solvent is to be evaporated to produce the solid product which is to be crystallized from an appropriate solvent.

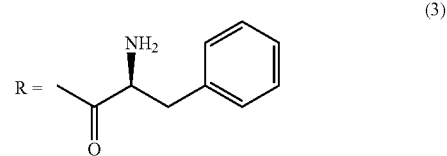

(3)

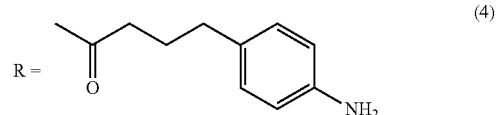

(4)

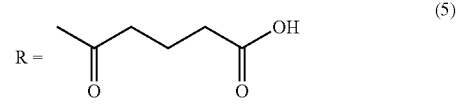

(5)

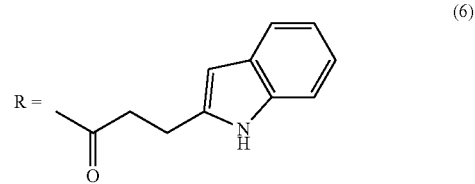

(6)

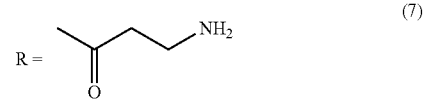

(7)

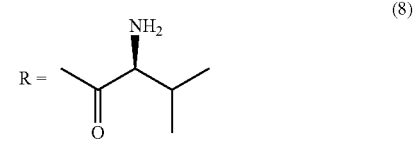

(8)

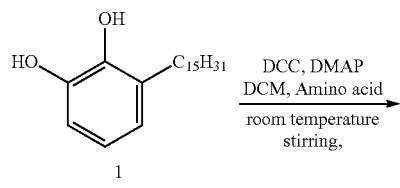

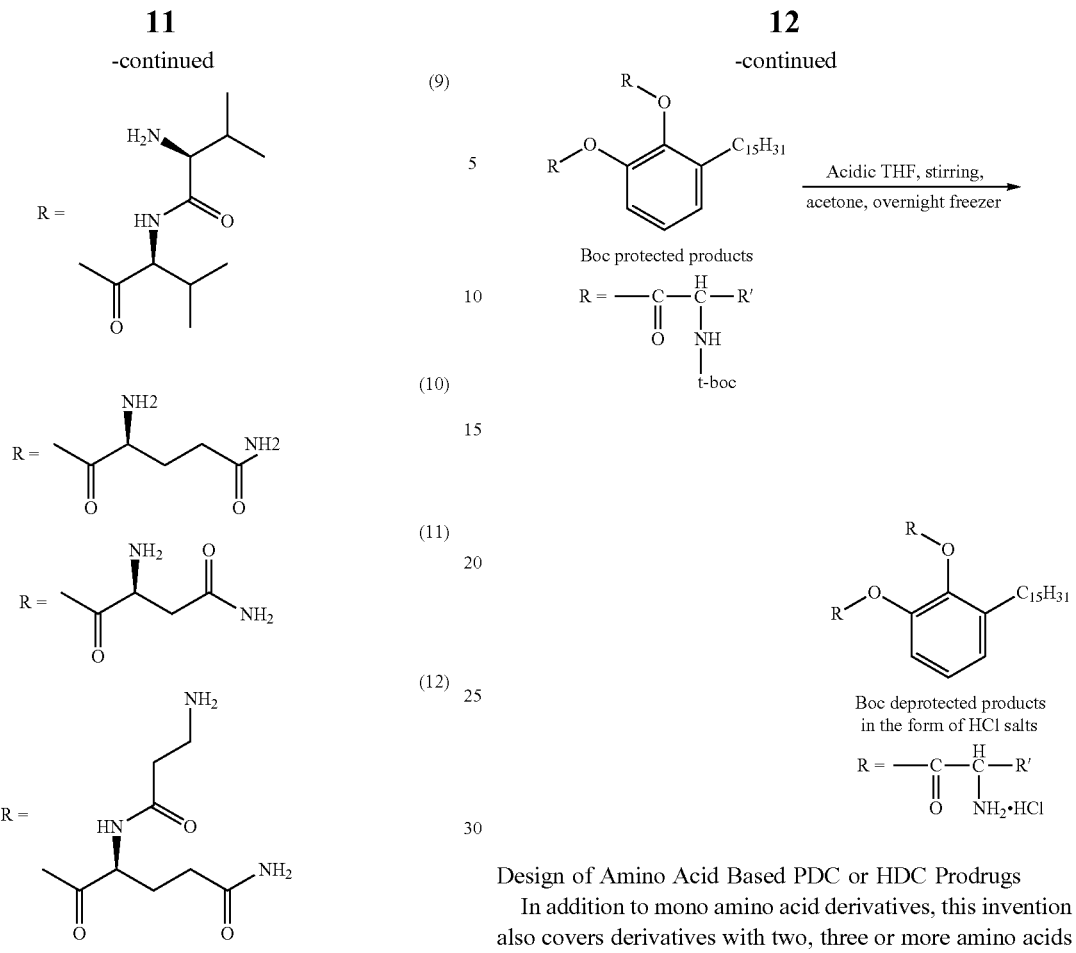

Design of Amino Acid Based PDC or HDC Prodrugs

In addition to mono amino acid derivatives, this invention also covers derivatives with two, three or more amino acids (di, tri, or poly peptide derivatives). Such derivatives might have enhanced stability in addition to their water solubility. Synthesis of dipeptide derivatives follow the same procedure described for the mono derivatives where by the mono derivative is used to add another amino acid to make the dipeptide and the dipeptide used to add another amino acid to form the tripeptide derivative etc. This is depicted in the general scheme below. Alternatively for the polypeptide derivative, the polypeptide itself is first synthesized to the desired length followed by reacting the polypeptide directly with compound 1 or 2 to form the desired product.

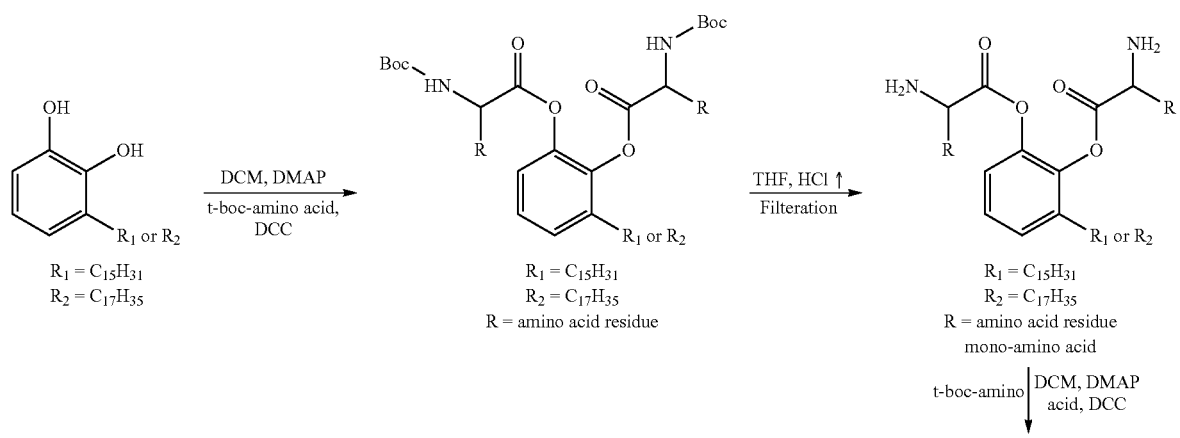

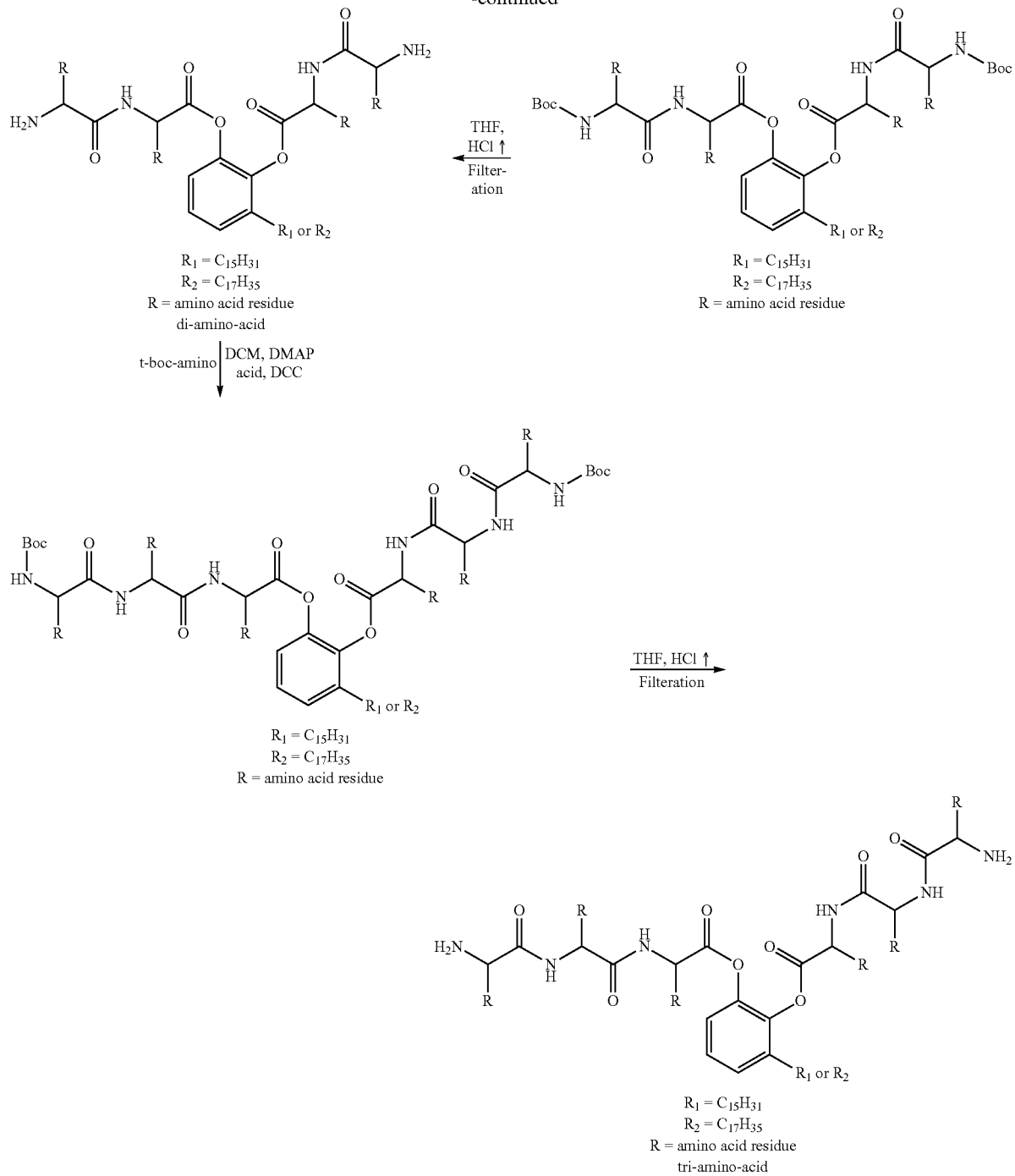

Synthesis of Carbamates of Urushiols:

Pentadecyl catechol (1) and heptadecyl catechol (2) can be used to make different carbamates using the following general procedure as outlined in Scheme 2.

The starting material is dissolved in freshly distilled DCM and DMAP and triethylamine added, followed by 4-nitrophenyl-chloroformate. The reaction can be monitored by TLC for completeness. When complete, 4-aminobutyric acid allyl ester or 6-aminohexanoic acid allyl ester or 4-(4-aminophenyl) butyric acid allyl ester dissolved in DCM are to be added dropwise to form the allyl esters of the final products 13-15 respectively. TLC can again monitor the reactions for completion. The protected products can be purified by different chromatographic techniques.

Deprotection of the Allyl Esters of the Carbamates:

The products can be dissolved in DCM and phenylsilane is added to the solution along with tetrakis(triphenylphosphine)palladium. The reaction mixture is allowed to stir at room temperature and can be monitored by TLC for completion. Methanol (MeOH) is then to be added and stirring continued for another 15 minutes. The solvent is then evaporated and the product purified using chromatographic techniques.

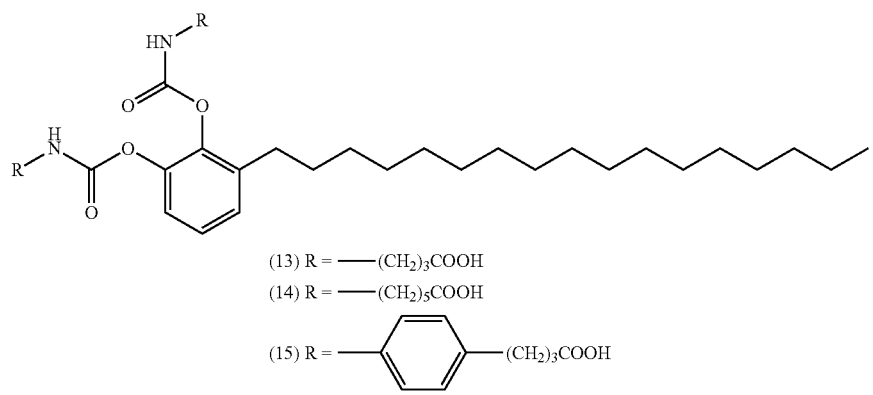

(13) R = —(CH₂)₃COOH
(14) R = —(CH₂)₅COOH
(15) R = —⟨C₆H₄⟩—(CH₂)₃COOH

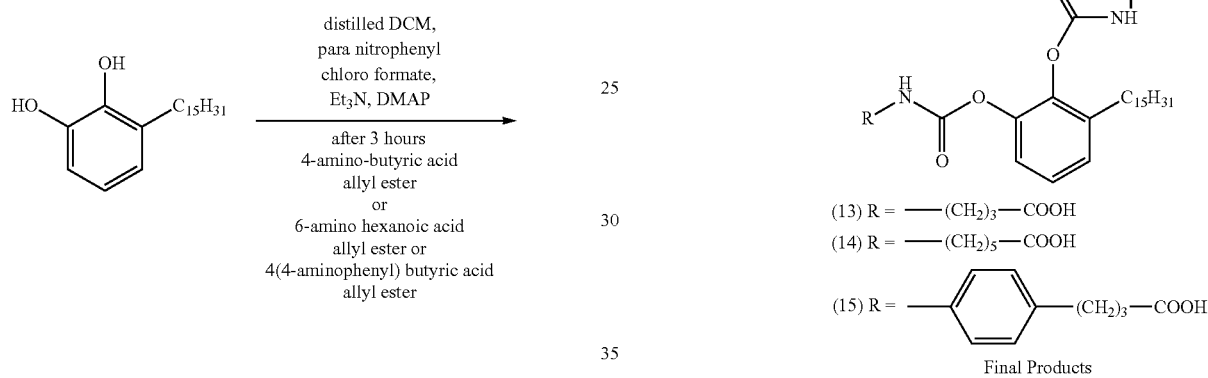

Scheme 2. General Procedure for the synthesis of carbamates of 1 and/or 2

Reagents: distilled DCM, para nitrophenyl chloro formate, Et₃N, DMAP; after 3 hours 4-amino-butyric acid allyl ester or 6-amino hexanoic acid allyl ester or 4(4-aminophenyl) butyric acid allyl ester

(13) R = —(CH₂)₃—COOH
(14) R = —(CH₂)₅—COOH
(15) R = —⟨C₆H₄⟩—(CH₂)₃—COOH

Final Products

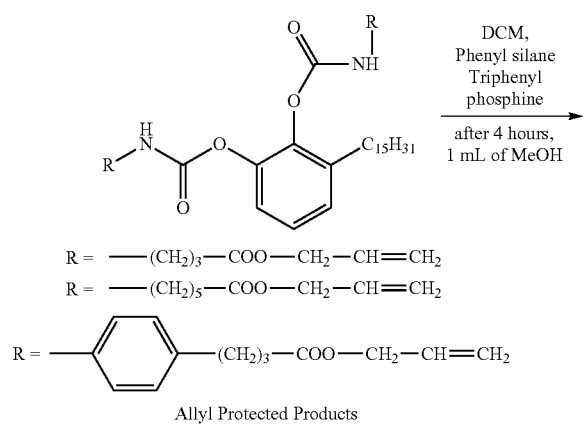

R = —(CH₂)₃—COO—CH₂—CH=CH₂
R = —(CH₂)₅—COO—CH₂—CH=CH₂
R = —⟨C₆H₄⟩—(CH₂)₃—COO—CH₂—CH=CH₂

Allyl Protected Products

Reagents: DCM, Phenyl silane, Triphenyl phosphine; after 4 hours, 1 mL of MeOH

Synthesis of the Sulphate Esters of the Urushiols:

The starting material (1 or 2) can be dissolved in anhydrous toluene, cooled to and maintained at −16 to −18° C. While maintaining the temperature, chlorosulfonic acid is added dropwise over a period of 30 minutes. The reaction is then allowed to stir until completion as indicated, e.g., by TLC. Once the reaction is complete, 0.1N HCl is to be added and the mixture extracted with DCM three times. The organic layers will be combined and evaporated to dryness. The product (16, starting from 2) may be purified using different chromatographic techniques.

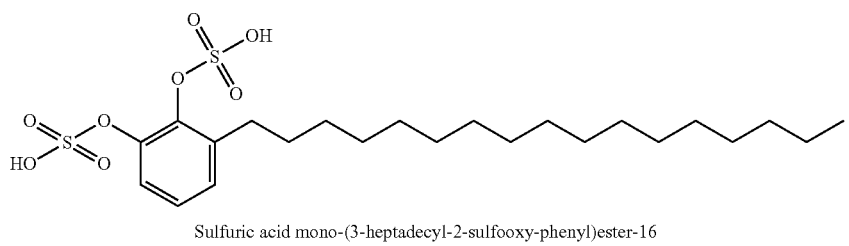 [SMILES: CCCCCCCCCCCCCCCCCc1cccc(OS(=O)(=O)O)c1OS(=O)(=O)O]

Sulfuric acid mono-(3-heptadecyl-2-sulfooxy-phenyl)ester-16

EXAMPLES

Example 1

Synthesis of Penta or Hepta Decyl Catechol (PDC or HDC) (Procedure 1)

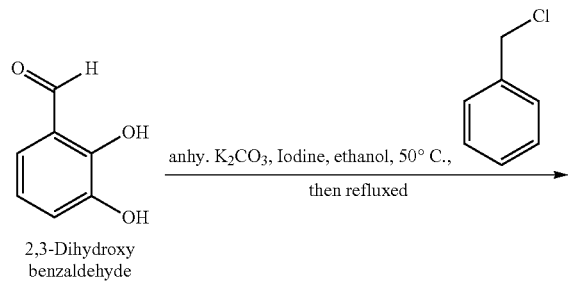

2,3-Dihydroxy benzaldehyde

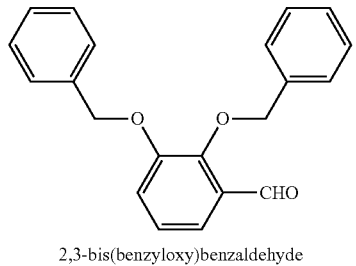

2,3-bis(benzyloxy)benzaldehyde

To a solution of 2,3-dihydroxy benzaldehyde in anhydrous ethanol was added anhydrous $K_2CO_3$ along with catalytic amount of iodine and stirred at 5° C., while benzyl chloride was added drop wise.

The mixture was refluxed while stirring for 3 hours and then additional benzyl chloride was added and refluxed for another 2 hours.

The solvent was evaporated and the residue was partitioned between ether and water. The organic solution was washed with water and dried over sodium sulfate. All volatiles were evaporated on high vacuum and the product was obtained as light yellow solid material. The yield was quantitative.

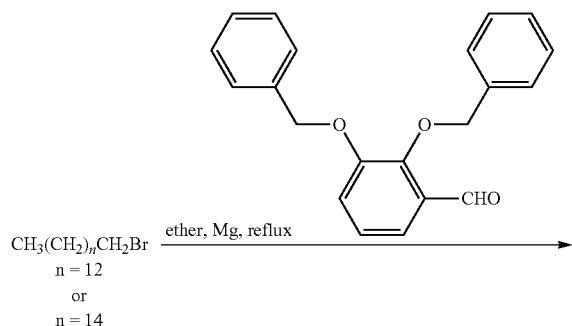

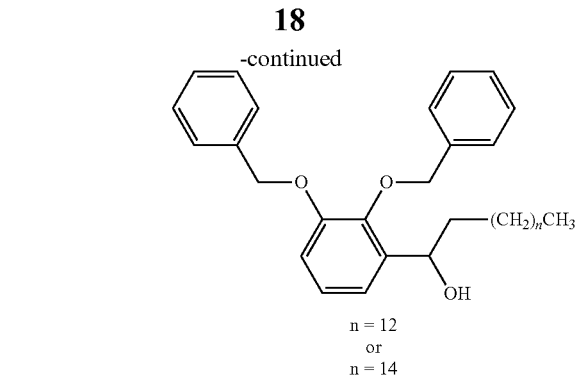

n = 12 or n = 14

The tetradecyl Grignard reagent was prepared in the usual way from tetradecyl bromide, magnesium and trace of iodine in ether. To this solution at reflux was added 2,3 dibenzyloxy-benzaldehyde in ether. After the addition the mixture was refluxed for 4 hours, cooled, treated at 22° C. with 12% hydrochloric acid. The layers were separated and the organic layer was washed twice with water and then with brine. The solvent was evaporated to produce an oily crude product which was dissolved in ice cold methanol and the precipitated waxes were filtered.

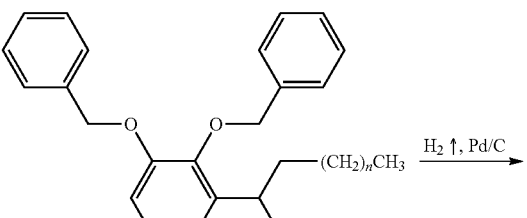

n = 12 or n = 14

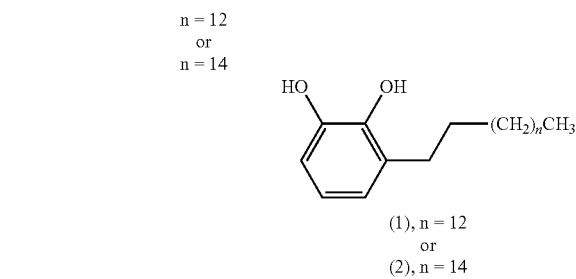

(1), n = 12 or (2), n = 14

Hydrogenation of 2,3 dibenzyloxy-tetradecyl benzyl alcohol or 2,3 dibenzyloxy-hexadecyl benzyl alcohol was carried out with 10% Pd/C catalyst and conc. $H_2SO_4$ at 200 PSI and 125° C. to produce pentadecyl catechol (1) or heptadecyl catechol (2).

Example 2

Synthesis of Penta or Hepta Decyl Catechol (PDC or HDC) (Procedure 2)

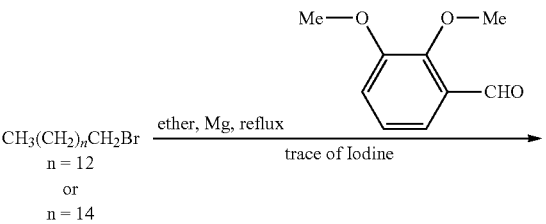

-continued

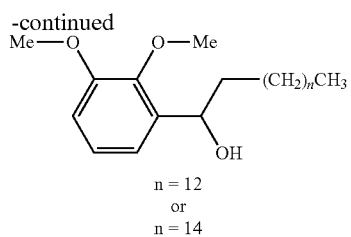

n = 12
or
n = 14

The tetradecyl Grignard reagent was prepared in the usual way from tetradecyl bromide (3.3 mmole), magnesium (3.5 mmole) and a trace of iodine in 3 L of ether. To this was added at reflux a solution of 2,3-dimethoxy-benzaldehyde (2.9 mmole) in 1 L of ether. After the addition, the mixture was refluxed for 4 hours, cooled, treated at 20° C. with 3 L of 12% HCl, the layers separated, and the organic layer washed twice with water and then once with brine. The ether was then rotaevaporated leaving a syrup which was dissolved in 2 L of MeOH. After cooling in an ice bath overnight the precipitated waxes were filtered. The crude product was isolated from the filtrate by rotaevaporation of all volatiles. The yield was quantitative.

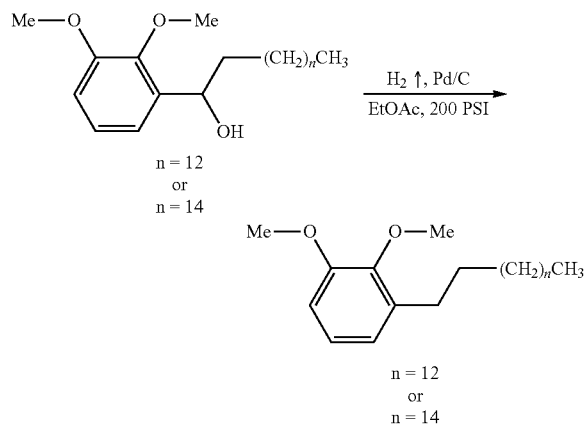

2,3-Dimethoxy-1-tetradecylbenzyl alcohol (1.7 mmole, crude) in 1.5 L of ethyl acetate was hydrogenated with 10 g 10% Pd/C catalyst and 10 mL of conc. $H_2SO_4$ at 200 PSI and 125° C. The reaction was complete in 4-6 hrs. The catalyst was filtered. The filtrate was washed twice with water and once with brine. After drying over $MgSO_4$ the solvent was rotaevaporated and residual oil distilled. Considerable material (unidentified) was obtained up to 160° at 0.1 Torr. The product was then collected at 165-195° at 0.2 Torr.

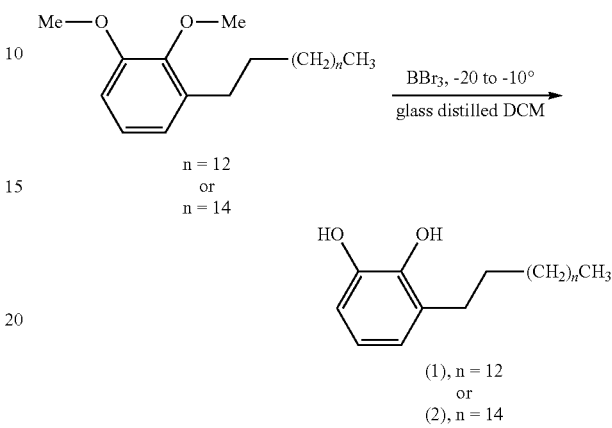

2,3-Dimethoxy-6-pentadecyl-catechol (0.9 mmole) in 500 mL of glass-distilled methylene chloride (DCM) was added dropwise at −20 to −10° to a stirred solution of boron tribromide ($BBr_3$) (2.4 mmole) in 2 L of glass distilled DCM in a nitrogen atmosphere. After the addition was complete, the mixture was stirred overnight at room temperature. Methanol was added at 10° to 20°. The mixture was warmed to 30° to 40° under a strong stream of nitrogen to remove much of the hydrogen bromide present. Crystallization was used to purify the product.

Example 3

Synthesis of Penta or Hepta Decyl Catechol (PDC or HDC) (Procedure 3)

An alternate to the Grignard's reaction described in the above procedures, Wittig reaction was used to form an olefin as shown below followed by appropriate steps to yield the desired product.

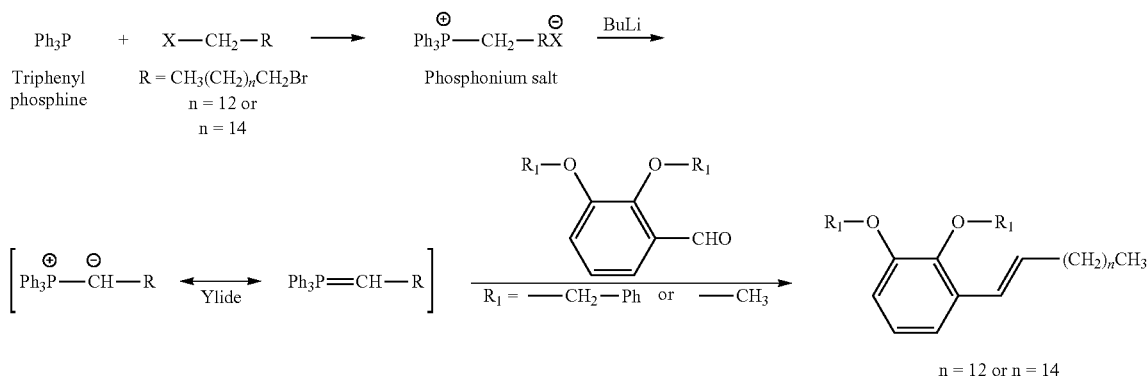

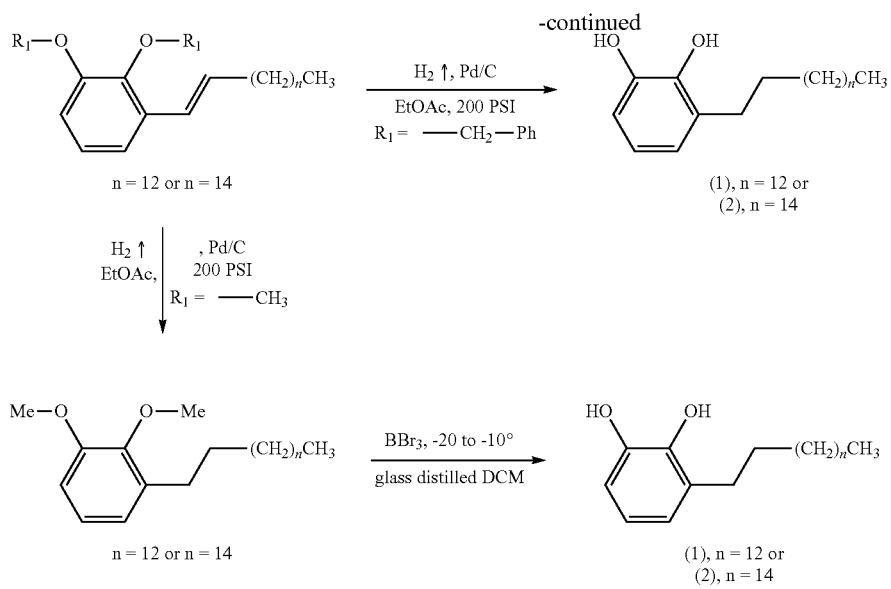

All the compounds formed were analyzed on HPLC for their purity (>99.5%).

Example 4

Preparation of HDC-Phenyl Alaninate Ester (3)

Heptadecyl catechol (HDC, 2, 0.25 g) was dissolved in 20 mL of DCM, and t-boc-L-phenyl-alanine (2.2 eq) was added to the solution. A catalytic amount of DMAP, and DCC (2.2 eq) was then added and the reaction mixture was allowed to stir until TLC confirmed complete conversion of the starting material to the product.

Ferric chloride was used as reagent to monitor the reaction mixture on TLC, where the free catechols gave immediate distinct dark blue color with the reagent. However, the esters needed base hydrolysis before producing the color. 1 N NaOH was used as a second spray to hydrolyze the esters and locate the spots of the esters. Upon completion of the reaction, the reaction mixture was filtered to get rid of the majority of the reagents, and the solvent was then evaporated.

The t-boc-protected product was purified using column chromatography on silica gel and the collected fractions were monitored by TLC.

Anhydrous THF was bubbled with HCl gas to saturation. Excess HCl gas was flushed with nitrogen. The t-boc derivative was dissolved in anhydrous THF, and acidic THF was added drop-wise. After addition of all the acidic THF, the mixture was allowed to stir at room temperature until completely deprotected as confirmed by TLC. The solvent was then evaporated and acetone was added to the residue. Upon storage of the mixture in the freezer overnight, a solid product was obtained by filtration. This crystallization procedure was repeated to get 239 mgs of the product (73%).

The product was confirmed by HREIMS (TOF) m/z 643.4470 [M+H]$^+$ (calculated for $C_{41}H_{58}N_2O_4$, 643.4475) and other spectral techniques.

Polarity of HDC-Phenyl Alaninate Ester:

HDC-phenyl alaninate (10 mg) formed a homogenous solution when dissolved in 50 ul of ethanol and the resulting solution adjusted to 1 ml with water.

(3)

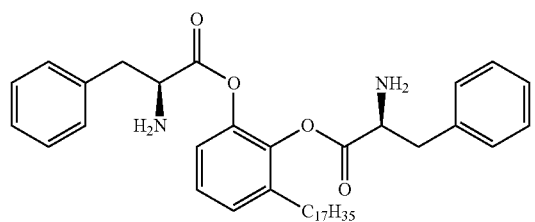

Example 5

Preparation of 3-hepta-1, 2-phenylene bis (4-aminophenyl) butanoate (4)

Heptadecyl catechol (HDC, 2, 0.15 g) was dissolved in 10 mL of DCM, and 4-amino-phenyl-butyric acid (2.2 eq.) was added to the solution. A catalytic amount of DMAP and DCC (2.2 eq.) was then added and the reaction mixture was allowed to stir until TLC confirmed complete conversion of the starting material to the product (also referred to as HDC-4-(4-aminophenyl)-butyrate ester), 4.

The reaction mixture was worked up as usual and the product was purified using column chromatography on silica gel. The fractions containing the product were combined to give 144 mgs of the product (89%).

The product was confirmed by HREIMS (TOF) m/z 671.4788 [M+H]$^+$ (calculated for $C_{43}H_{63}N_2O_4$, 671.4970) and other spectral techniques.

10 mg of 3-hepta-1,2-phenylene bis (4-aminophenyl) butanoate was a clear solution when dissolved as a HCl salt in 50 ul of ethanol and the resulting solution adjusted to 1 mL with water (10 mg/mL).

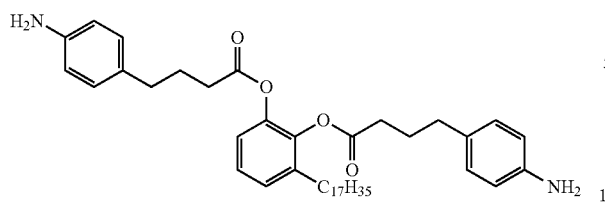

(4)

Synthesis of Urushiol Esters Having Terminal Carboxylic Functions:

Example 6

Preparation of 5,5'(3-heptadecyl-1,2-phenylene)bis(oxy)bis(5-oxopentanoic acid) (5)

Heptadecyl catechol (HDC, 2, 0.15 g) was dissolved in 10 mL of DCM, and glutaric anhydride (2.2 eq.) was added to the solution. Catalytic amounts of DMAP and tri-ethyl amine was then added and the reaction mixture was allowed to stir until TLC confirmed the complete conversion of the starting material to the product, 5, also referred to as HDC-hemiglutarate.

The reaction mixture was worked up as mentioned above and the product was purified using column chromatography on silica gel and fractions containing the product were combined to give 180 mgs of the di-hemiglutarate ester of HDC (72%), (5).

The product was confirmed by HREIMS (TOF) m/z 575.3740 [M−H]$^+$ (calculated for $C_{33}H_{52}O_8$, 575.3731) and by other spectral analysis techniques.

give of the product (90%). The product was confirmed by HREIMS (TOF) m/z 725.4248 [M+Cl]$^−$ (calculated for $C_{45}H_{58}ClN_2O_4$, 725.4080).

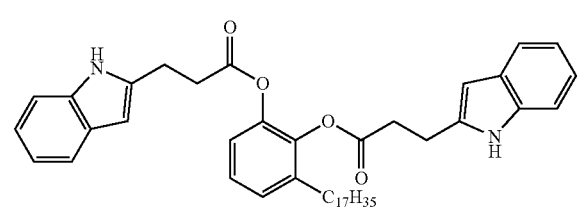

(6)

Example 8

Preparation of HDC-β-Alaninate Ester (7)

Heptadecyl catechol (HDC, 2, 0.10 g) was dissolved in 10 mL of DCM, and t-boc-β-alanine (2.2 eq.) was added to the solution. Catalytic amount of DMAP, along with (2.2 eq.) of DCC was then added and the reaction mixture was allowed to stir until TLC confirmed the complete conversion of the starting material to the product.

The reaction mixture was worked up as usual and the product was purified using column chromatography on silica gel and fractions containing the product were combined to give of the product (85%).

Deprotection of t-boc was accomplished as described earlier. The acetone crystallization procedure is repeated to get the pure product. The product was confirmed by HREIMS (TOF) m/z 490.3371 [M+H]$^+$ (calculated for $C_{29}H_{51}N_2O_4$, 491.4072).

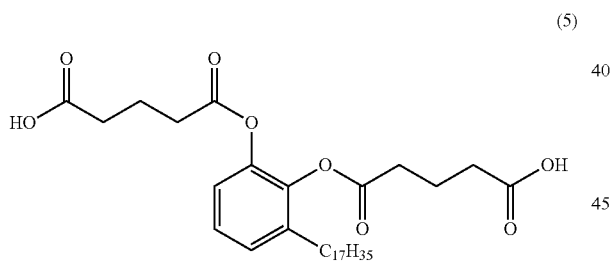

(5)

10 mg of dihemiglutarate ester of HDC formed a homogenous solution when dissolved in 50 ul of ethanol and the resulting solution adjusted to 1 ml with potassium phosphate buffer (pH 8).

Example 7

Preparation of HDC-Indole-Propionate Ester (6)

Heptadecyl catechol (HDC, 2, 0.20 g) was dissolved in 10 mL of DCM, and indole propionic acid (2.2 eq.) was added to the solution. Catalytic amount of DMAP, along with (2.2 eq.) of DCC was then added and the reaction mixture was allowed to stir until TLC confirmed the complete conversion of the starting material to the product.

The reaction mixture was worked up as usual and the product was purified using column chromatography on silica gel and fractions containing the product were combined to

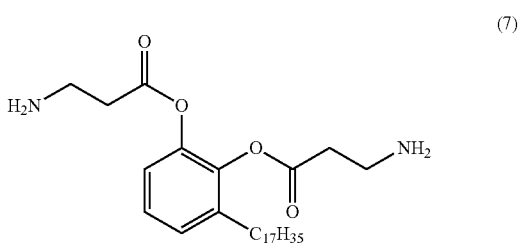

(7)

Example 9

Preparation of PDC-Valininate Ester (8)

Pentadecyl catechol (PDC, 1, 0.25 g) was dissolved in 20 mL of DCM, and t-boc-L-valine (2.2 eq) is added to the solution. Catalytic amount of DMAP, along with (2.2 eq) of DCC was then be added and the reaction mixture was allowed to stir until TLC confirms the complete conversion of the starting material to the product.

The product was confirmed by HREIMS (TOF) m/z 719.5220 [M+H]$^+$ (calculated for $C_{41}H_{71}N_2O_8$, 719.5205).

The t-Boc protected product was purified using column chromatography on silica gel and monitoring the fractions by TLC.

Deprotection of t-boc was accomplished as described previously. The acetone crystallization procedure was repeated to get the pure product. The product was confirmed by HREIMS (TOF) m/z 519.4224 [M+H]$^+$ (calculated for $C_{31}H_{55}N_2O_5$, 519.4956).

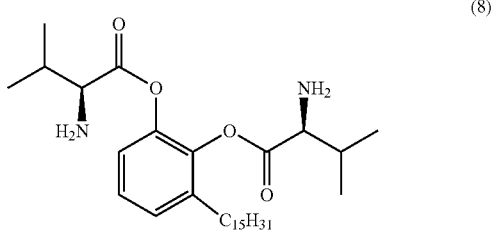

(8)

Example 10

Preparation of PDC-Di-Valininate Ester (9)

PDC-valine was dissolved in 20 mL of DCM, and t-boc-L-valine (2.2 eq) was added to the solution. Catalytic amount of DMAP, along with (2.2 eq) of DCC was then be added and the reaction mixture was allowed to stir until TLC confirms the complete conversion of the starting material to the product.

The t-Boc protected product was purified using column chromatography on silica gel and monitoring the fractions by TLC. The product was confirmed by HREIMS (TOF) m/z 917.6553 [M+H]$^+$ (calculated for $C_{59}H_{89}N_4O_{10}$, 917.6573).

Deprotection of t-boc was accomplished by the procedure described earlier. The acetone crystallization procedure was repeated to get the pure product. The product was confirmed by HREIMS (TOF) m/z 717.5561 [M+H]$^+$ (calculated for $C_{41}H_{73}N_4O_6$, 717.5525).

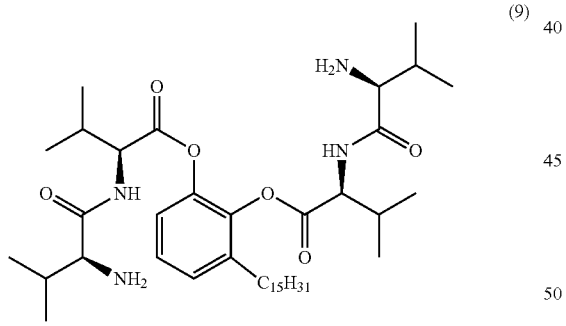

(9)

Example 11

Preparation of PDC-Glutaminate Ester (10)

Pentadecyl catechol (PDC, 1, 0.05 g) was dissolved in 10 mL of DCM, and t-boc-L-glutamine (2.2 eq) was added to the solution. Catalytic amount of DMAP, along with (2.2 eq) of DCC was then added and the reaction mixture was allowed to stir until TLC confirmed the complete conversion of the starting material to the product.

The t-boc protected product was purified using column chromatography on silica gel and monitoring the fractions by TLC.

Deprotection of t-boc was accomplished by the procedure described earlier. The acetone crystallization procedure was repeated to get the pure product. The product formed was confirmed by HREIMS (TOF) m/z 577.3966 [M+H]$^+$ (Calculated for $C_{31}H_{53}N_4O_6$, 577.3960).

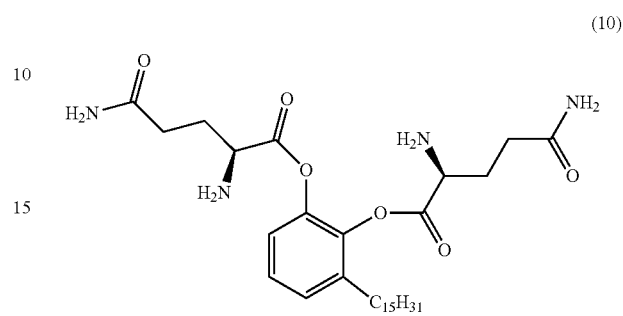

(10)

Example 12

Preparation of PDC-Asparaginate Ester (11)

Pentadecyl catechol (PDC, 1, 0.05 g) was dissolved in 10 mL of DCM, and t-boc-L-asparagine (2.2 eq) was added to the solution. Catalytic amount of DMAP, along with (2.2 eq) of DCC was then added and the reaction mixture was allowed to stir until TLC confirmed the complete conversion of the starting material to the product.

The t-Boc protected product was purified using column chromatography on silica gel and monitoring the fractions by TLC.

Deprotection of t-boc was accomplished as described previously. The acetone crystallization procedure was repeated to get the pure product. The product formed was confirmed using LC/MS m/z 549.5 [M+H]$^+$.

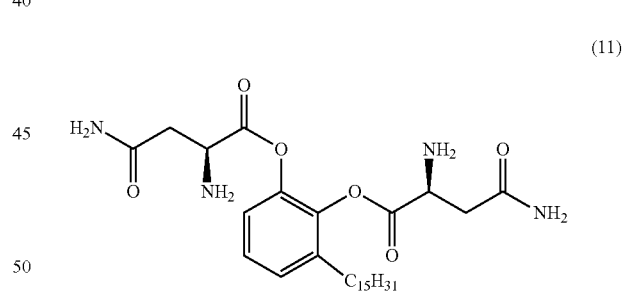

(11)

Example 13

Preparation of PDC-Glutaminate-β-Alanine Dipeptide Ester (12)

PDC-glutaminate ester (10) was dissolved in 8 mL of DCM, and t-boc-β-alanine (2.2 eq) was added to the solution. Catalytic amount of DMAP, along with (2.2 eq) of DCC was then added and the reaction mixture was allowed to stir until TLC confirmed the complete conversion of the starting material to the product.

The t-boc protected product was purified using column chromatography on silica gel and monitoring the fractions by TLC.

Deprotection of t-boc was accomplished as described previously. The acetone crystallization procedure was repeated to get the pure product. The product formed was confirmed using LC/MS m/z 719.6 [M+H]$^+$.

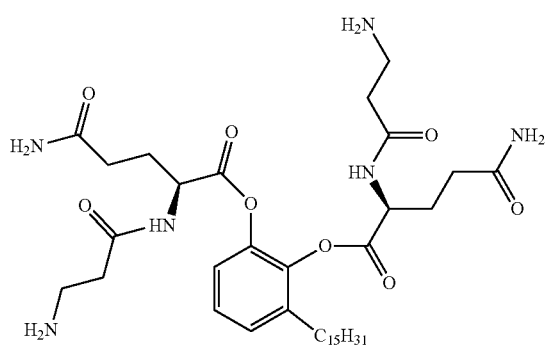

(12)

Example 14

Induction of Tolerance to Poison Ivy/Poison Oak Urushiol Using Derivatives of 3-N-Heptadecylcatechol in the Guinea Pig Contact Dermatitis Model Specifically, three derivatives of 3-n-heptadecylcatechol (HDC, the saturated congener of poison oak urushiol) have been prepared and tested, namely: HDC phenyl alaninate ester (3), HDC hemiglutarate ester (5) and HDC 4-(4-aminophenyl)butyrate ester (4). A guinea pig animal model has been used to evaluate these agents activity vis-à-vis contact dermatitis and other biological activity.

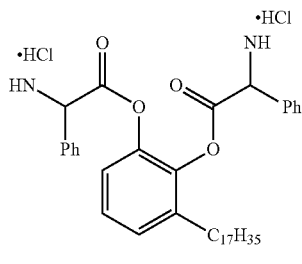

3

HDC Phenyl alaninate ester

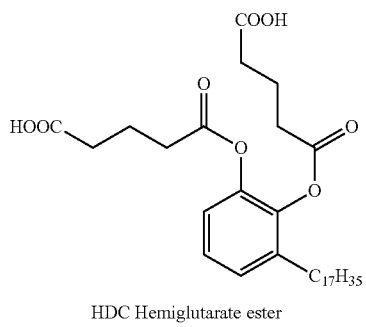

5

HDC Hemiglutarate ester

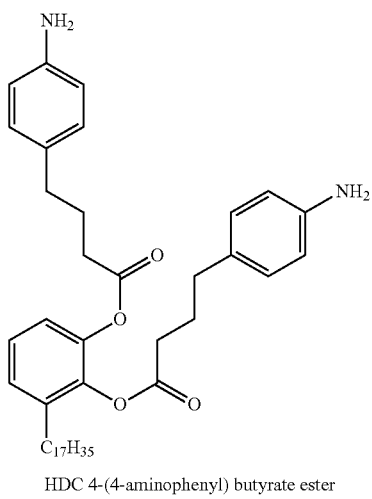

4

HDC 4-(4-aminophenyl) butyrate ester

Figure 8:
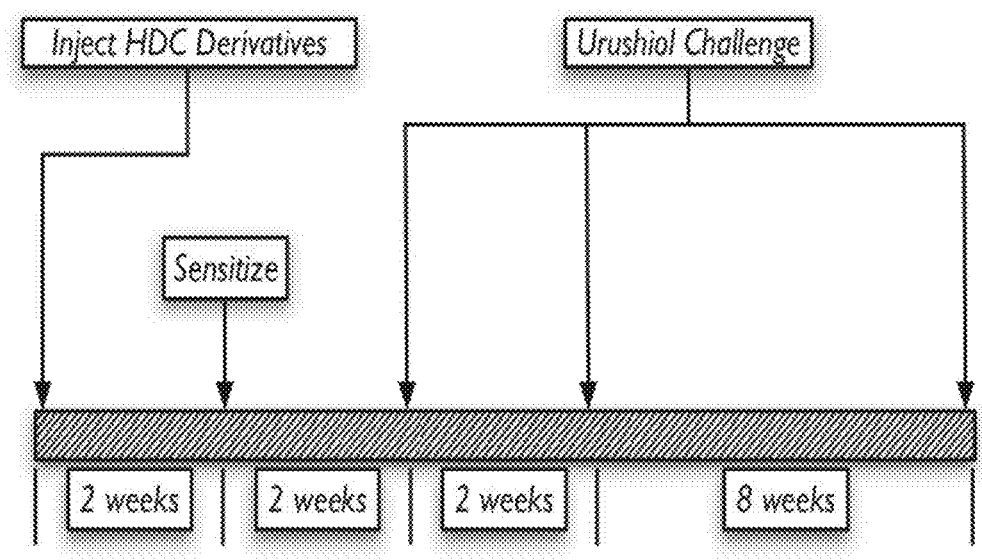
FIG. 8 is a schematic study design showing the general procedure for determining the efficacy of the agents produced according to the present invention for the results shown in FIGS. 1A-1C through 3A-3C.

Animals: Hartley strains of guinea pigs (n=40) were obtained from Harlan, Indianapolis Ind. 46229. The animals were divided in the 5 groups (n=8/group) and treated as described hereunder. These animals were kept in a controlled environment with a 12-hour day and night cycle and provided feed and water ad libitum. Study design: FIG. 8 describes the general procedure for determining the efficacy of the agents produced according to the present invention. As can be seen in FIG. 8, HDC derivatives are injected at week 0, followed by a sensitization at 2 weeks, and subsequent urushiol challenges in subsequent weeks.

Figure 9:
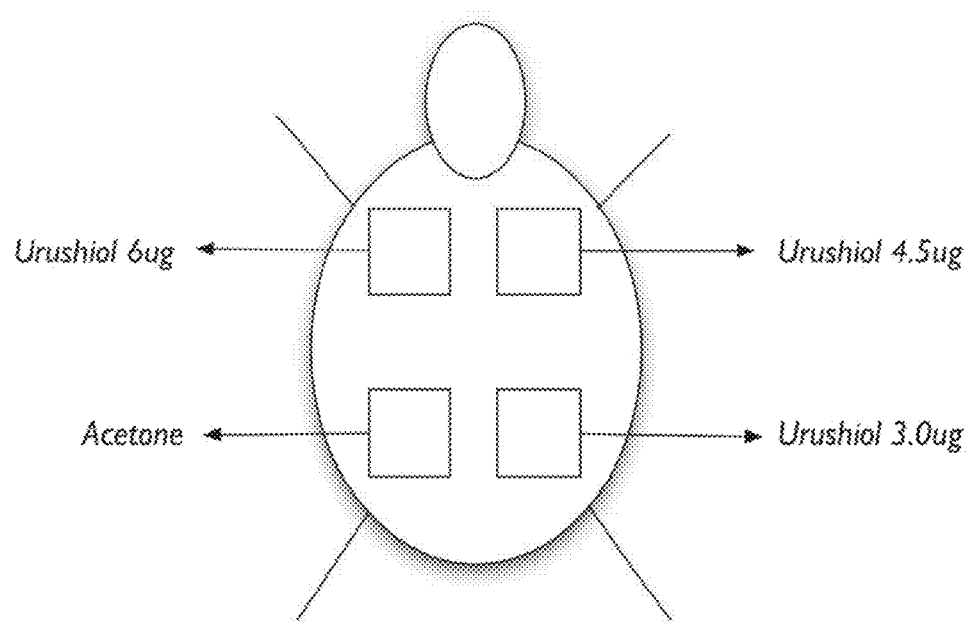
FIG. 9 is a schematic representation of injection sites of Urushiol challenge doses on abdominal skin.
Figures 20A, 20B:
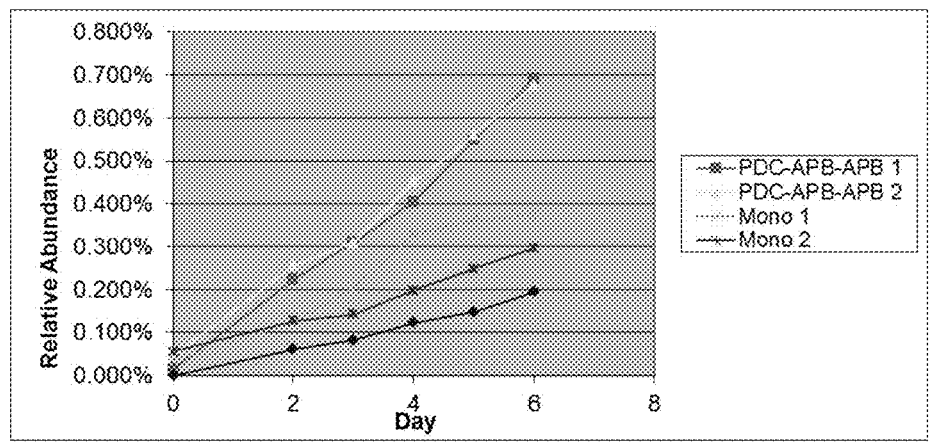
FIG. 20A: Purity analysis HPLC 10% benzyl alcohol in sesame seed (SS) oil, peak area and relative abundance.
FIG. 20B: Purity analysis HPLC 10% benzyl alcohol in SS oil, relative abundance.
Figures 21A, 21B:
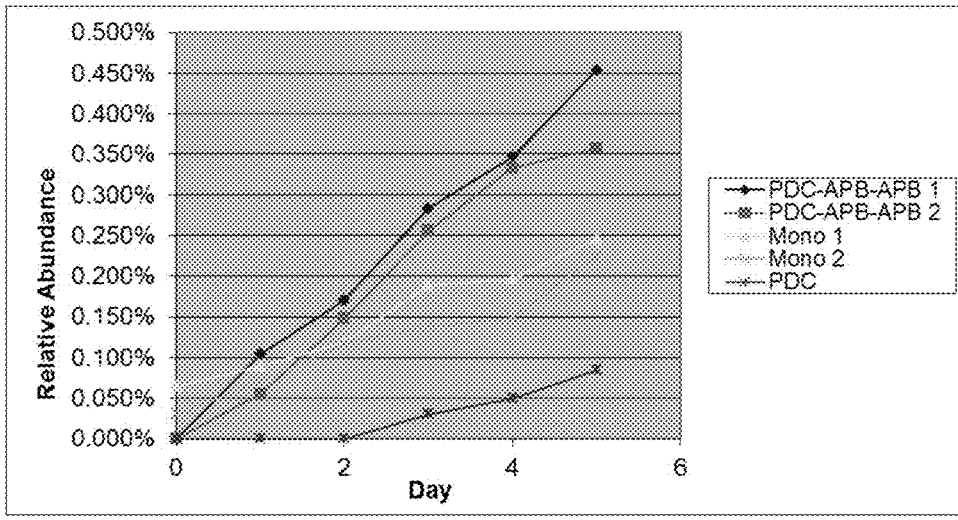
FIG. 21A: Purity analysis HPLC 12% benzyl alcohol in sesame seed (SS) oil, peak area and relative abundance.
FIG. 21B: Purity analysis HPLC 12% benzyl alcohol in SS oil, relative abundance.
Figures 22A, 22B:
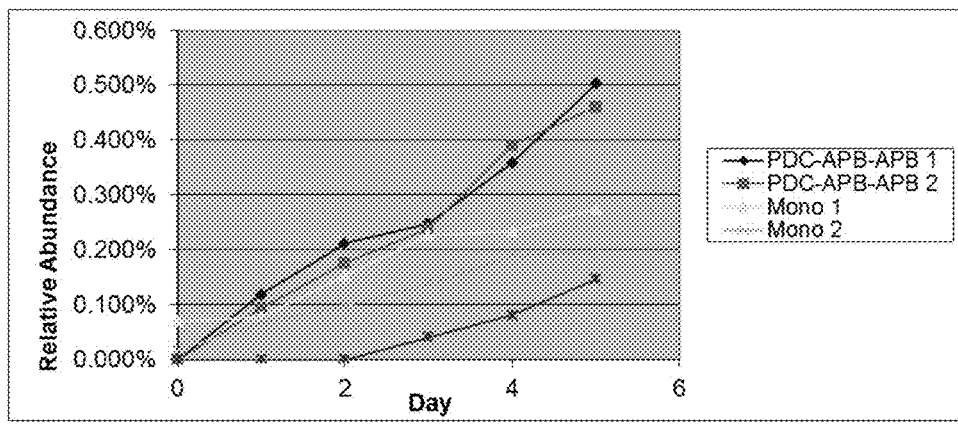
FIG. 22A: Purity analysis HPLC 11% benzyl alcohol in sesame seed (SS) oil, peak area and relative abundance.
FIG. 22B: Purity analysis HPLC 11% benzyl alcohol in SS oil, relative abundance.
Figure 23B:
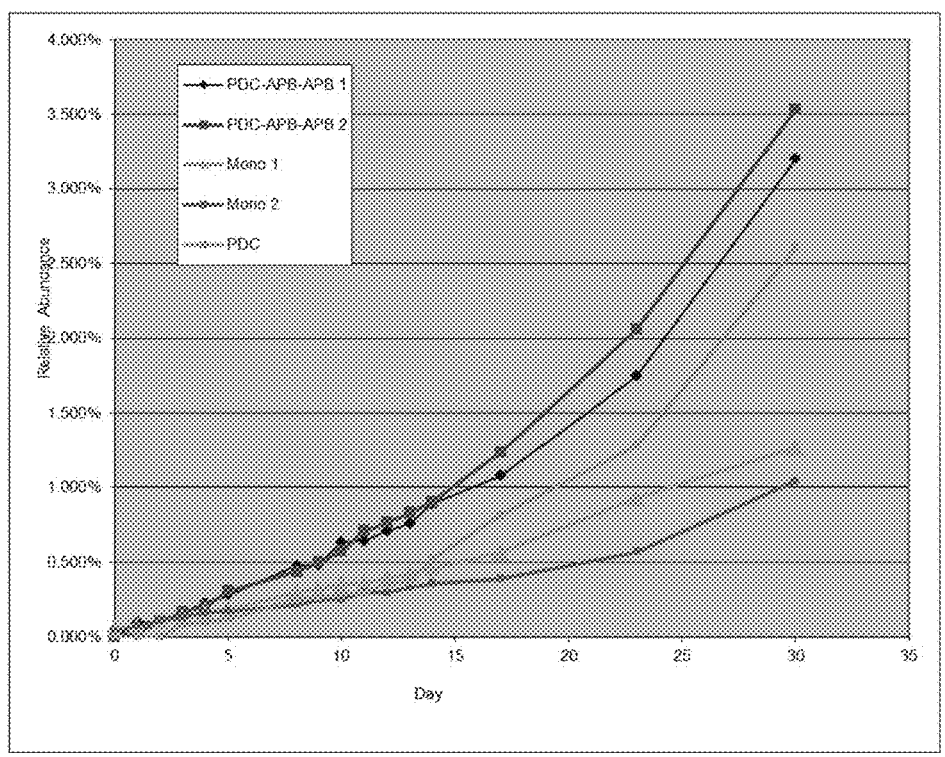
FIG. 23B: Purity analysis HPLC 5% Ethanol, 10% benzyl alcohol in SS oil, relative abundance.
Figure 24B:
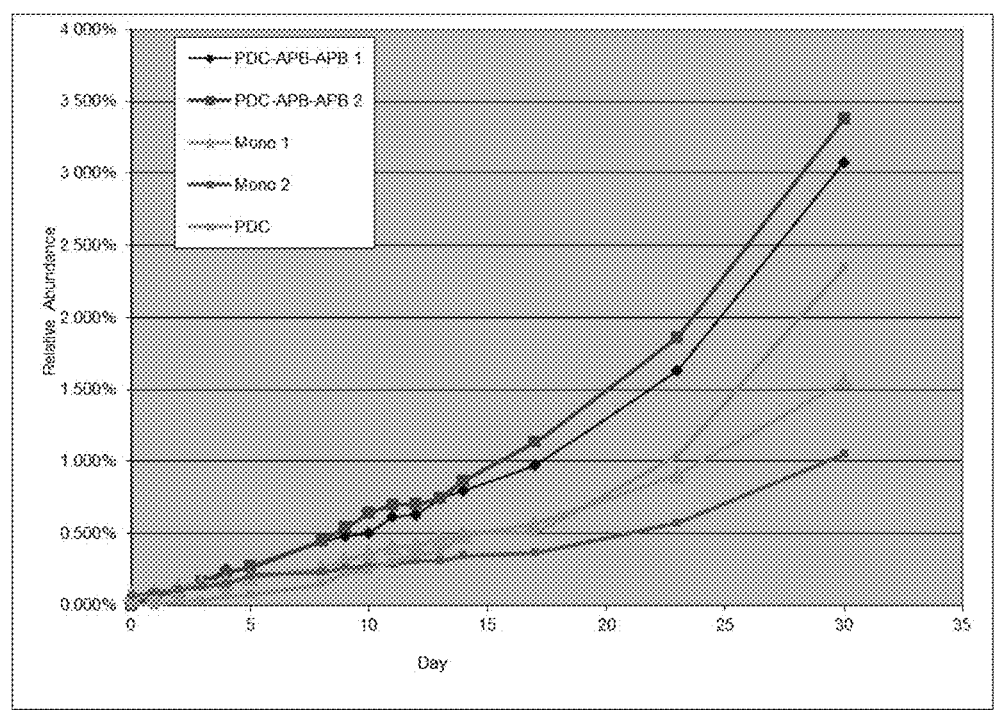
FIG. 24B: Purity analysis HPLC 10% Ethanol, 10% benzyl alcohol in sesame seed (SS) oil, relative abundance.
Figures 25A, 25B:
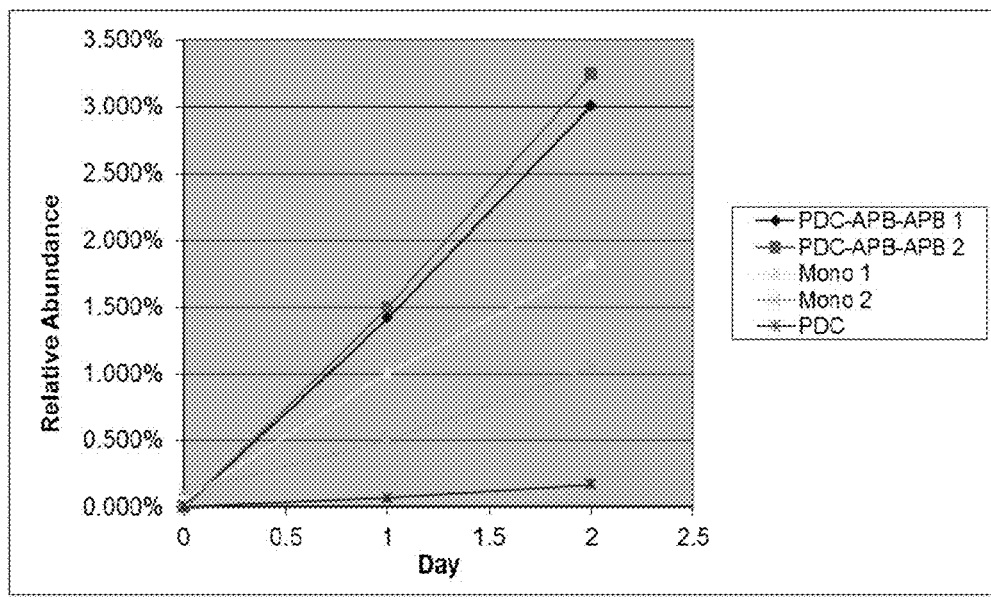
FIG. 25A: Purity analysis HPLC 20% benzyl benzoate in sesame seed (SS) oil, peak area and relative abundance.
FIG. 25B: Purity analysis HPLC 20% benzyl benzoate in sesame seed (SS) oil, relative abundance.
Figures 26A, 26B:
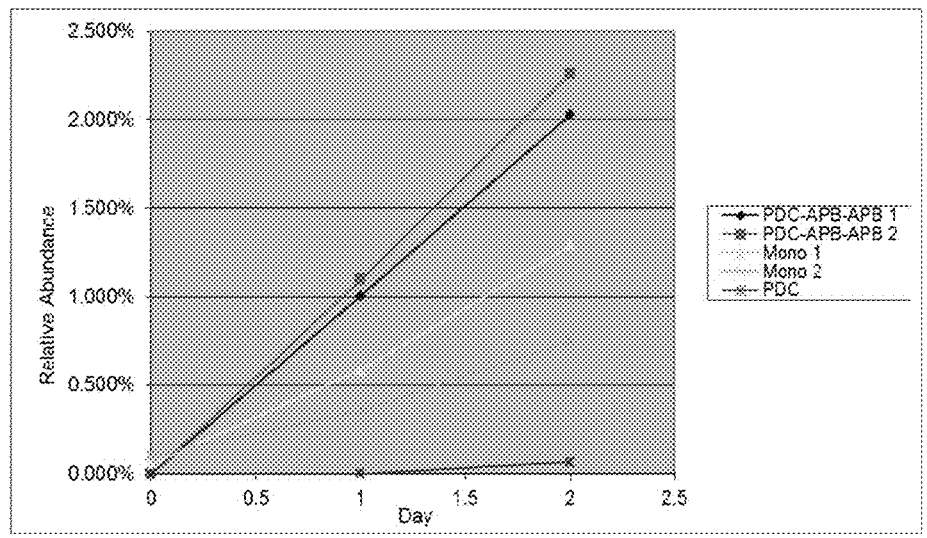
FIG. 26A: Purity analysis HPLC 10% benzyl benzoate in sesame seed (SS) oil, peak area and relative abundance.
FIG. 26B: Purity analysis HPLC 10% benzyl benzoate in sesame seed (SS) oil, relative abundance.
Figure 27B:
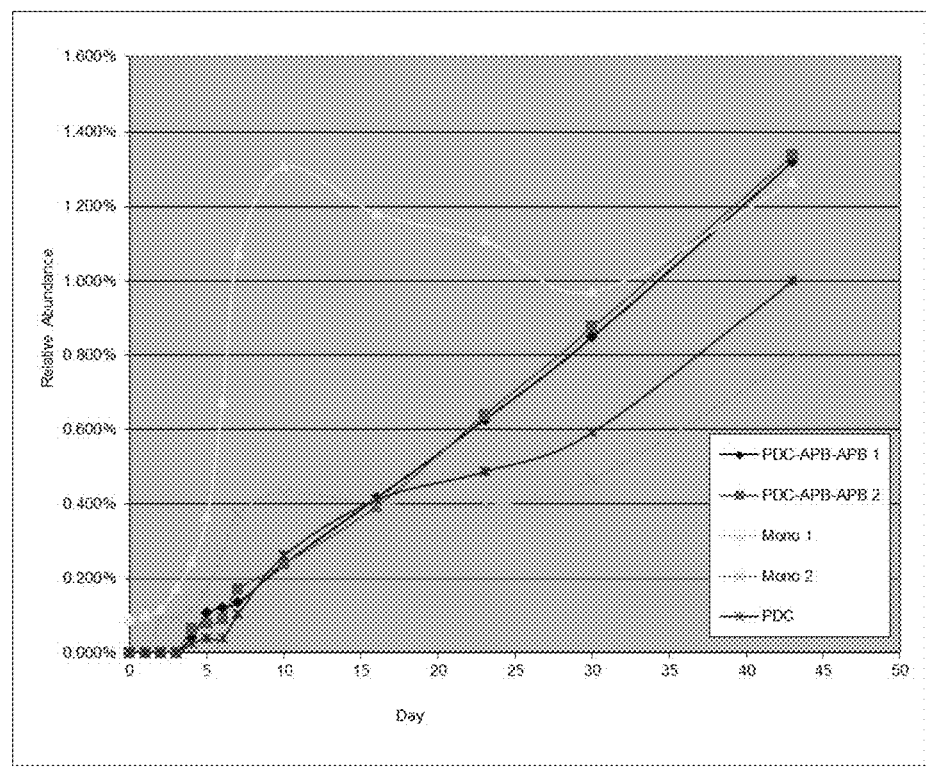
FIG. 27B: Purity analysis HPLC 8% Ethanol, 2% benzyl alcohol in sesame seed (SS) oil, relative abundance.
Figure 28B:
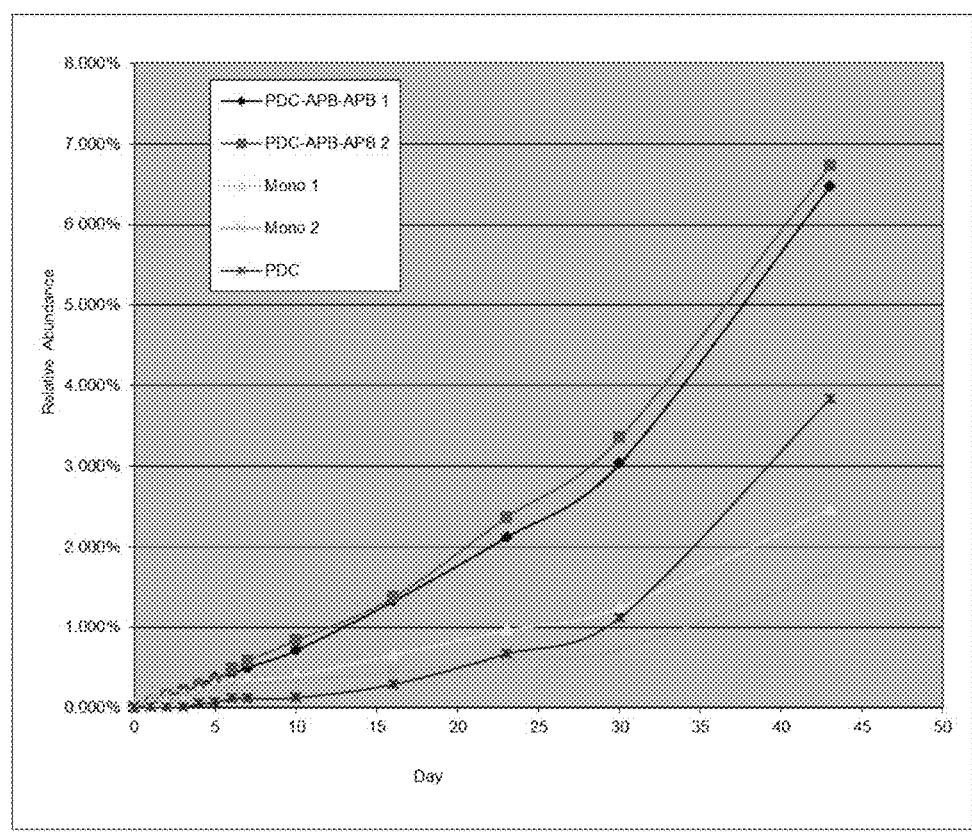
FIG. 28B: Purity analysis HPLC 10% Ethanol, 2% benzyl alcohol in sesame seed (SS) oil, relative abundance.

Application sites of urushiol challenge doses on abdominal skin are shown in FIG. 9, and are described below.

Group I. Animals in this group were given the compound (4) (HDC 4-(4-aminophenyl) butyrate ester) via the intramuscular (IM) route; 300 ul of the equivalent of 20 mg/mL solution of the free catechol in 5% ethanol in each hind leg. Two weeks later these animals were sensitized with urushiol (100 uL acetone containing 1.0 mg of urushiol) on the surface skin in the neck region. Two weeks later the animals were challenged with urushiol (15 uL volume acetone containing 3.0 ug, 4.5 ug or 6.0 ug) on the abdominal skin in a volume of 15 uL. The vehicle contained 15 uL of acetone (see diagram 2). The animals were tested 3 times after sensitization: Test #1 at two weeks post sensitization, test #2 conducted at four weeks post sensitization and test #3 was conducted twelve weeks post sensitization.

Group II. Animals were given 300 uL of the equivalent of 20 mg/mL solution of the free catechol in 5% ethanol of HDC Phenyl alaninate ester (compound 3) via the IM route in each hind leg (total 600 uL). This was followed by sensitization with urushiol on the neck, and then tested with urushiol challenge on the abdominal skin as described for group I.

Group III. Animals were given 300 uL of the equivalent of 20 mg/mL solution of the free catechol in 5% ethanol of HDC Hemiglutarate ester (compound 5) via the IM route in each hind leg. This was followed, two weeks later, by sensitization with (urushiol 100 uL) on the neck, followed by abdominal skin test as described for group I.

Group IV. Animals were given 300 uL of vehicle (5% ethanol) via the IM route in each of the hind legs. This was followed, two weeks later, by sensitization and then followed by abdominal skin test as described for group I.

Group V. Animals in this group were given PBS (300 uL in each of the hind legs) via the IM route. This was followed two weeks later by sensitization and then followed by abdominal skin test as described for group I.

After challenging the animals with urushiol on their abdominal skin, the severity of Erythema and Edema were observed and scored according to the Draize scoring system as shown below. The scores were recorded at 24, 48 and 72 hrs post urushiol skin application.

| Skin Lesion Observed | Score |
|---|---|
| No Erythema | 0 |
| Very Slight (Barely perceptible) Erythema | 1 |
| Well defined Erythema | 2 |
| Moderate to severe Erythema | 3 |
| Severe Erythema (beet red) Eschar formation (deep injury) | 4 |
| No Edema | 0 |
| Very slight edema (barely perceptible) | 1 |
| Well defined (edges of area will defined by definite raising) | 2 |
| Moderate edema (area raised approximately 1 mm) | 3 |
| Severe Edema (raised more than 1 mm and extending beyond area of exposure) | 4 |

Maximum summed Erythema and Edema Scores = 8

RESULTS: The results are given in Tables 1A, B, C (for scores at 24, 48 and 72 hour post challenge respectively) through Tables 3A, B, C and FIGS. 1A, B, C through 3A, B, C. (Pictures taken at 72 hours post urushiol challenge from test #3 are also shown in FIG. 4A-E for illustration of the severity of reaction in the untreated groups IV and V relative to the treated groups I, II and III).

Test #1: The three treated groups of guinea pigs Groups I, II and III when challenged with different doses (3.0 ug, 4.5 ug and 6.0 ug) of urushiol on the abdominal skin did not show any or showed very slight erythema at the exposure site either at 24, 48 or 72 hrs post challenge. In contrast, animals of group IV and V showed varying degrees of erythema and edema. At 24 hours, the skin lesion score in group IV was lower than that of group V at challenge doses of 3.0 and 4.5 ug urushiol. However, there was no difference in the scores of these two groups at the challenge dose of 6.0 ug. As expected the vehicle (acetone) showed no reaction. At 48 hours post challenge, no erythema or edema was observed in the three prophylactic treated groups I, II and III. The skin lesion scores of these groups remained below 1.0. In groups IV and V the lesion scores were higher with the increasing concentration of urushiol challenge. In groups IV and V the skin lesion scores were comparable but tended to be slightly higher in group V. At 72 hours post challenge, no erythema or edema was observed in groups I, II and III. The skin lesion score remained below 1.0. In groups IV and V the skin lesion score were comparable but tended to be slightly higher in group V.

Comparison of lesion scores of groups IV and V at different time points indicates that maximum erythema and edema was observed at 48 hours. At 72 hrs the lesions tended to subside compared to that at 48 hours.

Test #2: This test was conducted two weeks after test #1. At 24 hours, the skin lesion score of group I, II and III (prophylactically treated) was below 1.0. In group IV (vehicle) the scores were 2.5, 3.0 and 3.5 when exposed to urushiol doses of 3.0, 4.5 and 6.0 ug, respectively. In group V the scores were 1.0, 4.0 and 6.5 with urushiol doses of 3.0, 4.5 and 6.0 ug, respectively. At 48 hours, group I showed a total score of 1.5 at the challenge doses of 4.5 or 6.0 ug urushiol. The skin lesion score of animals in group II did not exceed 1.0. In group III the total score was 1.0 and 2.5 with urushiol doses of 4.5 and 6.0 ug, respectively. These scores were comparatively lower than those of groups IV and V. In group V the total scores were 1.0, 4.0 and 6.5 in response to urushiol doses of 3.0, 4.5 and 6.0 ug, respectively.

At 72 hours, the lesions tended to regress. The total lesion score in groups I and II did not exceed 1.0 and in group III regressed to a maximum of 2.0. In groups IV and V the skin lesion scores regressed and ranged between 0.5 and 2.0. Comparatively, these scores were relatively higher than in the prophylactically treated groups I, II and III.

Test #3: This test was conducted approximately seven weeks after the last test #2. At 24 hours group I, II and III did not show erythema or edema at the site of urushiol challenge at any of the doses used. Animals in groups IV showed lesion scores of 2.0, 5.0 and 9.0 to the respectively increasing doses used in this study. The scores of skin lesions in group V were comparable to that in group IV, 2.5, 4.0 and 7.0 to the respective doses of urushiol used.

At 48 hours, the lesion score in group I and III remained below 1.0 and in group II did not exceed 1.0. However, in groups IV and V the skin lesions were, relatively, more pronounced; in group IV the sum of lesion score was 11.5, 20.5 and 29.5 to the respective doses of urushiol used. Similarly, the lesion scores in group V summed up to 6.0, 16.0 and 23.5 to the three respective doses of urushiol challenge.

At 72 hours, the scores in groups I, II and III regressed to below 1.0 or did not exceed 1.0. In contrast, scores of group IV and V remained relatively elevated; in these groups the maximum response to urushiol challenge dose was 28.5 and 22.5 respectively.

The skin lesion scores in group I, II and III in all the 3 tests were negligible compared to those in groups IV and V. This indicates that intramuscular injection of any of the 3 test compounds protected the animals against poison ivy dermatitis. All three compounds were equally effective as no remarkable difference was observed in the skin lesion scores of these three groups.

The skin lesions of groups IV and V in test #1 and test #2 were not as severe compared to that in test #3. It is possible that the massive sensitizing dose of urushiol (1.0 mg) on the neck may have caused a state of "anergy". This condition is observed in patients of tuberculosis (TB) who are burdened with huge amount of TB antigen, but show no reaction to intradermal TB test (False negative). In our experiments, sensitization of animals with massive dose of urushiol may have induced an anergic state for the first two testing periods. However, a rest period of 11 weeks between sensitization and test #3 perhaps reversed the anergic state to a normal reactive state. Thus in test #3, animals in groups IV and V exhibited relatively stronger skin reactions to urushiol challenge; however, animals in group I, II and III were protected due to the prophylactic treatment (see photos of the reactivity of the different groups to the $3^{rd}$ challenge, 72 hour post topical application of test doses).

Synthesis of PDC Amino Acids (Free Bases)
(Valine, Alanine, Glutamine and APB)

Examples 15-18

Scheme 1: General synthesis of PDC-valine, PDC-alanine and PDC-glutamine

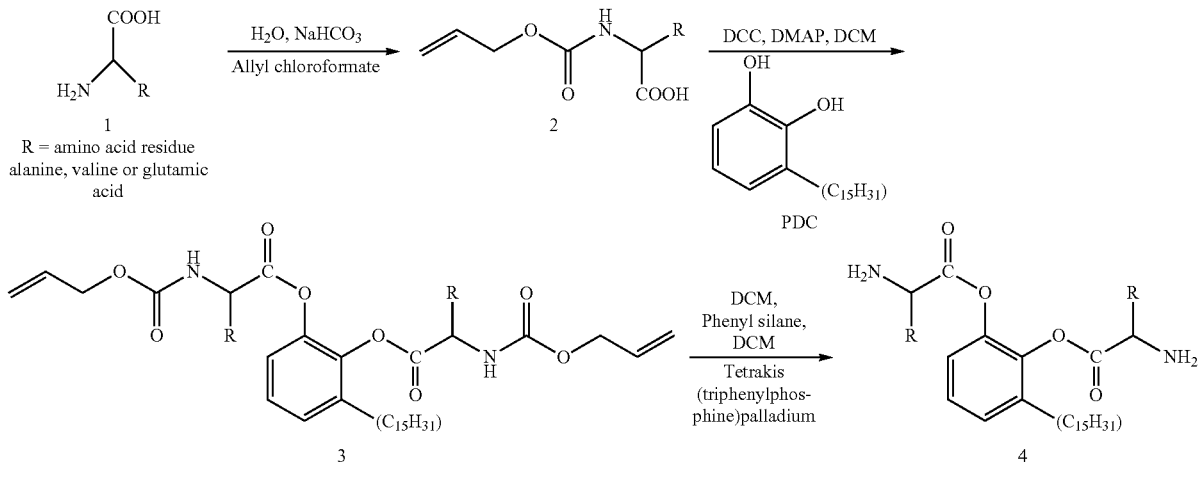

R = amino acid residue alanine, valine or glutamic acid

Example 15

Synthesis of PDC-Valininate

Below is the scheme describing the synthesis of PDC-valininate:

Scheme 2: Synthesis of PDC-valininate

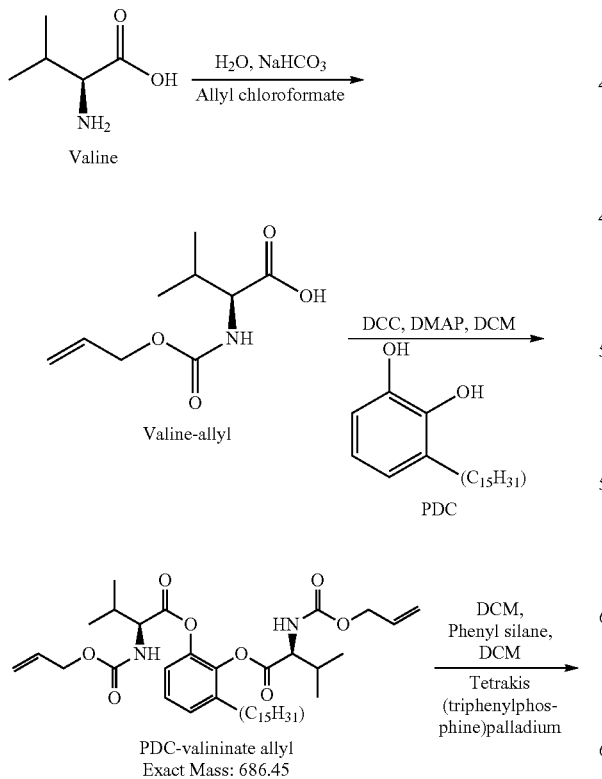

PDC-valininate allyl
Exact Mass: 686.45

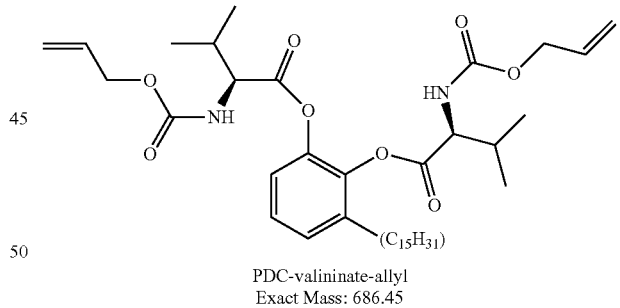

PDC-valininate
Exact Mass: 518.41

Below are the structures for PDC-valininate-allyl and PDC-valininate.

PDC-Valininate-allyl:

PDC-valininate-allyl
Exact Mass: 686.45

PDC-Valininate:

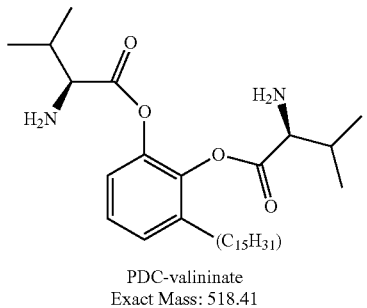

PDC-valininate
Exact Mass: 518.41

Example 16
Synthesis of PDC-Alaninate
Below is the scheme describing the synthesis of PDC-alaninate:
Scheme 2: Synthesis of PDC-alaninate
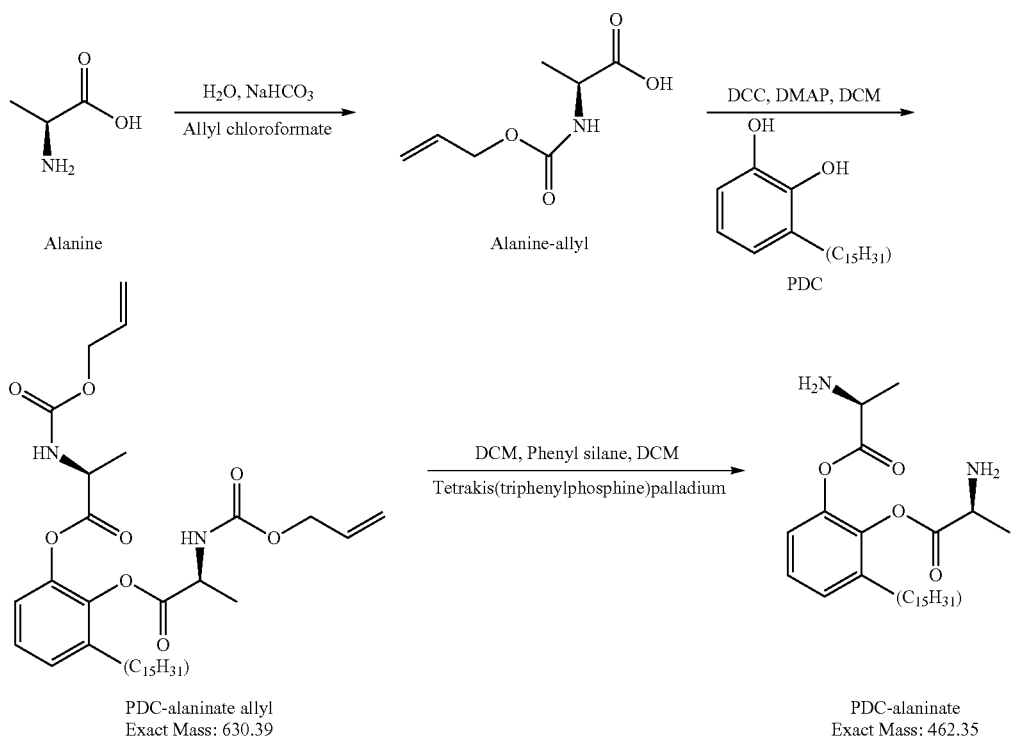
PDC-Alaninate Allyl:
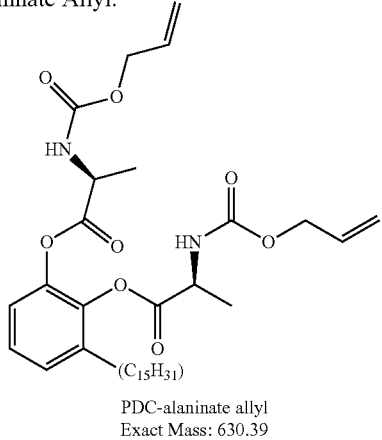
PDC-alaninate allyl
Exact Mass: 630.39
PDC-Alaninate:
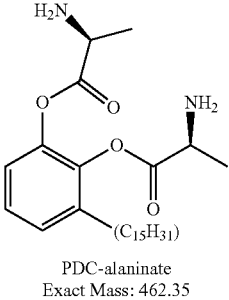
PDC-alaninate
Exact Mass: 462.35
Example 17
Synthesis of PDC-Glutaminate
Scheme 3: Synthesis of PDC-glutaminate
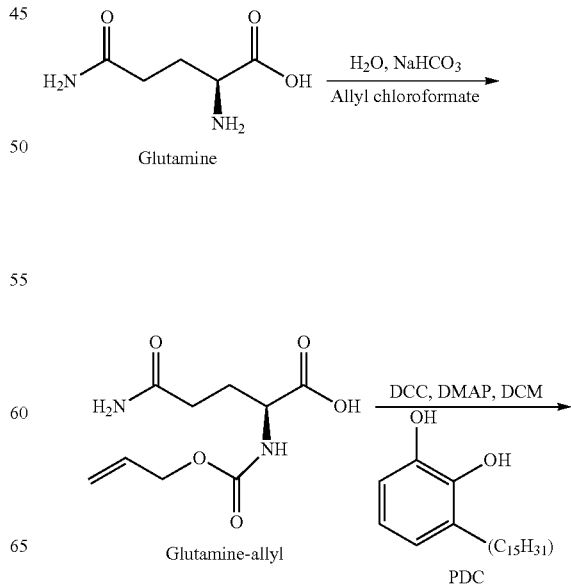

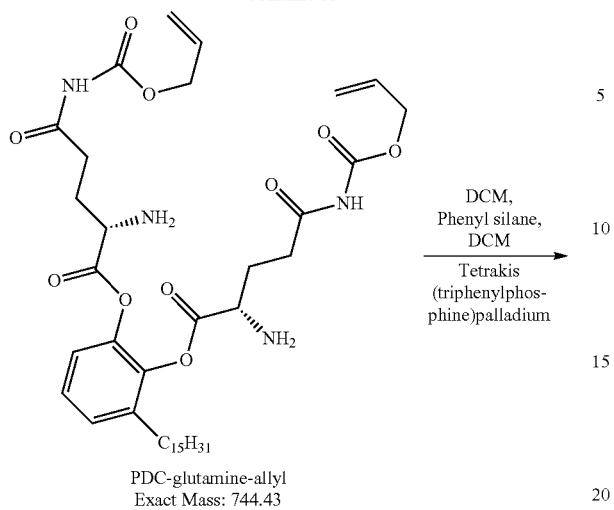

PDC-glutamine-allyl
Exact Mass: 744.43

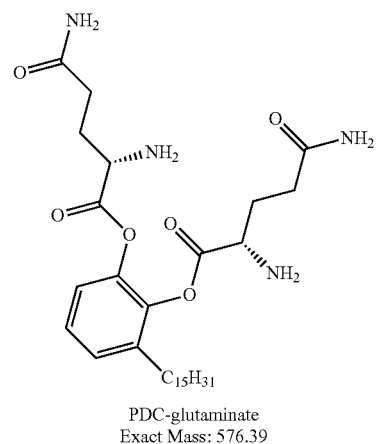

PDC-glutaminate
Exact Mass: 576.39

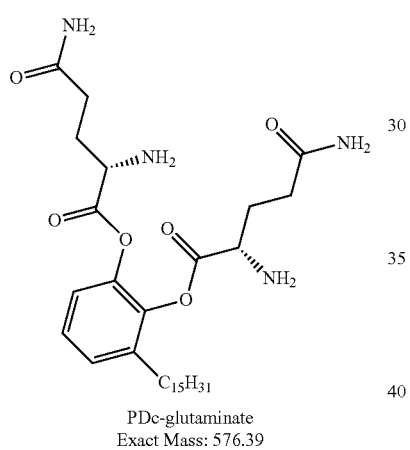

PDc-glutaminate
Exact Mass: 576.39

PDC-Glutaminate Allyl:

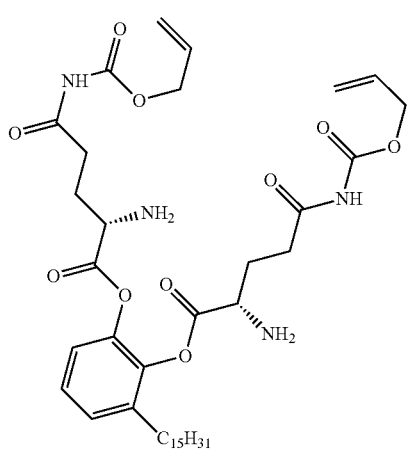

PDC-glutaminate allyl
Exact Mass: 744.431

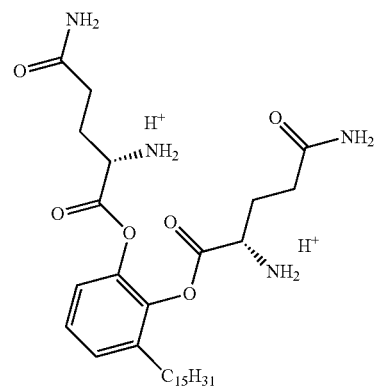

PDC-glutaminate
Exact Mass: 578.40

PDC-Glutaminate:

Example 18

Preparation of 3-Pentadecyl-1,2-phenylene bis(4-(4-aminophenyl)butanoate IPDC-APB1

3-Pentadecyl-1,2-phenylene bis(4-(4-aminophenyl)butanoate (PDC-APB) is prepared by attaching 4(4-aminophenyl)butyric acid to 3-n-pentadecyl catechol with the aid of N,N'-dicyclohexylcarbamide (DCC) and catalyst dimethyl amino pyridine (DMAP) in dichloromethane (DCM) as solvent.

Procedure:

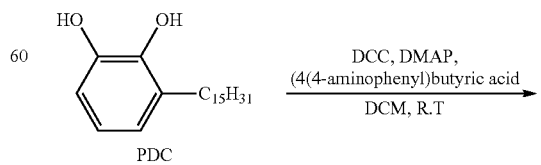

PDC
Chemical Formula: $C_{21}H_{36}O_2$
Exact Mass: 320.27

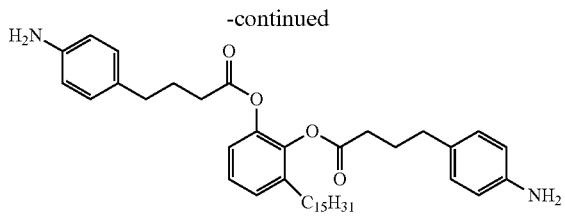

3-pentadecyl-1,2-phenylene bis(4-(4-aminophenyl)butanoate) PDC-APB
Chemical Formula: $C_{41}H_{58}N_2O_4$
Exact Mass: 642.44

A 2.7 g of 3-N-Pentadecyl Catechol (PDC) was dissolved in 50 mL of DCM, 200 mgs of DMAP was added to it and allowed to stir over stirring plate (solution A).

In another flask 2.1 eq (±0.11 eq) of APB and 2.1 eq (±0.11 eq) of DCC was dissolved in DCM. This was allowed to stir for 10 minutes (solution B). Solution A was added to solution B and allowed to stir overnight at room temperature. In the morning, TLC (40% EtOAc in hexanes) indicated the completion of reaction. TLC was developed by using ferric chloride, 10N KOH and heat.

Hexane (25 mL) was added to the reaction mixture and stirred for 5 minutes. Reaction mixture was filtered through filter paper. The solution was evaporated on rotavap and loaded on the silica gel column packed in hexanes. Product was eluted in 35% EtOAc: hexanes, similar fractions were combined, evaporated and purity was determined by HPLC.

Below is the chromatogram of the product showing the purity >95% by UV and >98% by ELSD.

The PDC-APB was subjected to detailed spectroscopic analysis including $^1$H-NMR, carbon, DEPT135.

Different Formulations Preparation of PDC-APB and their Stability Studies

Examples 19-32

Example 19

1% Benzyl Alcohol in SS Oil (ELI-21F-47-1)

PDC-APB (25 mg) was dissolved in 1% benzyl alcohol: sesame seed oil (1 mL) and left in refrigerator overnight. In the morning, on visual inspection, there were crystals. The sample was not analyzed on HPLC and no further investigations were performed.

Example 20

2% Benzyl Alcohol in SS Oil (ELI-21F-47-2)

PDC-APB (25 mg) was dissolved in 2% benzyl alcohol: sesame seed oil (1 mL) and left in refrigerator overnight. In the morning, on visual inspection, there were crystals. The sample was not analyzed on HPLC and no further investigations were performed.

Example 21

5% Benzyl Alcohol in SS Oil (ELI-21F-47-3)

PDC-APB (25 mg) was dissolved in 5% benzyl alcohol: sesame seed oil (1 mL) and left in refrigerator overnight. In the morning, on visual inspection, there were crystals. The sample was not analyzed on HPLC and no further investigations were performed.

Example 22

10% Benzyl Alcohol in SS Oil (ELI-21F-47-4)

PDC-APB (25 mg) was dissolved in 10% benzyl alcohol: sesame seed oil (1 mL) and left in refrigerator overnight. In the morning, on visual inspection, there were no crystals formed. 20 of sample was taken and diluted in 980 µL of tetrahydrofuran and analyzed for purity on HPLC (Day 0). Remaining sample was placed in oven and incubated at 40° C. 20 µL of sample was taken and analyzed for purity after 2, 3, 4, 5, and 6 days. After 6 days, sample was no longer analyzed due to impurities.

Example 23

15 mg/mL in SS Oil (ELI-21F-47-5)

PDC-APB (15 mg) was dissolved in sesame seed oil (1 mL) and left in refrigerator overnight. In the morning, on visual inspection, there were crystals. The sample was not analyzed on HPLC and no further investigations were performed.

Example 24

20 mg/mL in SS Oil (ELI-21F-47-6)

PDC-APB (20 mg) was dissolved in sesame seed oil (1 mL) and left in refrigerator overnight. In the morning, on visual inspection, there were crystals. The sample was not analyzed on HPLC and no further investigations were performed.

Example 25

12% Benzyl Alcohol in SS Oil (ELI-21F-47-7)

PDC-APB (25 mg) was dissolved in 12% benzyl alcohol: sesame seed oil (1 mL) and left in refrigerator overnight. In the morning, on visual inspection, there were no crystals formed. 20 of sample was taken and diluted in 980 µL of tetrahydrofuran and analyzed for purity on HPLC (Day 0). Remaining sample was placed in oven and incubated at 40° C. 20 µL of sample was taken and analyzed for purity after 1, 2, 3, 4, and 5 days. After 5 days, sample was no longer analyzed due to impurities.

Example 26

11% Benzyl Alcohol in SS Oil (ELI-21F-47-8)

PDC-APB (25 mg) was dissolved in 11% benzyl alcohol: sesame seed oil (1 mL) and left in refrigerator overnight. In the morning, on visual inspection, there were no crystals formed. 20 of sample was taken and diluted in 980 µL of tetrahydrofuran and analyzed for purity on HPLC (Day 0). Remaining sample was placed in oven and incubated at 40° C. 20 µL of sample was taken and analyzed for purity after 1, 2, 3, 4, and 5 days. After 5 days, sample was no longer analyzed due to impurities.

Example 27

5% Ethanol+10% Benzyl Alcohol in SS Oil
(ELI-21F-47-9)

PDC-APB (25 mg) was dissolved in 5% ethanol: 10% benzyl alcohol: sesame seed oil (1 mL) and left in refrigerator overnight. In the morning, on visual inspection, there were no crystals formed. 20 µL of sample was taken and diluted in 980 µL of tetrahydrofuran and analyzed for purity on HPLC (Day 0). Remaining sample was placed in oven and incubated at 40° C. 20 µL of sample was taken and analyzed for purity after 1, 2, 3, 4, 5, 8, 9, 10, 11, 12, 13, 14, 17, 23, and 30 days. After 30 days, sample was no longer analyzed due to impurities.

Example 28

10% Ethanol+10% Benzyl Alcohol in SS Oil
(ELI-21F-47-10)

PDC-APB (25 mg) was dissolved in 10% ethanol: 10% benzyl alcohol: sesame seed oil (1 mL) and left in refrigerator overnight. In the morning, on visual inspection, there were no crystals formed. 20 µL of sample was taken and diluted in 980 µL of tetrahydrofuran and analyzed for purity on HPLC (Day 0). Remaining sample was placed in oven and incubated at 40° C. 20 mL of sample was taken and analyzed for purity after 1, 2, 3, 4, 5, 8, 9, 10, 11, 12, 13, 14, 17, 23, and 30 days. After 30 days, sample was no longer analyzed due to impurities.

Example 29

20% Benzyl Benzoate in SS Oil (ELI-21F-49-5)

PDC-APB (25 mg) was dissolved in 20% benzyl benzoate: sesame seed oil (1 mL) and left in refrigerator overnight. In the morning, on visual inspection, there were no crystals formed. 20 µL of sample was taken and diluted in 980 µL of tetrahydrofuran and analyzed for purity on HPLC (Day 0). Remaining sample was placed in oven and incubated at 40° C. 20 µL of sample was taken and analyzed for purity after 1 and 2 days. After 2 days, sample was no longer analyzed due to impurities.

Example 30

10% Benzyl Benzoate in SS Oil (ELI-21F-49-6)

PDC-APB (25 mg) was dissolved in 10% benzyl benzoate: sesame seed oil (1 mL) and left in refrigerator overnight. In the morning, on visual inspection, there were no crystals formed. 20 µL of sample was taken and diluted in 980 µL of tetrahydrofuran and analyzed for purity on HPLC (Day 0). Remaining sample was placed in oven and incubated at 40° C. 20 µL of sample was taken and analyzed for purity after 1 and 2 days. After 2 days, sample was no longer analyzed due to impurities.

Example 31

8% Ethanol+2% Benzyl Alcohol in SS Oil
(ELI-21F-52-2)

PDC-APB (25 mg) was dissolved in 8% ethanol: 2% benzyl alcohol: sesame seed oil (1 mL) and left in refrigerator overnight. In the morning, on visual inspection, there were no crystals formed. 20 µL of sample was taken and diluted in 980 µL of tetrahydrofuran and analyzed for purity on HPLC (Day 0). Remaining sample was placed in oven and incubated at 40° C. 20 µL of sample was taken and analyzed for purity after 1, 2, 3, 4, 5, 6, 7, 10, 16, 23, 30, and 43 days.

Example 32

10% Ethanol+2% Benzyl Alcohol in SS Oil
(ELI-21F-53-2)

PDC-APB (25 mg) was dissolved in 10% ethanol: 2% benzyl alcohol: sesame seed oil (1 mL) and left in refrigerator overnight. In the morning, on visual inspection, there were no crystals formed. 20 µL of sample was taken and diluted in 980 µL of tetrahydrofuran and analyzed for purity on HPLC (Day 0). Remaining sample was placed in oven and incubated at 40° C. 20 µL of sample was taken and analyzed for purity after 1, 2, 3, 4, 5, 6, 7, 10, 16, 23, 30, and 43 days.

Safety and Efficacy Studies on PDC-APB (Examples 34 and 35) this is OK Since it's Only the Title of this Section and the Examples are Correctly Labelled Rabbit Muscle Irritability Study for PDC-APB

Example 34

Start date: Nov. 3, 2014. End date: Dec. 2, 2014
Number of rabbits=6
Formulations prepared at ELI were given IM to rabbits in hind legs.

Vehicle (ELI-21F-67-VEH)

Ethanol (3.2 mL) 200 proof (AADER) was added to 36 mL of super refined sesame seed oil NF NP-SR40280 Lot#0007082185. To this mixture, an 0.8 mL of benzyl alcohol, Fisher (A-396) was added. The resultant oil/alcohol mixture (40 mL) was then sonicated for 5 minutes to make it uniform. The resultant solution was filtered through Whatman 0.2 µm PP filter to produce vehicle (ELI-21F-67-VEH).

ELI-21F-67-1 (25 mg/mL)

PDC-APB (350 mgs; CX252, P239-104-21) was weighed and 14 mL of vehicle (ELI-21F-67-VEH) was added to it. It was Sonicated and filtered through 0.2 µm filter producing ELI-21F-67-1 (25 mg/mL).

ELI-21F-67-2 (8.33 mg/mL)

ELI-21F-67-1 (2.5 mL) was taken and 5 mL of vehicle (ELI-21F-67-VEH) was added to it. It was sonicated and filtered through Whatman 0.2 µm filter to produce 8.33 mg/mL PDC-APB solution (ELI-21F-67-2).

ELI-21F-67-3 (2.5 mg/mL)

ELI-21F-67-1 (1 mL) was taken and 9 mL of vehicle (ELI-21F-67-VEH) was added to it. It was sonicated and filtered through Whatman 0.2 µm filter to produce 2.5 mg/mL PDC-APB solution (ELI-21F-67-3).

| | | |
|---|---|---|
| 1. (S) | Saline; Volume injected = 1.0 ml in each hind leg. | |
| 2. (V) | Vehicle; ELI-21F-67-VEH. Volume injected = 1.0 ml in each hind leg. | |
| 3. (A 1.0) | ELI-21F-67-1; 25 mg/ml; Volume injected = 1.0 ml in each hind leg. | |
| 4. (A 0.5) | ELI-21F-67-1; 25 mg/ml; Volume injected = 0.5 ml in each hind leg. | |
| 5. (B) | ELI-21F-67-2; 8.33 mg/ml; Volume injected = 1.0 ml in each hind leg. | |
| 6. (C) | ELI-21F-67-3; 2.5 mg/ml; Volume injected = 1.0 ml in each hind leg. | |

Procedure: Area for the injection site in the hind legs was shaved and marked with a permanent marker. Intramuscular injections were given with a 28 gauge needle on days 1, 14 and 28. Animals were examined to observe for any erythema or swelling at the site of injection. Muscles around the site of injection were palpated for stiffness or hard mass at different times, especially at 24 and 48 hrs post injections during the course of treatments. The observations were scored as described in the table 1. On day 29, all animals were euthanized. Their blood was collected for clinical chemistry and CBC (complete blood count).

TABLE 1

Scoring scheme for observations at the site of injection in muscle

| Score | Swelling | Redness | Stiffness | Hard mass |
|---|---|---|---|---|
| 0 | No | No | No | No |
| 1 | Slight | Slight | Slight | Slight |
| 2 | Moderate | Moderate | Moderate | Moderate |
| 3 | Marked | Marked | Marked | Marked |
| 4 | Extreme | Extreme | Extreme | Extreme |

Results and Comments: The injection site on all animals did not show any sign of erythema, swelling or edema. The animals did not show any sign of pain during the course of the study. All observations are given in Table 2.

In animal #3 (A 1.0) and animal #4 (A 0.5), at 24 hrs post $2^{nd}$ injection, a small mass (slight to moderately hard) could be palpated above the site of injection. This was palpable in both legs. At 48 hrs post injection the hard mass could still be palpated but to a lesser degree. A week later, no hard mass was palpable. This could be enlargement of popliteal lymph nodes in these animals and may have occurred in response to the dose administered to these rabbits. Before administration of the $3^{rd}$ injection none of the animals showed any hard mass in their muscle.

At necropsy, the site of injection appeared normal. There was no mass felt on palpation of the muscles around the site of injection. No visible difference could be observed in the muscle tissue at the site of injection among the rabbits given different treatments. The hind legs of all rabbits were removed from stifle joint to the pelvic joint. These were placed in 10% buffered formalin for 72 hrs. before shipping them to Experimur (Chicago Ill.).

The results of blood chemistry and blood counts are given in Table 3 and 4 respectively. All parameters remained within normal ranges.

TABLE 2

Observations scored during the course of experiment (R: Right Leg; L: Left Leg)

| Date | | Group S | | Group V | | Group $A_1$ | | Group $A_{0.5}$ | | Group B | | Group C | |
|---|---|---|---|---|---|---|---|---|---|---|---|---|---|
| | | R | L | R | L | R | L | R | L | R | L | R | L |
| Nov. 2, 2014 | Swelling | 0 | 0 | 0 | 0 | 0 | 0 | 0 | 0 | 0 | 0 | 0 | 0 |
| | Redness | 0 | 0 | 0 | 0 | 0 | 0 | 0 | 0 | 0 | 0 | 0 | 0 |
| | Stiffness | 0 | 0 | 0 | 0 | 0 | 0 | 0 | 0 | 0 | 0 | 0 | 0 |
| | Hard Mass | 0 | 0 | 0 | 0 | 0 | 0 | 0 | 0 | 0 | 0 | 0 | 0 |
| Nov. 3, 2014 | | 1st Injection | | | | | | | | | | | |
| Nov. 4, 2014 (24 hrs post $1^{st}$ injection) | Swelling | 0 | 0 | 0 | 0 | 0 | 0 | 0 | 0 | 0 | 0 | 0 | 0 |
| | Redness | 0 | 0 | 0 | 0 | 0 | 0 | 0 | 0 | 0 | 0 | 0 | 0 |
| | Stiffness | 0 | 0 | 0 | 0 | 0 | 0 | 0 | 0 | 0 | 0 | 0 | 0 |
| | Hard Mass | 0 | 0 | 0 | 0 | 0 | 0 | 0 | 0 | 0 | 0 | 0 | 0 |
| Nov. 5, 2014 | | No altered conditions was found at the site of injection | | | | | | | | | | | |
| Nov. 14, 2014 | | (3 days before $2^{nd}$ injection) All animals appeared normal | | | | | | | | | | | |
| Nov. 17, 2014 | | $2^{nd}$ Injection | | | | | | | | | | | |
| Nov. 18, 2014 (24 hrs post $2^{nd}$ injection) | Swelling | 0 | 0 | 0 | 0 | 0 | 0 | 0 | 0 | 0 | 0 | 0 | 0 |
| | Redness | 0 | 0 | 0 | 0 | 0 | 0 | 0 | 0 | 0 | 0 | 0 | 0 |
| | Stiffness | 0 | 0 | 0 | 0 | 0 | 0 | 0 | 0 | 0 | 0 | 0 | 0 |
| | Hard Mass | 0 | 0 | 0 | 0 | 2 | 2 | 2 | 1 | 0 | 0 | 0 | 0 |
| Nov. 19, 2014 (48 hrs post $2^{nd}$ injection) | Swelling | 0 | 0 | 0 | 0 | 0 | 0 | 0 | 0 | 0 | 0 | 0 | 0 |
| | Redness | 0 | 0 | 0 | 0 | 0 | 0 | 0 | 0 | 0 | 0 | 0 | 0 |
| | Stiffness | 0 | 0 | 0 | 0 | 0 | 0 | 0 | 0 | 0 | 0 | 0 | 0 |
| | Hard Mass | 0 | 0 | 0 | 0 | 1 | 1 | 1 | 0 | 0 | 0 | 0 | 0 |
| Nov. 26, 2014 | | All Rabbits were normal. No altered condition was found at the site of injection | | | | | | | | | | | |
| Dec. 1, 2014 | | $3^{rd}$ Injection | | | | | | | | | | | |
| Dec. 2, 2014 | Swelling | 0 | 0 | 0 | 0 | 0 | 0 | 0 | 0 | 0 | 0 | 0 | 0 |
| | Redness | 0 | 0 | 0 | 0 | 0 | 0 | 0 | 0 | 0 | 0 | 0 | 0 |

TABLE 2-continued

Observations scored during the course of experiment (R: Right Leg; L: Left Leg)

| Date | | Group S | | Group V | | Group A₁ | | Group A₀.₅ | | Group B | | Group C | |
|------|------|---|---|---|---|---|---|---|---|---|---|---|---|
| | | R | L | R | L | R | L | R | L | R | L | R | L |
| | Stiffness | 0 | 0 | 0 | 0 | 0 | 0 | 0 | 0 | 0 | 0 | 0 | 0 |
| | Hard Mass | 0 | 0 | 0 | 0 | 0 | 0 | 0 | 0 | 0 | 0 | 0 | 0 |
| Dec. 2, 2014 | | All Animals were Sacrificed as per the protocol | | | | | | | | | | | | |

Efficacy Study on Two Formulations Containing PDC-APB for Prophylaxis Against Poison Ivy Dermatitis Example 35

June-August 2014

Objective: To determine the efficacy of two formulations for prevention of poison ivy induced dermatitis.

Sensitization: Guinea pigs were obtained from certified vendor and housed in cages in the UM vivarium and kept in 12 hour day and night cycle. Food and water was provided ad libitum. These were sensitized with 100 UL of poison ivy Urushiol (1.0 mg/ml) on their skin in the neck region. The animals were rested for 2 weeks and then challenged with 3.0, 4.5 and 6.0 ug of poison ivy urushiol in 10 uL of acetone on their shave d abdominal skin. Skin reaction was scored for erythema and edema and the responders were identified. The responder animals were randomly divided in three groups (n=7 per group), with each group mean erythema+edema score was comparable.

Inoculation: Two weeks post sensitization and selection of responder animals, intramuscular inoculation of formulations was done as under:

ELI-21F-45-1

PDC-APB (60 mg; CX252, P239-104-21) was weighed. Super refined sesame seed oil (6 mL) NF NP-LQ-(MH) Lot # SR40280 was added. It was Sonicated to dissolve and filtered through a 0.2 μm filter producing ELI-21F-45-1 (10 mg/mL).

ELI-21F-45-2

ELI-21F-45-1 (1 mL) was taken and filtered with Super refined sesame seed oil (4 mL) NF NP-LQ-(MH) Lot # SR40280 was added. The product was ELI-21F-45-2 (2 mg/mL).

ELI-21F-45-3

PDC-APB (20 mg; CX252, P239-104-21) was weighed and 300 μL EtOH, 1500 μL BASF (Kolliphor ELP, Lot #05004375L0) and 4200 μL injectable water was added. It was mixed well then filtered through 0.2 μm filter. The product was ELI-21F-45-3 (3.3 mg/mL).

Group 1 was inoculated IM with the vehicle (SS Oil); A volume of 300 uL in each hind leg.

Group 2 was inoculated IM with ELI-21F-45-1 (10 mg/ml); A volume of 300 uL in each hind leg.

Group 3 was inoculated IM with ELI-21F-45-2 (2.0 mg/ml); A volume of 300 uL in each hind leg.

Three groups of guinea pigs (n=7 per group) were given IM 300 uL of the formulations in each hind legs. Total volume injected was 600 uL per guinea pigs.

Challenge: All guinea pigs were challenged with poison ivy Urushiol (3, 4.5 and 6.0 ug) on their abdominal skin at 3 (challenge#1) and 5 weeks (challenge #2) post inoculation. Their erythema and edema scores were recorded at 24, 48 and 72 hours post each challenge.

Results: FIGS. 1 A-C shows the skin reaction and scores at 24, 48 and 72 hrs post challenge#1. The strongest reaction was observed in the vehicle treated group. The two treated groups (group 2, IM injection ELI-21F-45-1; 10 mg/ml and group 3 IM injection ELI-21F-45-2; 2.0 mg/ml) showed significantly ($p<0.05$) less reaction compared to the control (vehicle) group 1.

FIG. 2 A-C show shows the skin reaction and scores at 24, 48 and 72 hrs post challenge #2. While the vehicle group showed strong reaction to Urushiol challenge, the treated groups (group 2 and group 3) showed a very mild reaction that was statistically ($p<0.01$ or $p<0.05$) less than the vehicle group Conclusion: In conclusion both formulations ELI-21F-45-1 (10 mg/ml) and ELI-21F-45-1 (2.0 mg/ml) showed significant protection against poison ivy Urushiol induced skin reaction.

REFERENCES

1. Praiser, D. M., Ceilley, R. I., Lefkovits, A. M., Katz, B. E and Paller, A. S. 2003. Poison ivy, oak and sumac, Derm. Insights. 4:26-18.
2. ElSohly, M. A., Benigni, D. A., Torres, L. and Watson, E. S. 1983. Synthesis and Antiallergenic Properties of 3-n-Pentadecyl- and 3-n-Heptadecylcatechol Esters. Journal of Pharmaceutical Sciences. 72:792-795.
3. Marks, J. G. and Deleo, V. A. 1992. Contact and occupational dermatology. p. 213-217. Moby-Year Book. St Louis.
4. Marks, J. G. 1989. Poison ivy and poison oak allergic contact dermatitis. J. Allergy Clin Immunol. 9:497-506.
5. Fisher, A. A. and Mitchell, J. C. 1995. Toxicodendron plants and species. In: Rietschel R L, ed. Fisher's Contact Dermatitus. 4th ed. Baltimore, Md.: Williams & Wilkins. 461-523.
6. Epstein, W. L. 1987. The poison ivy picker of pennypack park: the continuing saga of poison ivy. J Invest Dermatol. 88 (suppl 3) 7-11.
7. Epstein, W. L. 1994. Occupational poison ivy and oak dermatitis. Dermatol Clin. 12:511-516.
8. Gladman, A. C. 2006. Toxicodendron Dermatitis: Poison Ivy, Oak and Sumac. Wilderness and Enviromental Medicine, 17:120-128.
9. Symes, W. F. and Dawson, C. R. 1954. Poison ivy urushiol. J. Am. Chem. Soc. 76:2959-2963.

10. Sunthankar, S. V. and Dawson, C. R. 1954. The structural identification of the olefinic components of Japanese Lac urushiol. J. Am. Chem. Soc. 76:5070-5074.
11. Markiewitz, K. H. and Dawson, C. R. 1965. On the Isolation of Allergenically Active Components of the Toxic Principle of Poison Ivy. J. Org. Chem. 30:1610-1613.
12. Billets, S., Craig, J. C., Corbett, M. D. and Vickery, J. F. 1976. Component analysis of urushiol content of poison ivy and poison oak. Phytochemistry. 15: 533-535.
13. Tyman, J. H. P. 1996. Studies in Organic Chemistry 52. p. 465-546. In Synthetic and Natural Phenols. Elsevier.
14. Xia, Z., Miyakoshi, T. and Yoshida, T. 2004. Lipoxygenase-catalysed polymerization of phenolic lipids suggests a new mechanism for allergic contact dermatitis induced by urushiol and its analogs. Biochemical and Biophysical Research Communication. 315:704-709. (references therein)
15. Byck, J. S. and Dawson, C. R. 1968. Assay of protein-quinone coupling involving compounds structurally related to the active principal of poison ivy. Anal. Biochem. 25:123-135.
16. Benezra, C. 1990. Molecular recognition in allergic contact dermatitis to natural products. Pure Appl. Chem. 62:1251-1258.
17. Kalish, R. S. 1991. Recent developments in the pathogenesis of allergic contact dermatitis. Arch. Dermatol. 127:1558-1563.
18. Watson, E. S., Murphy, J. C., Wirth, P. W., ElSohly, M. A. and Skierkowski, P. 1981. Immunological Studies of Poisonous Anacardiaceae: Production of Tolerance in Guinea Pigs using 3-n-Pentadecylcatechol-"Modified" Autologous Blood Cells, Journal of Pharmaceutical Sciences. 70:785-789. (references therein)
19. Sebastiani, S., Albanesi, C., De P O, Puddu, P., Cavani, A, and Girolomoni, G. 2002. The role of chemokines in allergic contact dermatitis. Arch Dermatol Res 293:552-559
20. Sanchez-Sanchez, N., Riol-Blanco, L. and Rodriguez-Fernandez, J. L. 2006. The multiple personalities of the chemokine receptor CCR7 in dendritic cells. J Immunol. 176:5153-5159.
21. Ebert, L. M., Schaerli, P. and Moser, B. 2005. Chemokine-mediated control of T cell traffic in lymphoid and peripheral tissues. Mol Immunol 42:799-809.
22. Akiba, H., Kehren, J., Ducluzeau, M. T., Krasteva, M., Horand, F., Kaiserlian, D., Kaneko, F. and Nicolas, J. F. 2002. Skin Inflammation During Contact Hypersensitivity is Mediated by Early Recruitment of CD8+ T Cytotoxic 1 Cells inducing Keratinocyte Apoptosis. J. Immunol 168:3079-3087.
23. Epstein, W. L. 1989. Topical prevention of poison ivy/oak dermatitis. Arch Dermatol. 125:499-501.
24. Grevelink, S. A., Murrell, D. F. and Olsen, E. A. 1992. Effectiveness of various barrier preparations in preventing and/or ameliorating experimentally produced Toxicodendron dermatitis. J. Am. Acad. Dermatol. 27:182-188.
25. Schwartz, L., Warner, L. H. and Goldman, F. H. 1940. Protective ointment for the prevention of poison ivy dermatitis. Public Health Rep. 55:1327-1333.
26. Shelmire, B. 1941. Sodium perborate ointment and poison ivy dermatitis. JAMA. 116:681-683.
27. Orchard, S. 1984. Barrier creams. Dermatol. Clin. 2:619-629.
28. Orchard, S. M., Fellman, J. H. and Storrs, F. J. 1987. Topical substances which prevent poison ivy Allergic contact dermatitis. Acta Derm Venereol Suppl (Stockh). 134:103-106.
29. Vidmar, D. A. and Iwane, M. K. 1999. Assessment of the Ability of the Topical Skin Protectant (TSP) to Protect Against Contact Dermatitis to Urushiol (Rhus) Antigen. American Journal of Contact Dermatitis. 10:190-197.
30. Sanfilippo, A. M., Barrio, V., Kulp-Shorten, C. and Callen, J. P. 2003. Common Pediatric and Adolescent Skin Conditions. J. Pediatr. Adolesc. Gynecol. 16: 269-283.
31. Kligman, A. M. 1958. Hyposensitization against Rhus dermatitis. Arch Dermatol. 78:47-72.
32. Rietschel, R. L. and Fowler, J. F. 1995. Toxicondendron plants and species. p. 461-523 In Fisher A A, (ed): Fisher Contact Dermatitis (ed 4). Lea & Febiger. Philadelphia, Pa.
33. Epstein, W. L., Baer, H., Dawson, C. R. and Khurana, R. G. 1974. Poison oak hyposensitization evaluation of purified urushiols. Arch. Dermatol. 109:356-360.
34. Stevens, F. A. 1945. Status of poison ivy extracts. JAMA. 127:912-921.
35. Watson, E. S., Murphy, J. C., Wirth, P. W., Waller, C. W. and ElSohly, M. A. 1981. Immunologic Studies of Poisonous Anacardiaceae: 1. Production of Tolerance and Desensitization to Poison Ivy and Oak Urushiols Using Esterified Urushiol Derivatives in Guinea Pigs. The Journal of Investigative Dermatology. 76:164-170.
36. Watson, E. S., Murphy, J. C. and ElSohly, M. A. 1983. Immunologic Studies of Poisonous Anacardiaceae: Oral Desensitization to Poison Ivy and Oak Urushiols in Guinea Pigs. The Journal of Investigative Dermatology. 80:149-155.
37. Walker, L. A., Watson, E. S. and ElSohly, M. A. 1995. Single dose parenteral hyposensitization to poison ivy urushiol in guinea pigs. Immunopharmacology and Immunotoxicology. 17: 565-576.

The invention claimed is:

1. Urushiol esters effective for desensitizing a subject against contact dermatitis caused by allergens contained in plants of the Anacardiaceae and Ginkgoaceae families of the following formula (I)

wherein $R_1$ is an alkyl radical having 11 to 19 carbon atoms, or an unsaturated congener thereof; or mixtures thereof; and $R_2$ and $R_3$ are each independently a radical of an amino acid or a combination of amino acids or a radical of a dicarboxylic acid, with the proviso that when $R_1$ is heptadecyl or pentadecyl $R_2$ and $R_3$ cannot be alanine or alanine N-tert-butoxycarbonyl (t-BOC).

2. The urushiol esters of claim 1, wherein $R_1$ is pentadecyl, heptadecyl or nonadecyl.

3. The urushiol esters of claim 1, wherein the esters are esters of amino acids or combinations of amino acids.

4. The urushiol esters of claim 1, wherein the esters are derived from a dicarboxylic acid.

5. A pharmaceutical formulation comprising at least one urushiol ester effective for desensitizing a subject against contact dermatitis caused by allergens contained in plants of the Anacardiaceae and Ginkgoaceae families of the following formula (I)

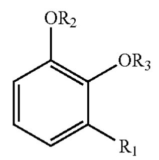

(I)

wherein $R_1$ is an alkyl radical having 11 to 19 carbon atoms, or an unsaturated congener thereof; or mixtures thereof; and $R_2$ and $R_3$ are each independently a radical of an amino acid or a combination of amino acids or a radical of a dicarboxylic acid, in sesame seed oil and about 2 to 12% by volume benzyl alcohol and about 0 to 10% by volume ethyl alcohol.

6. The pharmaceutical formulation of claim 5, wherein the composition is adapted to be administered parenterally.

7. The urushiol ester of claim 1, wherein the urushiol ester is 3-n-pentadecylcatechol-di-4-(4-aminophenyl)-butyrate, 3-n-heptadecylcatechol-di-4-(4-aminophenyl)-butyrate, 3-n-pentadecylcatechol-di-valinylvalinate or 3-n-heptadecylcatechol-di-valinylvalinate.

8. A pharmaceutical formulation according to claim 5, wherein the urushiol ester is 3-n-pentadecylcatechol-di-4-(4-aminophenyl)-butyrate, 3-n-heptadecylcatechol-di-4-(4-aminophenyl)-butyrate, 3-n-pentadecylcatechol-di-valinylvalinate or 3-n-heptadecylcatechol-di-valinylvalinate.

9. The pharmaceutical formulation of claim 8, wherein the composition is adapted to be administered parenterally.

10. The pharmaceutical formulation of claim 5, wherein $R_1$ is pentadecyl, heptadecyl or nonadecyl.

11. The pharmaceutical formulation of claim 10, wherein the composition is adapted to be administered parenterally.

12. The pharmaceutical formulation according to claim 5, wherein the esters are esters of amino acids or combinations of amino acids.

13. The pharmaceutical formulation of claim 12, wherein the composition is adapted to be administered parenterally.

14. The pharmaceutical formulation according to claim 5, wherein the at least one urushiol ester is in sesame seed oil and about 2 to 12% by volume benzyl alcohol and about 5 to 10% by volume ethyl alcohol.

15. The pharmaceutical formulation of claim 14, wherein the composition is adapted to be administered parenterally.

16. The pharmaceutical formulation according to claim 5, wherein the at least one urushiol ester is an ester of a dicarboxylic acid.

17. The pharmaceutical formulation of claim 16, wherein the composition is adapted to be administered parenterally.

18. The pharmaceutical formulation according to claim 16, wherein the at least one urushiol ester is in sesame seed oil and about 2 to 12% by volume benzyl alcohol and about 5 to 10% by volume ethyl alcohol.

19. The pharmaceutical formulation of claim 18, wherein the composition is adapted to be administered parenterally.

* * * * *